(12) United States Patent
Reich et al.

(10) Patent No.: US 7,138,384 B1
(45) Date of Patent: Nov. 21, 2006

(54) MODULATORS OF DNA CYTOSINE-5 METHYLTRANSFERASE AND METHODS FOR USE THEREOF

(75) Inventors: Norbert O. Reich, Santa Barbara, CA (US); James Flynn, Goleta, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/485,071

(22) PCT Filed: Jun. 12, 1998

(86) PCT No.: PCT/US98/12351

§ 371 (c)(1),
(2), (4) Date: Feb. 3, 2000

(87) PCT Pub. No.: WO99/12027

PCT Pub. Date: Mar. 11, 1999

Related U.S. Application Data

(60) Provisional application No. 60/057,411, filed on Aug. 29, 1997.

(51) Int. Cl.
*A01N 43/04* (2006.01)
*A61K 31/70* (2006.01)

(52) U.S. Cl. .................... 514/49; 514/42; 514/43; 514/44; 536/22.1; 536/23.1; 536/25.3; 536/25.31; 536/25.33; 536/29.1; 536/29.13

(58) Field of Classification Search .............. 536/22.1, 536/23.1, 25.3, 25.31, 25.33, 29.1, 29.13; 514/42, 43, 44, 49
See application file for complete search history.

(56) References Cited

U.S. PATENT DOCUMENTS

| | | | |
|---|---|---|---|
| 5,503,975 A | 4/1996 | Smith et al. | |
| 5,552,390 A | 9/1996 | Scholar et al. | |
| 5,578,716 A | 11/1996 | Szyf et al. | |
| 5,641,754 A | 6/1997 | Iversen | |
| 5,652,105 A | 7/1997 | Sufrin et al. | |
| 5,686,611 A | 11/1997 | Kim et al. | |
| 5,696,265 A | 12/1997 | Kim et al. | |
| 5,763,599 A | 6/1998 | Pfleiderer et al. | |
| 5,830,653 A * | 11/1998 | Froehler et al. | |
| 5,837,871 A | 11/1998 | Kim et al. | |
| 5,849,305 A | 12/1998 | Briggs et al. | |
| 5,856,090 A | 1/1999 | Epstein | |
| 6,183,952 B1 * | 2/2001 | Billing-Medel et al. | 435/6 |

FOREIGN PATENT DOCUMENTS

| | | |
|---|---|---|
| EP | 0 756 008 A2 | 1/1997 |
| EP | 0 889 122 | 1/1999 |
| WO | WO 92/06985 | 4/1992 |
| WO | WO 92/17484 | 10/1992 |
| WO | WO 95/15373 | 6/1995 |
| WO | WO 97/11972 | 4/1997 |
| WO | WO 97/38001 | 10/1997 |
| WO | WO 97/44345 | 11/1997 |
| WO | WO 97/44346 | 11/1997 |
| WO | WO 98/04725 | 2/1998 |
| WO | WO 98/20017 | 5/1998 |
| WO | WO 98/37919 | 9/1998 |
| WO | WO 98/40100 | 9/1998 |
| WO | WO 98/54310 | 12/1998 |
| WO | WO 98/54313 | 12/1998 |
| WO | WO 98/56952 | 12/1998 |

OTHER PUBLICATIONS

Volpe et al. FEBS Letters (1991), vol. 329, pp. 233-237.*
Flynn et al. Biochemistry (1996), vol. 35, pp. 7308-7315.*
T. Bestor et al. (1988) "Cloning and Sequencing . . . Cells" J. Mol. Biol. 203:971-983.
A.H. Bolden et al. (1986) "Primary DNA . . . Methyltransferases" Molecular and Cellular Biology 6(4):1135-1140.
A. Bolden et al. (1984) "DNA Methylation: Inhibition . . . Polynucleotides" J. Biol. Chem. 259:12437-12443.
J.K. Christman (1995) "5-Methyl-2' . . . methylation" Proc Natl. Acad. Sci USA 92:7347-7351.
L.S.-H. Chuang et al. (1996) "Characterisation of . . . Motifs" J. Mol. Biol. 257(5):935-48.
M.M. Hitt et al. (1988) "De Novo and . . . Methyltransferase" J. Biol. Chem. 263(9):4392-4399, plus 3 pages of supplemental material.

(Continued)

*Primary Examiner*—James O. Wilson
*Assistant Examiner*—Patrick Lewis
(74) *Attorney, Agent, or Firm*—Canady & Lortz; Karen S. Canady

(57) ABSTRACT

A synthetic oligonucleotide comprising a C-5 methylcytosine and which recognizes and binds an allosteric site on DNA methyltransferase thereby inhibiting DNA methyltransferase activity is disclosed. Also disclosed is a composition comprising a synthetic oligonucleotide of the invention. The composition is useful for inhibiting DNA methyltransferase activity, thereby inhibiting the methylation of DNA. The composition can be a pharmaceutical composition useful for treating disorders associated with methylation defects, such as cancer and certain developmental disorders. Also disclosed is a method of inhibiting methylation of DNA. The method involves contacting a DCMTase with a synthetic oligonucleotide of the invention in the presence of the DNA, thereby resulting in an enzyme/synthetic oligonucleotide complex. The presence of the complex prevents catalysis, thereby inhibiting DNA methyltransferase activity. Also disclosed is a method of treating a disorder of cell proliferation or development by administering to a subject a synthetic oligonucleotide of the invention. The inhibition of DNA methyltransferase prevents the methylation of DNA thereby treating the disorder of cell proliferation or development.

10 Claims, 26 Drawing Sheets

OTHER PUBLICATIONS

P.A. Jones (1996) "DNA Methylation . . . Cancer" Cancer Research 56:2463-2467.

A. Laayoun et al. (1995) "Methylation of . . . methyltransferase" Nucleic Acids Research 23(9):1584-1589.

H. Leonhardt et al. (1992) "A Targeting Sequence . . . Nuclei" Cell 71:865-873.

A. Reale et al. (1995) "DNA binding and . . . methyltransferase" Biochem. J. 312:855-861.

S. Ramchandani et al. (1997) "Inhibition of . . . oligodeoxynucleotide" Proc. Natl. Acad. Sci. 94:684-689.

D.V. Santi et al. (1983) "On the Mechanism . . . Analogs" Cell 33:9-10.

S.S. Smith et al. (1991) "Recognition of . . . methyltransferase" J. Mol. Biol. 217:39-51.

M. Szyf (1996) "The DNA Methylation . . . Therapy" Pharmacol. Ther. 70(1):1-37.

A. Tomassetti et al. (1988) "Isolation and . . . methyltransferase" Biochimica et Biophysica Acta 951:201-212.

J. Flynn (1997) "Murine DNA Cytosine . . . studies" UCSB Library, cataloged Sep. 1998 172 pgs.

Flynn, James et al., "DNA Binding Discrimination of the Murine DNA CytosineC$^5$ Methyltransferase", Journal of Molecular Biology, vol. 279, No. 1, May 29, 1998, pp. 101-116, XP002189817.

Tollefsbol, Trygve O. et al, "Control of Methylation Spreading in Synthetic DNA Sequences by the Murine DNA Methyltransferase", Journal of Molecular Biology, vol. 269, No. 4, Jun. 20, 1997, pp. 494-504, XP-002189816.

J. Flynn et al., 1996, "Murine DNA Cyrosine-C$^5$ Methyltransferase: Pre-Steady- and Steady-State Kinetic Analysis with Regulatory DNA Sequences," Biochemistry, 35:7308-7315.

\* cited by examiner

FIG. 1a.

Synthetic DNA Substrates Mimicking Transcriptional
*Cis*-Regulatory Elements

GC-box a:      5'-GGGAATTCAAGGGGG<u>CGGGG</u>CAAGGATCCAG-3'

GC-box b:      5'-CTGGATCCTTGCCCC<u>GCCCC</u>CTTGAATTCCC-3'

GC-box b MET:  5'-CTGGATCCTTGCCC<sup>m</sup><u>CGCCCC</u>CTTGAATTCCC-3'

CRE a:         5'-GGGAATTCAAATGA<u>CGTC</u>AAAGGATCCAG-3'

CRE b:         5'-CTGGATCCTTTGA<u>CGTC</u>ATTTGAATTCCC-3'

CRE a MET:     5'-GGGAATTCAAATGA<sup>m</sup><u>CG</u>TCAAAAGGATCCAG-3'

FIG. 1b.

| NAME | NUCLEO-TIDES | Sequence | Kii (nM) | IC50 (nM) |
|---|---|---|---|---|
| GC-Box b (SEQ ID NO: 10) | 30 | 5'-CTGGATCCTTGCCCCGCCCCTTGAATTCCC-3' | 6800 | |
| GC-Box bMET (SEQ ID NO: 10) | 30 | 5'-CTGGATCCTTGCCCmCGCCCCTTGAATTCCC-3' | 20 | 15 |
| GC Box pMET (SEQ ID NO: 10) | 30 | 5'-CTGGATCCTTGCCCmCGCCCCTTGAATTCCC-3' | | 5 |
| GC-Box cMET (SEQ ID NO: 13) | 50 | 5'- CCTACCCACCCTGATCCTTGCCCmCGCCCCTTGAATTCCAACCCTCCAC-3' | | 30 |
| GC Box dMET (SEQ ID NO: 14) | 22 | 5'-ATCCTTGCCCmCGCCCCTTGAAT-3' | | 50 |
| GC-Box eMET (SEQ ID NO: 15) | 14 | 5'TTGCCCmCGCCCCTT-3' | | 150 |
| CRE aMET (SEQ ID NO: 11) | 30 | 5'-GGGAATTCAAATGAmCGTCAAAAGGATCCAG-3' | | > 300 |

FIG. 6.

Primer C
5'-GGGAATTCATGGATCCTAAANNNNNNNNNNNNNCGNNNNNNNNNNNNNTTTCAAGCTTGTGAATTCCC-3'
3'-CCCTTAAGTACCTAGGATTTNNNNNNNNNNNNNGCNNNNNNNNNNNNNAAAGTTCGAACACTTAAGGG-5'
                                                                  Primer D

FIG. 7a.
STARTING POPULATION

GTGGGATGGGAACGAGTTGAGGAGGG
AGTGGTATGTATCGATTATACGTTGGG
GGAGGAAGTTTACGTATGGTATGGGG
TGGGAGGGGATTCGAGGTGAGAGTTG
ATAAAGTATTAGCGTAAGAGATGAAG
TGGAGGAGTTTACGGTGTAATTGTTT
GGAGTAGGTAGACGTTAAGTATGATG
GTGGGAAGGGGACGAATTTGAAGGTG
TGGTAATGTATTCGTAAATGTAAGGG
TAATAGGGGAGACGTAAATGTAAGGG
GAGTGTAGAAGTCGTAATAGATTTAG
TGAGTAGGAAAGCGAAGAGGTGTTGG

FIG. 7b. GENERATION 1

TAGGTATTGGGGCGGAAGGTGGGTGG
GGGGGTATAATACGGTGTTGGTAGGG
GGGTTGGGGTTTCGTGTGGGGGGTGT
TGTGGGTATGGGCGGTGATAGTGAAG
GGATGATGGGGTCGAGAGTGGTGGTG
TAGTGGGTGGAGCGAGTGGTGGTTGG
AGGGTGGGTGGGCGGAGTTGTTGTTG
GTGAGGAGGGAGCGGGAATGGGGGTG
GGGGGTGGGGAGCGGAGGGGGGTGAG
TGTTGGAGGGGGCGAAGGTGGTTTTG

FIG. 7c. GENERATION 3

GGGGGGGGGGGGCGAGGGGTAGATGG
GGGGGAGGGGTTCGGTGATAGGTAGG
GGGGGGGGGGTACGTGGGATGGTATG
GTGTAGGGAGTGCGAGGGGGTGTAAA
GGGGGGGGGTAGCGGTTAGATGGTGG
GGGGTGAGGGGGCGGGGGTTAGTGGG
GAGGGGGGGTTGCGTAGGGGGGTGGG
TGTGGAGGTGGGCGGGAAAGGTGATG
GGGGGGATGGGACGGATGGGGGGGGG
GGGGGTGGGGTGCGAGAGAGTTGGGG
GAGGGGTGGAGGCGGAGGTGGGTTGG
GGGGGGGGGGGGCGATAAGGGTGTG

FIG. 7d.

GENERATION 5

| G# | GpT | TpG | Sequence | TpG | GpT | G# |
|---|---|---|---|---|---|---|
| 11 | • |  | TGGGGGGGGGGGGGGAGTTGA | • |  | 7 |
| 11 |  | •• | GGGGGAGGGGAGATAGTTGTGTG | ••• | ••• | 5 |
| 10 |  |  | GGGTGGGGTGGGCGGGGGTGGGG | ••• | ••• | 9 |
| 10 |  |  | GAGGGGGGAGGGGAGGGGGTGGG | • |  | 9 |
| 10 |  | •• | GGGGGGAAGGGGCGTGGGTGGGTG | ••• | ••• | 8 |
| 10 |  | •• | -GGGAGGGGCGATGGGGTGG | ••• | ••• | 8 |
| 10 | • | •• | GGGTGGGGCGTTGTGGGTGGGG | ••• | ••• | 8 |
| 10 | • | • | GGGAGGGGTGGGCGGGTATGTGG | ••• | ••• | 7 |
| 10 | • | • | GGGGAGGGGTGGGCGGGTATGAGTGG | ••• | ••• | 7 |
| 10 | • | • | GGGGGGGAGTGCGTTGATGGGTG | •••• | ••• | 6 |
| 9 | • | • | GGGGGGGTGGATCGTGTGGGGAGGGG | • |  | 10 |
| 9 | •• | • | GGGTAGGGGTGGGGGGGTATGG | • | • | 9 |
| 9 | •• | • | GGGATGGGGTGCGGGGTATGGGGGG | • | • | 9 |

FIG. 7e.

GENERATION 5

| G# | GpT | TpG | Sequence | TpG | GpT | G# |
|---|---|---|---|---|---|---|
| 9 | • |  | GGGAGGGGGTAGCGGGAGTGTGTG | : | : | 7 |
| 9 | • |  | GGGGGTAAGGGGCGTAAGAATGGGGG | • |  | 6 |
| 9 | : | • | GGGGGGGGTCGGTAATGGGGGT |  | : | 7 |
| 9 | • | • | GGTGGGAGAGGGCGTGGTAGGTAG | : | : | 6 |
| 9 | • | • | GGGGGGGTACGAGGTTGTGTGG | : | : | 6 |
| 9 | • | : | TGGTGGAGGGGCGAAGAAGTGTG | : | : | 5 |
| 9 | • | : | GGGGGTGGGATGCGGAATAAGGATGG | • | • | 6 |
| 9 | • | • | TGAGGGGAGGGCGAATAGATGGTGG | : | : | 7 |
| 8 | : | : | GGGGGGAGTAAGCGGGGTGTGGTGG | : | : | 9 |
| 8 | : | : | TGAAGGGGGTGCGGGGTGTGGGGG- | : | : | 9 |
| 8 | • | • | GTGGTGATGGGCGGGGTGGTAGTGG | : | : | 8 |
| 8 |  | • | TGGAGGGTAGGCGTGGGGTGATGGG | : | • | 8 |

FIG. 7f.
GENERATION 5

| G# | GpT | TpG | Sequence | TpG | GpT | G# |
|---|---|---|---|---|---|---|
| 8 | . | .. | GGTAGGGAGTGGCGGGTGATGGG | .. | . | 8 |
| 8 | . | .. | GGGTGTAGAGGGGGAGTAGAGGGG | . | . | 8 |
| 8 | .. | ... | GGGTGGGTTGGCGTAATTGTGGG | .. | . | 7 |
| 8 | .. | .. | GGGTGTGTTGGGCGTGGGGTATGTAG | . | . | 6 |
| 7 | . | .. | TGGGGAGAATGGCGGGGGGGTGGG | .. | . | 10 |
| 7 | . | . | TATGGTGGGAGGGCGGGGGGGGTGG | . | . | 10 |
| 7 | .. | .. | TGGGAAAGAGGAGGCGTGAGTGGGGGG | .. | . | 9 |
| 7 | . | .. | TGTAGGGAGGACGGGGATGGGGTG | .. | . | 9 |
| 7 | .. | .. | GGGTGGGTAATGCGTAGGGTGGGGG | .. | . | 9 |
| 7 | .. | .. | GTGTGGGTAAGGCGTATGGGGTGG | . | . | 8 |
| 7 | ... | ... | TGGAGGGTGTGCGGGTGAGGTGGTGG | .. | .. | 8 |
| 7 | ... | ... | GGTGGTGGTGGATCGGGGTTGTGATGG | ... | .. | 7 |

FIG.7g.

GENERATION 5

| G# | GpT | TpG | Sequence | TpG | GpT | G# |
|---|---|---|---|---|---|---|
| 7 | : | : | GGGGGTAAAGTGCGGGTGGTTGATGG | : | : | 7 |
| 7 | : | :: | GTGGAGGTGTTGCGTAGTGTGGGAGG | : | : | 7 |
| 7 | : | :: | GTGGGGAATGGTCGGTTATGGTGGGG | : | : | 7 |
| 7 | : | :: | GGGATGTGGTAGCGGGGGGTGTTAG | :: | : | 7 |
| 7 | : | : | GGGGTAGGAGTTCGTAGGGGTGTT | : | : | 6 |
| 7 | : | : | GAGGTGGTGGATCGGGATGATGATT | : | : | 5 |
| 6 | : | :: | TGGGGGAAATACGGGGAGGGTGGTA | . | : | 8 |
| 6 | . | . | GGAGTAGGGTTACGTGGTAATGG | : | . | 6 |
| 6 | : | :: | GAGGAGTAAAGGCGTGTGTGTGGTG | :::: | . | 6 |
| 5 | :: | . | TGGATGAGAGTGCGTGTATGATAAGG | : | . | 4 |
| 5 | . | . | AGGGTTAGTGAACGGGGGAGGTGG | . | . | 10 |
|  |  |  | GAGAAGGGTAAACGTGGGGAGGGGA | . |  | 9 |

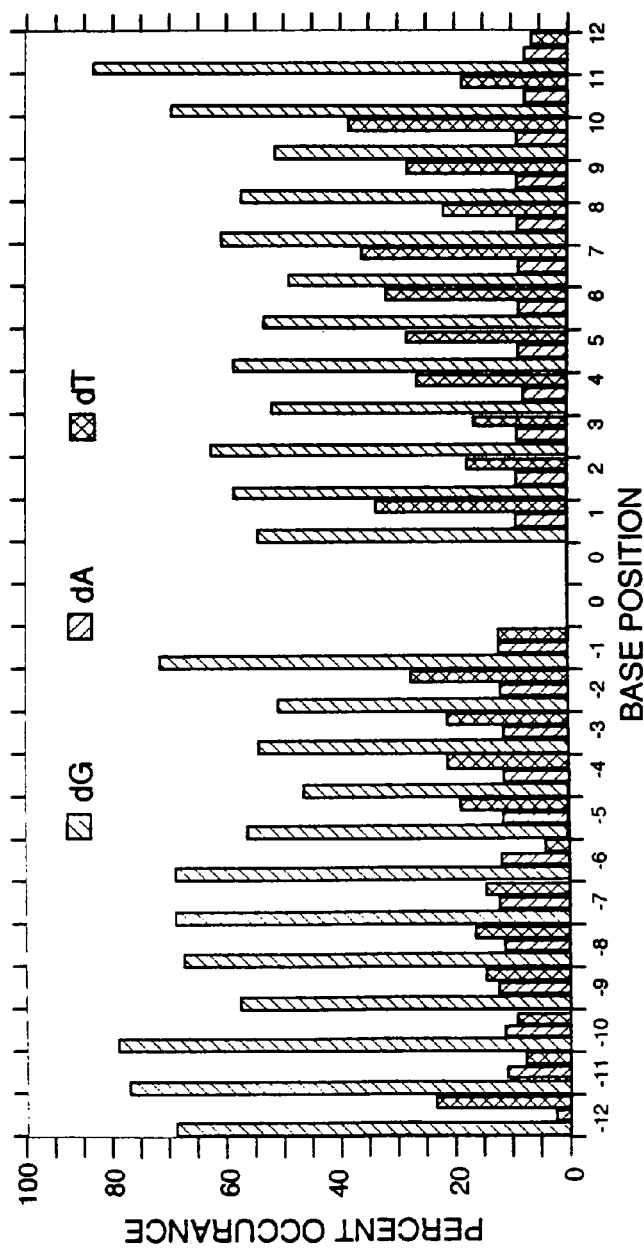

FIG.9a

DEFINITION Lyt-2.2 gene, T-cell differentiation antigen, 3' UTR.
ACCESSION GB_RO:MMLYT22

```
                    TGGGGGGGGCGCGGGGGGAGTTTGA
                    ||||||||||  ||||||||||||
GAACAATGGGGCGCTGGGGGGGGGGGGGGCTTTAGCTATGTCAGAATTCA
    5100      5110       5120       5130      5140
```

DEFINITION homeo box 2.6 (Hox-2.6) mRNA
ACCESSION GB_RO:MUSHOX26

```
                GGGATGGGGGTGCGGGGTATGGGGGGG
                ||  ||||||||| ||||||||||||
GGGGAACAGCGAGCACCGAAGGGGTGCGGGGTATGGAAGGGTCCCCGGGCTTGAGC
   870      880       890      900      910      920
```

DEFINITION growth arrest-specific promoter gene, gas-1
ACCESSION GB_RO:MMGAS1PRA

```
                    GGTGGTGGTGATCGGGGTTGTGATGG
                    ||||| | |||||  ||||  ||||
TGTCCTTCTTGTGGTGGTAGAGGTCGTGGTTGTGATGGTGGCTCGGTGTGTGT
   2480      2490       2500      2510      2520
```

FIG.9b.

DEFINITION pim-1 proto-oncogene, pim-1 protein kinase, CpG island,
5' UTR region.
ACCESSION GB_RO:MUSPIM1

```
                            GAGGGGGGGAGCGGAGGGGGTTGGG
                            ||||||| |||||||||||||| ||
GAGGGGGTGTAGCCGCGAGGGGGGGAGCGGAGGGGGAGGGCCCTGGTCCCGCCGCC
     1500           1510          1520         1530         1540
```

DEFINITION neuronal dihydropyridine-sensitive L-type calcium
channel alpha-1 subunit mRNA, 3' UTR.
ACCESSION GB_RO:MUSDHPCC

```
                     CCCCCACCCACAAACGCCACCCCCACCC
                     ||||| |  |||||||||| ||||||||
TCTTTAAATGGTGCGGTCCACCCCCACCGCCACCCCCACCCCCCACTGGAGCAAGG
    8330      8340       8350       8360      8370       8380
```

FIG.9c.

HUMAN SEQUENCES

DEFINITION  Huntington's Disease Region, chromsome 4p16.3.
ACCESSION  GB_PR:HSL1C2

DEFINITION  Human Down Syndrome region of chomosome 21.
ACCESSION  GB_HTG:HSAC000002

DEFINITION  upstream region of HoxA7 gene, CpG island.
ACCESSION  GB_PR:HSHCRDNA DEFINITION  chromosome 22 CpG island DNA
ACCESSION  GB_PR:HS303B3

DEFINITION  CpG island DNA.
ACCESSION  GB_PR:HS167B9F

DEFINITION  Y chromosome sex determining region, Yp pseudoautosomal boundary, PAB1.
ACCESSION  GB_PR:HSCAMF3X1

DEFINITION  creatine transporter and paralogous genes, pericentomeric repeats on chromosome 16.
ACCESSION  GB_PR:HSU41302

DEFINITION  cathepsin D (cat D) gene, exon 5.
ACCESSION  GB_PR:HUMCATD3

FIG.9d.

DEFINITION   argininosuccinate synthetase gene 5' end, CpG island
ACCESSION    GB_PR:HSASG5E DEFINITION   argininosuccinate synthetase gene 5' end, CpG island
ACCESSION    GB_PR:HUMAS1

DEFINITION   vimentin gene, 5' regulatory region, CpG island.
ACCESSION    GB_PR:HUMVIM DEFINITION   vimentin gene, exon 1, 5' end CpG island.
ACCESSION    GB_PR:HUMVIM02

DEFINITION   vimentin gene, 5' end, CpG island.
ACCESSION    GB_PR:HUMVIMAA

DEFINITION   vimentin gene, 5' end, CpG island
ACCESSION    GB_PR:HSVIM5RR

DEFINITION   chromosome 22 DNA *SEQUENCING IN PROCESS*, CpG island
ACCESSION    GB_HTG:HS17OA21

SEQUENCE LISTING (1) GENERAL INFORMATION:

(iii) NUMBER OF SEQUENCES: 110

(2) INFORMATION FOR SEQ ID NO: 1:

(i) SEQUENCE CHARACTERISTICS:
      (A) LENGTH: 26 base pairs
      (B) TYPE: nucleic acid
      (C) STRANDEDNESS: double
      (D) TOPOLOGY: linear (xi) SEQUENCE DESCRIPTION: SEQ ID NO: 1:

GGGGGGGRRK KGCGKGGKGK KGKKGG                 26

(2) INFORMATION FOR SEQ ID NO: 2:

(i) SEQUENCE CHARACTERISTICS:
      (A) LENGTH: 26 base pairs
      (B) TYPE: nucleic acid
      (C) STRANDEDNESS: double
      (D) TOPOLOGY: linear (xi) SEQUENCE DESCRIPTION: SEQ ID NO: 2:

KGGRKKRDDD KRCGKRRDKK KKKKKG                  26

(2) INFORMATION FOR SEQ ID NO: 3:

(i) SEQUENCE CHARACTERISTICS:
      (A) LENGTH: 10 base pairs
      (B) TYPE: nucleic acid
      (C) STRANDEDNESS: double
      (D) TOPOLOGY: linear (xi) SEQUENCE DESCRIPTION: SEQ ID NO: 3:

GGGGCGGGGC                                  10

(2) INFORMATION FOR SEQ ID NO: 4:

(i) SEQUENCE CHARACTERISTICS:
      (A) LENGTH: 10 base pairs
      (B) TYPE: nucleic acid
      (C) STRANDEDNESS: double
      (D) TOPOLOGY: linear (xi) SEQUENCE DESCRIPTION: SEQ ID NO: 4:

CCAACGTTGG                                   10

```
(2) INFORMATION FOR SEQ ID NO: 5:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (xi) SEQUENCE DESCRIPTION: SEQ ID NO: 5:

CCAAGATTGG                                                              10

(2) INFORMATION FOR SEQ ID NO: 6:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (xi) SEQUENCE DESCRIPTION: SEQ ID NO: 6:

CGATCGATCG                                                              10

(2) INFORMATION FOR SEQ ID NO: 7:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (xi) SEQUENCE DESCRIPTION: SEQ ID NO: 7:

CCAACGTTGG                                                              10

(2) INFORMATION FOR SEQ ID NO: 8:

(i) SEQUENCE CHARACTERISTICS:
        (A) LENGTH: 12 base pairs
        (B) TYPE: nucleic acid
        (C) STRANDEDNESS: double
        (D) TOPOLOGY: linear (xi) SEQUENCE DESCRIPTION: SEQ ID NO: 8:

CCGTACGTAC GG                                                           12

(2) INFORMATION FOR SEQ ID NO: 9:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (xi) SEQUENCE DESCRIPTION: SEQ ID NO: 9:

GGGAATTCAA GGGGCGGGGC AAGGATCCAG                                        30

(2) INFORMATION FOR SEQ ID NO: 10:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (xi) SEQUENCE DESCRIPTION: SEQ ID NO: 10:

CTGGATCCTT GCCCCGCCCC TTGAATTCCC                                        30
```

```
(2) INFORMATION FOR SEQ ID NO: 11:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (xi) SEQUENCE DESCRIPTION: SEQ ID NO: 11:

GGGAATTCAA ATGACGTCAA AAGGATCCAG                                    30

(2) INFORMATION FOR SEQ ID NO: 12:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (xi) SEQUENCE DESCRIPTION: SEQ ID NO: 12:

CTGGATCCTT TTGACGTCAT TTGAATTCCC                                    30

(2) INFORMATION FOR SEQ ID NO: 13:

(i) SEQUENCE CHARACTERISTICS:
        (A) LENGTH: 50 base pairs
        (B) TYPE: nucleic acid
        (C) STRANDEDNESS: double
        (D) TOPOLOGY: linear (xi) SEQUENCE DESCRIPTION: SEQ ID NO: 13:

CCTACCCACC CTGGATCCTT GCCCCGCCCC TTGAATTCCC AACCCTCCAC              50

(2) INFORMATION FOR SEQ ID NO: 14:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (xi) SEQUENCE DESCRIPTION: SEQ ID NO: 14:

ATCCTTGCCC CGCCCCTTGA AT                                            22

(2) INFORMATION FOR SEQ ID NO: 15:

(i) SEQUENCE CHARACTERISTICS:
        (A) LENGTH: 14 base pairs
        (B) TYPE: nucleic acid
        (C) STRANDEDNESS: double
        (D) TOPOLOGY: linear (xi) SEQUENCE DESCRIPTION: SEQ ID NO: 15:

TTGCCCCGCC CCTT                                                     14

(2) INFORMATION FOR SEQ ID NO: 16:

(i) SEQUENCE CHARACTERISTICS:
        (A) LENGTH: 66 base pairs
        (B) TYPE: nucleic acid
        (C) STRANDEDNESS: double
        (D) TOPOLOGY: linear (xi) SEQUENCE DESCRIPTION: SEQ ID NO: 16:

GGGAATTCAT GGATCCTAAA NNNNNNNNNN NNCGNNNNNN NNNNNNTTTC AAGCTTGTGA   60

ATTCCC                                                              66
```

(2) INFORMATION FOR SEQ ID NO: 17:

(i) SEQUENCE CHARACTERISTICS:
        (A) LENGTH: 66 base pairs
        (B) TYPE: nucleic acid
        (C) STRANDEDNESS: double
        (D) TOPOLOGY: linear (xi) SEQUENCE DESCRIPTION: SEQ ID NO: 17:

CCCTTAAGTA CCTAGGATTT NNNNNNNNNN NNGCNNNNNN NNNNNNAAAG TTCGAACACT     60

TAAGGG                                                                66

(2) INFORMATION FOR SEQ ID NO: 18:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 18:

GTGGGATGGG AACGAGTTGA GGAGGG                                          26

(2) INFORMATION FOR SEQ ID NO: 19:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 19:

AGTGGTATGT ATCGATTATA GTTGGG                                          26

(2) INFORMATION FOR SEQ ID NO: 20:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 20:

GGAGGAAGTT TACGTATGGT ATGGGG                                          26

(2) INFORMATION FOR SEQ ID NO: 21:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 21:

TGGGAGGGGA TTCGAGGTGA GAGTTG                                          26

(2) INFORMATION FOR SEQ ID NO: 22:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 22:

ATAAAGTATT AGCGTAAGAG ATGAAG                                          26

(2) INFORMATION FOR SEQ ID NO: 23:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 23:

TGGAGGAGTT TACGGTGTAA TTGTTT                        26

(2) INFORMATION FOR SEQ ID NO: 24:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 24:

GGAGTAGGTA GACGTTAAGT ATGATG                        26

(2) INFORMATION FOR SEQ ID NO: 25:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 25:

GTGGGAAGGG GACGAATTTG AAGGTG                        26

(2) INFORMATION FOR SEQ ID NO: 26:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 26:

TGGTAATGTA TTCGTAAATG TAAGGG                        26

(2) INFORMATION FOR SEQ ID NO: 27:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 27:

TAATAGGGGA GACGTAAATG TAAGGG                        26

(2) INFORMATION FOR SEQ ID NO: 28:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 28:

GAGTGTAGAA GTCGTAATAG ATTTAG                        26

(2) INFORMATION FOR SEQ ID NO: 29:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 29:

TGAGTAGGAA AGCGAAGAGG TGTTGG                                      26

(2) INFORMATION FOR SEQ ID NO: 30:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 30:

TAGGTATTGG GGCGGAAGGT GGGTGG                                      26

(2) INFORMATION FOR SEQ ID NO: 31:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 31:

GGGGGTATAA TACGGTGTTG GTAGGG                                      26

(2) INFORMATION FOR SEQ ID NO: 32:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 32:

GGGTTGGGGT TTCGTGTGGG GGGTGT                                      26

(2) INFORMATION FOR SEQ ID NO: 33:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 33:

TGTGGGTATG GGCGGTGATA GTGAAG                                      26

(2) INFORMATION FOR SEQ ID NO: 34:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 34:

GGATGATGGG GTCGAGAGTG GTGGTG                                      26

(2) INFORMATION FOR SEQ ID NO: 35:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 35:

TAGTGGGTGG AGCGAGTGGT GGTTGG                          26

(2) INFORMATION FOR SEQ ID NO: 36:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 36:

AGGGTGGGTG GGCGGAGTTG TTGTTG                          26

(2) INFORMATION FOR SEQ ID NO: 37:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 37:

GTGAGGAGGG AGCGGGAATG GGGGTG                          26

(2) INFORMATION FOR SEQ ID NO: 38:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 38:

GGGGGTGGGG AGCGGAGGGG GGTGAG                          26

(2) INFORMATION FOR SEQ ID NO: 39:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 39:

TGTTGGAGGG GGCGAAGGTG GTTTTG                          26

(2) INFORMATION FOR SEQ ID NO: 40:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 40:

GGGGGGGGGG GGCGAGGGGT AGATGG                          26

(2) INFORMATION FOR SEQ ID NO: 41:

(i) SEQUENCE CHARACTERISTICS:
            (A) LENGTH: 26 base pairs
            (B) TYPE: nucleic acid
            (C) STRANDEDNESS: double
            (D) TOPOLOGY: linear (xi) SEQUENCE DESCRIPTION: SEQ ID NO: 41:

GGGGGAGGGG TTCGGTGATA GGTAGG                                                    26

(2) INFORMATION FOR SEQ ID NO: 42:

(i) SEQUENCE CHARACTERISTICS:
            (A) LENGTH: 26 base pairs
            (B) TYPE: nucleic acid
            (C) STRANDEDNESS: double
            (D) TOPOLOGY: linear (xi) SEQUENCE DESCRIPTION: SEQ ID NO: 42:

GGGGGGGGGG TACGTGGGAT GGTATG                                                    26

(2) INFORMATION FOR SEQ ID NO: 43:

(i) SEQUENCE CHARACTERISTICS:
            (A) LENGTH: 26 base pairs
            (B) TYPE: nucleic acid
            (C) STRANDEDNESS: double
            (D) TOPOLOGY: linear (xi) SEQUENCE DESCRIPTION: SEQ ID NO: 43:

GTGTAGGGAG TGCGAGGGGG TGTAAA                                                    26

(2) INFORMATION FOR SEQ ID NO: 44:

(i) SEQUENCE CHARACTERISTICS:
            (A) LENGTH: 26 base pairs
            (B) TYPE: nucleic acid
            (C) STRANDEDNESS: double
            (D) TOPOLOGY: linear (xi) SEQUENCE DESCRIPTION: SEQ ID NO: 44:

GGGGGGGGGT AGCGGTTAGA TGGTGG                                                    26

(2) INFORMATION FOR SEQ ID NO: 45:

(i) SEQUENCE CHARACTERISTICS:
            (A) LENGTH: 26 base pairs
            (B) TYPE: nucleic acid
            (C) STRANDEDNESS: double
            (D) TOPOLOGY: linear (xi) SEQUENCE DESCRIPTION: SEQ ID NO: 45:

GGGGTGAGGG GGCGGGGGTT AGTGGG                                                    26

(2) INFORMATION FOR SEQ ID NO: 46:

(i) SEQUENCE CHARACTERISTICS:
            (A) LENGTH: 26 base pairs
            (B) TYPE: nucleic acid
            (C) STRANDEDNESS: double
            (D) TOPOLOGY: linear (xi) SEQUENCE DESCRIPTION: SEQ ID NO: 46:

GAGGGGGGGT TGCGTAGGGG GGTGGG                                                    26

(2) INFORMATION FOR SEQ ID NO: 47:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 47:

TGTGGAGGTG GGCGGGAAAG GTGATG                                            26

(2) INFORMATION FOR SEQ ID NO: 48:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 48:

GGGGGGATGG GACGGATGGG GGGGGG                                            26

(2) INFORMATION FOR SEQ ID NO: 49:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 49:

GGGGGTGGGG TGCGAGAGAG TTGGGG                                            26

(2) INFORMATION FOR SEQ ID NO: 50:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 50:

GAGGGGTGGA GGCGGAGGTG GGTTGG                                            26

(2) INFORMATION FOR SEQ ID NO: 51:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 51:

GGGGGGGGGG GGCGGATAAG GGTGTG                                            26

(2) INFORMATION FOR SEQ ID NO: 52:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 52:

TGGGGGGGGG GGCGGGGGGA GTTTGA                                            26

(2) INFORMATION FOR SEQ ID NO: 53:

(i) SEQUENCE CHARACTERISTICS:

(A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 53:

GGGGGGGAGG GGCGGATAGT TGTGTG                                              26

(2) INFORMATION FOR SEQ ID NO: 54:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 54:

GGGTGGGGTG GGCGGTGGGG TGTGGG                                              26

(2) INFORMATION FOR SEQ ID NO: 55:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 55:

GAGGGGGGGG AGCGGAGGGG GTTGGG                                              26

(2) INFORMATION FOR SEQ ID NO: 56:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 56:

GGGGGGGAAG GGCGTGGGGT TGGGTG                                              26

(2) INFORMATION FOR SEQ ID NO: 57:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (xi) SEQUENCE DESCRIPTION: SEQ ID NO: 57:

GGGAGGGGGG GCGATGGGGT GGTGG                                               25

(2) INFORMATION FOR SEQ ID NO: 58:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 58:

GGGTGGGGGT GGCGTTGTGG GTGGGG                                              26

(2) INFORMATION FOR SEQ ID NO: 59:

(i) SEQUENCE CHARACTERISTICS:
        (A) LENGTH: 26 base pairs

```
        (B) TYPE: nucleic acid
        (C) STRANDEDNESS: double
        (D) TOPOLOGY: linear (xi) SEQUENCE DESCRIPTION: SEQ ID NO: 59:

GGGAGGGGGT GGCGGTGGGT ATGTGG                                            26

(2) INFORMATION FOR SEQ ID NO: 60:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 60:

GGGGAGGGTG GGCGGGTATG GAGTGG                                            26

(2) INFORMATION FOR SEQ ID NO: 61:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 61:

GGGGGGGGAG TGCGTTGATG GGTGTG                                            26

(2) INFORMATION FOR SEQ ID NO: 62:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 62:

GGGGGGGTGG ATCGTGGGGG GAGGGG                                            26

(2) INFORMATION FOR SEQ ID NO: 63:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 63:

GGGGTAGGGT GGCGGGGGGG GTATGG                                            26

(2) INFORMATION FOR SEQ ID NO: 64:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 64:

GGGATGGGGG TGCGGGGTAT GGGGGG                                            26

(2) INFORMATION FOR SEQ ID NO: 65:

(i) SEQUENCE CHARACTERISTICS:
        (A) LENGTH: 26 base pairs
        (B) TYPE: nucleic acid
```

```
        (C) STRANDEDNESS: double
        (D) TOPOLOGY: linear (xi) SEQUENCE DESCRIPTION: SEQ ID NO: 65:

GGGAGGGGGT AGCGGGAGTG TGTGTG                                              26

(2) INFORMATION FOR SEQ ID NO: 66:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 66:

GGGGGTAAGG GGCGTAAGAA TGGGGG                                              26

(2) INFORMATION FOR SEQ ID NO: 67:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 67:

GGGGGGGTGG TTCGGTAATG GGGGGT                                              26

(2) INFORMATION FOR SEQ ID NO: 68:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 68:

GGTGGGAGAG GGCGTGGTGT AGGTAG                                              26

(2) INFORMATION FOR SEQ ID NO: 69:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 69:

GGGGGGGGTG TACGAGGTTT GTGTGG                                              26

(2) INFORMATION FOR SEQ ID NO: 70:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 70:

TGGTGGAGGG GGCGAAGAAG TGTGTG                                              26

(2) INFORMATION FOR SEQ ID NO: 71:

(i) SEQUENCE CHARACTERISTICS:
        (A) LENGTH: 26 base pairs
        (B) TYPE: nucleic acid
        (C) STRANDEDNESS: double
```

(D) TOPOLOGY: linear (xi) SEQUENCE DESCRIPTION: SEQ ID NO: 71:

GGGGGTGGGA TGCGGAATAA GGATGG                                    26

(2) INFORMATION FOR SEQ ID NO: 72:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 72:

TGAGGGGGAG GGCGAATAGA TGGTGG                                    26

(2) INFORMATION FOR SEQ ID NO: 73:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 73:

GGGGGGAGTA AGCGGGGTG TGGTGG                                     26

(2) INFORMATION FOR SEQ ID NO: 74:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (xi) SEQUENCE DESCRIPTION: SEQ ID NO: 74:

TGAAGGGGGG TGCGGGGTGT GGGGG                                     25

(2) INFORMATION FOR SEQ ID NO: 75:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 75:

GTGGTGATGG GGCGGGGTGG TAGTGG                                    26

(2) INFORMATION FOR SEQ ID NO: 76:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 76:

TGGAGGGGTA GGCGTGGGGT GATGGG                                    26

(2) INFORMATION FOR SEQ ID NO: 77:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 77:

GGTAGGGAGT GGCGGGTGGT GATGGG                                              26

(2) INFORMATION FOR SEQ ID NO: 78:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 78:

GGGTGTAGAG GGCGGGAGTA GAGGGG                                              26

(2) INFORMATION FOR SEQ ID NO: 79:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 79:

GGGTGGGTTT GGCGTAATTG TGTGGG                                              26

(2) INFORMATION FOR SEQ ID NO: 80:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 80:

GGGTGTGTTG GGCGTGGGGT ATGTAG                                              26

(2) INFORMATION FOR SEQ ID NO: 81:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 81:

TGGGGAGAAT GGCGGGGGGT GGTGGG                                              26

(2) INFORMATION FOR SEQ ID NO: 82:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 82:

TATGGTGGGA GGCGGGGGGG GGTTGG                                              26

(2) INFORMATION FOR SEQ ID NO: 83:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 83:

TGGGGAAAGA GGCGTGAGTG GGGGGG                                   26

(2) INFORMATION FOR SEQ ID NO: 84:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 84:

TGTAGGGGAG GACGGGGGAT GGGGTG                                   26

(2) INFORMATION FOR SEQ ID NO: 85:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 85:

GGGTGGGTAA TGCGTAGGGT GGGGGG                                   26

(2) INFORMATION FOR SEQ ID NO: 86:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 86:

GTGTGGGTAA GGCGGTATGG GGGTGG                                   26

(2) INFORMATION FOR SEQ ID NO: 87:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 87:

TGGAGGGTGT TGCGGTGAGG TGGTGG                                   26

(2) INFORMATION FOR SEQ ID NO: 88:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 88:

GGTGGTGGTG ATCGGGGTTG TGATGG                                   26

(2) INFORMATION FOR SEQ ID NO: 89:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 89:

GGGGGTAAAG TGCGGGTGGT TGATGG                                                26

(2) INFORMATION FOR SEQ ID NO: 90:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 90:

GTGGAGGTGT TGCGTAGTGT GGGAGG                                                26

(2) INFORMATION FOR SEQ ID NO: 91:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 91:

GTGGGGAATG GTCGGTTATG GTGGGG                                                26

(2) INFORMATION FOR SEQ ID NO: 92:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 92:

GGGATGTGGT AGCGGGGGTG TGTTAG                                                26

(2) INFORMATION FOR SEQ ID NO: 93:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 93:

GGGGTAGGAG TTCGTAGGGG TGTGTT                                                26

(2) INFORMATION FOR SEQ ID NO: 94:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 94:

GAGGTGGTGG ATCGGGATGA TGGATT                                                26

(2) INFORMATION FOR SEQ ID NO: 95:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 95:

TGGGGGGAAA TACGGGGAGG GTGGTA                                              26

(2) INFORMATION FOR SEQ ID NO: 96:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 96:

GGAGTAGGGT TACGTGGTGG TAATGG                                              26

(2) INFORMATION FOR SEQ ID NO: 97:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 97:

GAGGAGTAAA GGCGTGTGTT GTGGTG                                              26

(2) INFORMATION FOR SEQ ID NO: 98:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 98:

TGGATGAGAG TGCGTGTATG ATAAGG                                              26

(2) INFORMATION FOR SEQ ID NO: 99:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 99:

AGGGTTAGTG AACGGGGGGG AGGTGG                                              26

(2) INFORMATION FOR SEQ ID NO: 100:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 100:

GAGAAGGGTA AACGTGGGGG AGGGGA                                              26

(2) INFORMATION FOR SEQ ID NO: 101:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 101:

TGGGGGGGGG GGCGGGGGGA GTTTGA                                              26

(2) INFORMATION FOR SEQ ID NO: 102:

(i) SEQUENCE CHARACTERISTICS:
        (A) LENGTH: 56 base pairs
        (B) TYPE: nucleic acid
        (C) STRANDEDNESS: double
        (D) TOPOLOGY: linear (xi) SEQUENCE DESCRIPTION: SEQ ID NO: 102:

GAACAATGGG GGCGCTGGGG GGGGGGGCGG GGGGGCTTTA GCTATGTCAG AATTCA        56

(2) INFORMATION FOR SEQ ID NO: 103:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 103:

GGGATGGGGG TGCGGGGTAT GGGGGG        26

(2) INFORMATION FOR SEQ ID NO: 104:

(i) SEQUENCE CHARACTERISTICS:
        (A) LENGTH: 57 base pairs
        (B) TYPE: nucleic acid
        (C) STRANDEDNESS: double
        (D) TOPOLOGY: linear (xi) SEQUENCE DESCRIPTION: SEQ ID NO: 104:

GGGGAACAGC GAGCACCGAA GGGGGTGCGG GGTATGGGAG GGTCCCCGGG CTTGAGC        57

(2) INFORMATION FOR SEQ ID NO: 105:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 105:

GGTGGTGGTG ATCGGGGTTG TGATGG        26

(2) INFORMATION FOR SEQ ID NO: 106:

(i) SEQUENCE CHARACTERISTICS:
        (A) LENGTH: 56 base pairs
        (B) TYPE: nucleic acid
        (C) STRANDEDNESS: double
        (D) TOPOLOGY: linear (xi) SEQUENCE DESCRIPTION: SEQ ID NO: 106:

TGTCCTTCTT GTGGTGGTGG TAGAGGTCGT GGTTGTGATG GTGGCTCGGT GTGTGT        56

(2) INFORMATION FOR SEQ ID NO: 107:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 107:

GAGGGGGGGG AGCGGAGGGG GTTGGG        26

(2) INFORMATION FOR SEQ ID NO: 108:

(i) SEQUENCE CHARACTERISTICS:
        (A) LENGTH: 56 base pairs
        (B) TYPE: nucleic acid
        (C) STRANDEDNESS: double
        (D) TOPOLOGY: linear (xi) SEQUENCE DESCRIPTION: SEQ ID NO: 108:

GAGGGGTGTA GCCGCGAGGG GGCGGAGCGG AGGGGGAGGG CCCTGGTCCC GCCGCC      56

(2) INFORMATION FOR SEQ ID NO: 109:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (xi) SEQUENCE DESCRIPTION: SEQ ID NO: 109:

CCCCACCCAC AACGCCACCC CCACCC      26

(2) INFORMATION FOR SEQ ID NO: 110:

(i) SEQUENCE CHARACTERISTICS:
        (A) LENGTH: 56 base pairs
        (B) TYPE: nucleic acid
        (C) STRANDEDNESS: double
        (D) TOPOLOGY: linear (xi) SEQUENCE DESCRIPTION: SEQ ID NO: 110:

TCTTTAAATG GTGCGGTCCA CCCCCACCGC CACCCCCACC CCCCACTGGA GCAAGG      56

MODULATORS OF DNA CYTOSINE-5 METHYLTRANSFERASE AND METHODS FOR USE THEREOF

This application is based on U.S. provisional patent application Ser. No. 60/057,411, filed Aug. 29, 1997, the entire contents of which are hereby incorporated by reference into this application. Throughout this application various publications are referenced. The disclosures of these publications in their entireties are hereby incorporated by reference into this application in order to more fully describe the state of the art to which this invention pertains.

This invention was made with Government support under Grant No. GM46333, awarded by the National Institutes of Health to Norbert O. Reich. The Government has certain rights in this invention.

BACKGROUND OF THE INVENTION

In eukaryotic organisms, DNA methylation is catalyzed by an S-adenosyl-L-methionine (AdoMet)$^1$-dependent DNA cytosine-$C^5$ methyltransferase (DCMTase, EC 2.1.1.37). Methyl group transfer to the cytosine-$C^5$ position occurs predominately within the cytosyl-guanosyl (CpG) context (Boyes, J., & Bird, A. P., 1991, DNA methylation inhibits transcription indirectly via a methyl-CpG binding protein, Cell 64:1123–1134). The genomic distribution of 5-methylcytosine (5-mC) dynamically changes throughout ontogeny (Razin, A., & Riggs, A. D., 1980, DNA methylation and gene function, Science 210:604–609; Kafri, T. et al., 1992, Developmental pattern of gene-specific DNA methylation in the mouse embryo and germ line, Genes and Dev. 6:705–714). The methylation state of a gene specifically affects transcription.

DCMTase is involved in mammalian development by way of an undefined process that can lead to gene regulation (reviewed in Jost, J. P., & Saluz, H. P., 1993, DNA Methylation: Molecular Biology and Biological Significance, Birkhauser Verlag, Basel). Proper DCMTase function is essential for viable development and for normal cellular activity (Li, E. et al., 1992, Targeted mutation of the DNA methyltransferase gene results in embyonic lethality, Cell 69:915–926).

Cytosine methylation is the predominant epigenetic event in the modification of eukaryotic DNA. To date only a single DCMTase has been identified in several metazoan organisms (Yoder, J. A., et al., 1996, New 5' regions of the murine and human genes for DNA cytosine-5 methyltransferase, J. Biol. Chem. 271:31092–31097). The function most often identified with cytosine $C^5$ methylation (5-$^m$C) in higher eukaryotes is the regulation of transcription (Jost, J. P., & Saluz, H. P., 1993, DNA Methylation: Molecular Biology and Biological Significance, Birkhauser Verlag, Basel). Generally, hypermethylated genes are transcriptionally silent and inheritance of the proper genomic methylation pattern is critical to viable development as shown by DCMTase gene knock-outs in mice (Li, E., et al., 1992, Targeted mutation of the DNA methyltransferase gene results in embryonic lethality, Cell 69:15–926). Anti-sense directed inactivation of DCMTase mRNA as well as the incorporation of the cytosine analogs 5-azacytidine and 5-fluorocytidine into DNA interfere with DCMTase function and lead to cytological dysfunction (Ramachandani, S., et al., 1997, Inhibition of tumorigenesis by a cytosine-DNA, methyltransferase, antisense oligodeoxynucleotide, Proc. Natl. Acad. Sci. USA 94:684–689; Jones, P. A., 1985, Altering gene expression with 5-azacytidine, Cell 40:485–486).

Eukaryotic DCMTase cDNAs have been cloned and sequenced; five are from animal sources (mouse: Bestor, T., et al., 1988, Cloning and sequencing of a cDNA encoding DNA methyltransferase of mouse cells, J. Mol. Biol. 203: 971–983; human: Yen, R. C., et al., 1992, Isolation and characterization of the cDNA encoding human DNA methyltransferase, Nucleic Acids Res. 20:2287–2291; chicken: Tajima, S., et al., 1995, Isolation and expression of a chicken DNA methyltransferase cDNA, J. Biochem. 117:1050–1057; frog: Kimura et al., 1996, Isolation and expression of a *Xenopus laevis* DNA methyltransferase cDNA, Journal of Biochemistry, 120:1182–1189; sea urchin: Aniello et al., 1996, Isolation of cDNA clones encoding DNA methyltransferase of sea urchin *P. lividus*: expression during embryonic development, Gene 178:57–61). These DCMTases are composed of a large amino-terminal domain and a smaller carboxy-terminal domain that contains many of the major motifs found in prokaryotic DCMTases (Posfai, J., et al., 1989, Predictive motifs derived from cytosine methyltransferases, Nucleic Acids Res 17:2421–2435). The amino-terminal domain has been implicated in nuclear localization to DNA replication foci during S-phase (Leonhardt, H., et al., 1992, A targeting sequence directs DNA methyltransferase to sites of DNA replication in mammalian nuclei, Cell 71:865–873), metal binding by zinc finger domains, and DNA binding (Bestor, T. H., 1992, Activation of the mammalian DNA methyltransferase by cleavage of a Zn binding regulatory domain, EMBO 11:2611–2617; Chuang, L. S., et al., 1996, Characterisation of independent DNA and multiple Zn-binding domains at the N terminus of human DNA-(cytosine-5) methyltransferase: modulating the property of a DNA-binding domain by contiguous Zn-binding motifs, Chia, J., and Li, B. F. L., J. Mol. Biol. 257:935–948).

Although the cellular processes that determine the genomic patterns of DNA methylation are not understood, DCMTase has an essential role in these processes. A basic understanding of the binding and catalytic DNA sequence specificity (discrimination) of the enzyme, and the factors which regulate this specificity are important. Since the mammalian enzyme is a relatively large, 183 kDa protein, DNA sequences flanking the cognate CpG may modulate the ability of the enzyme to methylate particular CpG sites. However, the CpG flanking sequence preferences of the enzyme, and its preference for single- and double-stranded substrates have not been rigorously addressed by previous investigators (Bestor, T. H. et al., 1992, CpG islands in mammalian gene promoters are inherently resistant to de novo methylation, GATA 9:48–53; Hepburn, P. A., et al., 1991, Enzymatic methylation of cytosine in DNA is prevented by adjacent O$^6$-methylguanine residues, J. Biol. Chem. 266:7985–7987; Bolden, A. H., et al., 1986, Primary DNA sequence determines sites of maintenance and de novo methylation by mammalian DNA methyltransferases, Mol. Cell. Bio. 6:1135–1140; Pfeifer, G. P., et al., 1985, Mouse DNA-cytosine-5-methyltransferase: sequence specificity of the methylation reaction and electron microscopy of enzyme-DNA complexes, EMBO J. 4:2879–2884; Ward, C., et al., 1987, In vitro methylation of the 5'-flanking regions of the mouse b-globin gene, J. Biol. Chem. 262:11057–11063; Carotti, D., et al., 1986, Substrate preferences of the human placental DNA methyltransferase investigated with synthetic polydeoxynucleotides, Biochim. et Biophys. Acta. 866:135–143; Carotti D. et al., 1986, supra; Wang, R. Y. H., et al., 1984, Human placental DNA methyltransferase: DNA substrate and DNA binding specificity, Nucl. Acids Res. 12:3473–3490; Pfeifer et al., 1985, supra; Gruenbaum, Y., et al., 1982, Substrate and sequence specificity of a eukaryotic DNA methylase, Nature 295:620–622).

There is evidence that errors in the proper maintenance of genomic methylation are involved in aging and cancer. CpG islands are reported to become hypermethylated with age and may down-regulate expression of essential genes (Antequerra & Bird, 1993, Number of CpG islands and genes in human and mouse, Proceedings of the National Academy of Sciences, USA, 90:11995–11999; Nyce, J. W., 1997, Drug-induced DNA hypermethylation: A potential mediator of acquired drug resistance during cancer chemotherapy, Mutation Research 386:153–161) Amplification of DCMTase expression by an exogenous mammalian DCMTase gene induces tumorigenic transformation of NIH 3T3 mouse fibroblasts (Wu et al., 1993, Expression of an exogenous eukaryotic DNA methyltransferase gene induces transformation of NIH 3T3 cells, Proc. Natl. Acad. Sci., USA, 90:8891–8895). Human neoplastic cells and cells derived from different stages of colon cancer express up to 200-fold higher levels of DCMTase than normal (El-Deiry et al., 1991, High expression of the DNA methyltransferase-gene characterizes human neoplastic cells and progression stages of colon cancer, Proc. Natl. Acad. Sci., USA, 88:3470–3474). This contributes substantially to tumor development in a mouse model of intestinal neoplasia (Laird, P. W., et al., 1995, Suppression of intestinal neoplasia by DNA hypomethylation, Cell 81:197–205). Changes in DNA methylation and DCMTase activity appear early in oncogenesis (Belinsky, S. A., et al., 1996, Increased cytosine DNA-methyltransferase activity is target-cell-specific and an early event in lung cancer, Proc. Natl. Acad. Sci. USA 93:4045–4050).

Conversely, antisense oligonucleotides that interfere with expression of DCMTase may inhibit tumorigenesis (Ramachandani et al., 1997, Inhibition of tumorigenesis by a cytosine-DNA methyltransferase, antisense oligonucleotide, Proc. Natl. Acad. Sci., USA, 94:684–689; MacLeod & Szyf, 1995, Expression of antisense to DNA methyltransferase mRNA induces DNA demethylation and inhibits tumorigenesis, J. Biol. Chem. 270:8037–8043). The anticancer agent 5-aza-deoxycytidine functions by inhibiting the DCMTase (Jones, 1985, Altering gene expression with 5-azacytidine, Cell 40:485–486; Jutterman et al., 1994, Toxicity of 5-aza-2'-deoxycytidine to mammalian cells is mediated primarily by covalent trapping of DNA methyltransferase rather than DNA demethylation, Proc. Natl. Acad. Sci., USA, 91:11797–11801). Changes in DNA methylation and DCMTase activity early in oncogenesis (Belinsky, S. A., et al., 1996, supra) and the ability of DCMTase inhibitors to virtually abolish adenoma formation in mice (Laird, P. W., et al., 1995, supra) suggest that DCMTase inhibitors might be useful anticancer therapeutics (Szyf, M., 1996, The DNA methylation machinery as a target for anticancer therapy, Pharmacol. Ther. 70:1–37). 5-Aza-deoxycytidine is an irreversible, mechanism-based DCMTase inhibitor that has been used in patients with acute myeloid leukemia. Unfortunately, 5-Aza-deoxycytidine is unstable in solution and may be carcinogenic as well as mutagenic (Jones, P. A., 1996, DNA methylation errors and cancer, Cancer Res. 56:2463–2467). There is a need for DCMTase inhibitors that do not require incorporation into DNA and that are mechanistically unlike 5-aza-deoxycytidine (Belinsky, S. A., et al., 1996, supra; Szyf, M., 1996, supra; Jones, 1996, supra). A keen understanding of how DCMTase functions in vitro can be the basis for better strategies to both activate and inhibit the enzyme to correct developmental disorders like cancer.

Enzymes that catalyze one carbon additions to $C^5$ of pyrimidines define a class of enzymes with similar chemistry (Ivanetich, K. M., & Santi, D. V., 1992, 5,6-Dihydropyrimidine adducts in the reactions and interactions of pyrimidines with proteins, Prog. Nucleic Acid Res. Mol. Biol. 42:127–156). The bacterial DNA cytosine $C^5$ methyltransferase, M.HhaI (38 kDa Mr), modifies the internal cytosine in GCGC and has an ordered Bi Bi kinetic mechanism in which DNA binds first (Wu, J. C., & Santi, D. V., 1987, Kinetic and catalytic mechanism of HhaI methyltransferase, J. Biol. Chem. 262:4778–4786). Catalysis involves nucleophilic attack of an active site cysteine at the $C^6$ position of the cytosine which, in the absence of the cofactor, leads to exchange of the $C^5$ hydrogen. A M.HhaI-DNA cocrystal structure suggests that a catalytic intermediate exists that involves the translocation of the target cytosine to an extrahelical position covalently-bound to an active site cysteine (Klimasauskas, S., et al., 1994. HhaI methyltransferase flips its target base out of the DNA helix, Cell 76:357–369). Methyl transfer from AdoMet is followed by β-elimination to regenerate the active enzyme (Wu & Santi, 1987, supra; Osterman, D. G., et al., 1988, 5-Fluorocytosine in DNA is a mechanism-based inhibitor of HhaI methylase, Biochemistry 27:5204–5210).

A recent kinetic study of a highly homogeneous, unproteolyzed preparation of DCMTase from mouse erythroleukemia cells (MEL) further characterized the interactions of the enzyme with DNA and AdoMet (Flynn, J., et al., 1996, Murine DNA cytosine-C5 methyltransferase: Pre-steady- and steady-state kinetic analyses with regulatory DNA sequences, Biochemistry 35:7308–7315). The invention disclosed herein descriptively accounts for the previously reported complexities in kinetic behavior and identifies a potent single-stranded oligonucleotide inhibitor that binds to the enzyme at a distinct regulatory site.

There is a need for molecules which modulate the methylation of DNA for the reasons discussed above. In addition, molecules which inhibit DNA methylation can be useful for preventing drug resistance acquired by subjects undergoing cancer chemotherapy.

Drug-induced DNA hypermethylation is regarded as a potential mediator of this acquired drug resistance (Nyce, J. W., 1997, Drug-induced DNA hypermethylation: A potential mediator of acquired drug resistance during cancer chemotherapy, Mutation Research 386:153–161).

SUMMARY OF THE INVENTION

The invention provides synthetic oligonucleotides comprising a C-5 methylcytosine. The oligonucleotide recognizes and binds an allosteric site on DNA methyltransferase thereby inhibiting DNA methyltransferase activity. In one embodiment, the synthetic oligonucleotide has an inhibition constant of not greater than 1000 nM. In another embodiment, the synthetic oligonucleotide has an inhibition constant of not greater than 200 nM. In yet another embodiment, the synthetic oligonucleotide has an inhibition constant of not greater than 20 nM.

The invention further provides a composition comprising a synthetic oligonucleotide comprising a C-5 methylcytosine and which recognizes and binds an allosteric site on DNA methyltransferase. The composition is useful for inhibiting DNA methyltransferase activity, thereby inhibiting the methylation of DNA. In one embodiment, the composition is a pharmaceutical composition comprising a pharmaceutically effective amount of a synthetic oligonucleotide comprising a C-5 methylcytosine and which recognizes and binds an allosteric site on DNA methyltransferase, and optionally, a pharmaceutically acceptable carrier. The pharmaceutical composition is useful for treating disorders associated with methylation defects, such as cancer and certain developmental disorders.

The invention further provides a method of inhibiting methylation of DNA. The method involves contacting a DCMTase with a synthetic oligonucleotide which recognizes and binds an allosteric site on DNA methyltransferase thereby resulting in a DNA methyltransferase/synthetic oligonucleotide complex. The complex is contacted with the DNA. The presence of the complex prevents binding of AdoMet to DNA methyltransferase in a catalytically competent manner thereby inhibiting DNA methyltransferase activity and inhibiting methylation of DNA. In one embodiment, the synthetic oligonucleotide comprises a C-5 methylcytosine.

The invention further provides a method of treating a disorder of cell proliferation or development. The method involves administering to a subject a synthetic oligonucleotide which recognizes and binds an allosteric site on DNA methyltransferase. The binding of the synthetic oligonucleotide prevents binding of AdoMet to DNA methyltransferase in a catalytically competent manner thereby inhibiting DNA methyltransferase. The inhibition of DNA methyltransferase prevents the methylation of DNA thereby treating the disorder of cell proliferation or development. In one embodiment, the synthetic oligonucleotide comprises a C-5 methylcytosine. In one embodiment, the disorder of cell proliferation is cancer such as lung cancer, breast cancer, prostate cancer, pancreatic cancer or colon cancer.

The invention also provides a method of identifying a modulator of DCMTase which recognizes and binds an allosteric site on DCMTase. The method comprises contacting a molecule with DCMTase in the presence of AdoMet and DNA. The method further comprises measuring DCMTase activity. An increase or decrease in DCMTase activity is indicative of a modulator of DCMTase activity. In one embodiment, the modulator is an inhibitor. In another embodiment, the modulator is an activator.

BRIEF DESCRIPTION OF THE FIGURES

FIG. 1A shows six synthetic oligonucleotides that mimic the GC-box and the cyclic AMP responsive elements (CRE) (SEQ ID NOS:9–12). The appropriate consensus is in bold type and the single, centrally located CpG dinucleotide is underlined (mC=C-5 methylcytosine). The complementary a, aMET, b, and bMET strands were annealed to produce unmethylated, a/b, and hemi-methylated, aMET/b or a/bMET, double-stranded substrates.

FIG. 1B shows oligonucleotide sequences corresponding to SEQ ID NOS:10, 11, 13, 14 and 15, as indicated, which were tested for inhibition in an in vitro assay. GC-box pMET has a phosphorothioate backbone, while the others have a deoxyribose backbone. $K_{ii}$ is the inhibition constant derived from the y-intercept values from double reciprocal plots and is a characteristic of the inhibitor binding to the allosteric site of the enzyme. $IC_{50}$ is the concentration of inhibitor that produces 50% activity of an uninhibited reaction.

FIG. 6 shows a randomized DNA substrate used in in vitro screening (SEQ ID NOS: 16–17). The top strand shown was synthesized using b-cyanoethyl phosphoramidite chemistry. The PCR primers used for amplifying the shifted DNA are underlined. Primer C is underlined and contains an EcoRI restriction site. Primer D, underlined twice, contains a BamHI restriction site and was annealed to the randomized top strand for extension by Klenow polymerase The randomized positions are denoted as N and are either dG, dA or dT on one strand and the complementary dC, dA or dT on the other strand of the duplex.

FIG. 7 shows cloned and sequenced individual isolates from the pooled generations (SEQ ID NOS:18–100 respectively). Only the guanine containing strand is shown for simplicity. Generation-5 members are arranged with the highest guanine content on the 5' side of the invariant CpG at the top. Frequency information is given for each randomized flank on the appropriate border, an asterisk denotes a single occurrence.

FIG. 8A shows the nucleotide frequency at each randomized flanking position for the generation-5 screening in the form of a bar graph indicating the percent occurrence of each nucleotide at the randomized positions. The predominance of guanosine extends over the entire randomized region. The horizontal line at 33% is representative of the starting pool frequencies. The line at 70% is added as a visual aid.

FIG. 8B lists the nucleotide percentages at each randomized position for the generation-5 screening.

FIG. 9 shows genomic sequences similar to the DCMTase selected generation-5 clones (SEQ ID NOS 101–110). Fasta searches through the mouse and human GenBank libraries produced these matches when limited to no greater than four mismatches and no gaps. The definitions have been edited from the original entries.

DETAILED DESCRIPTION OF THE INVENTION

Figure 2:
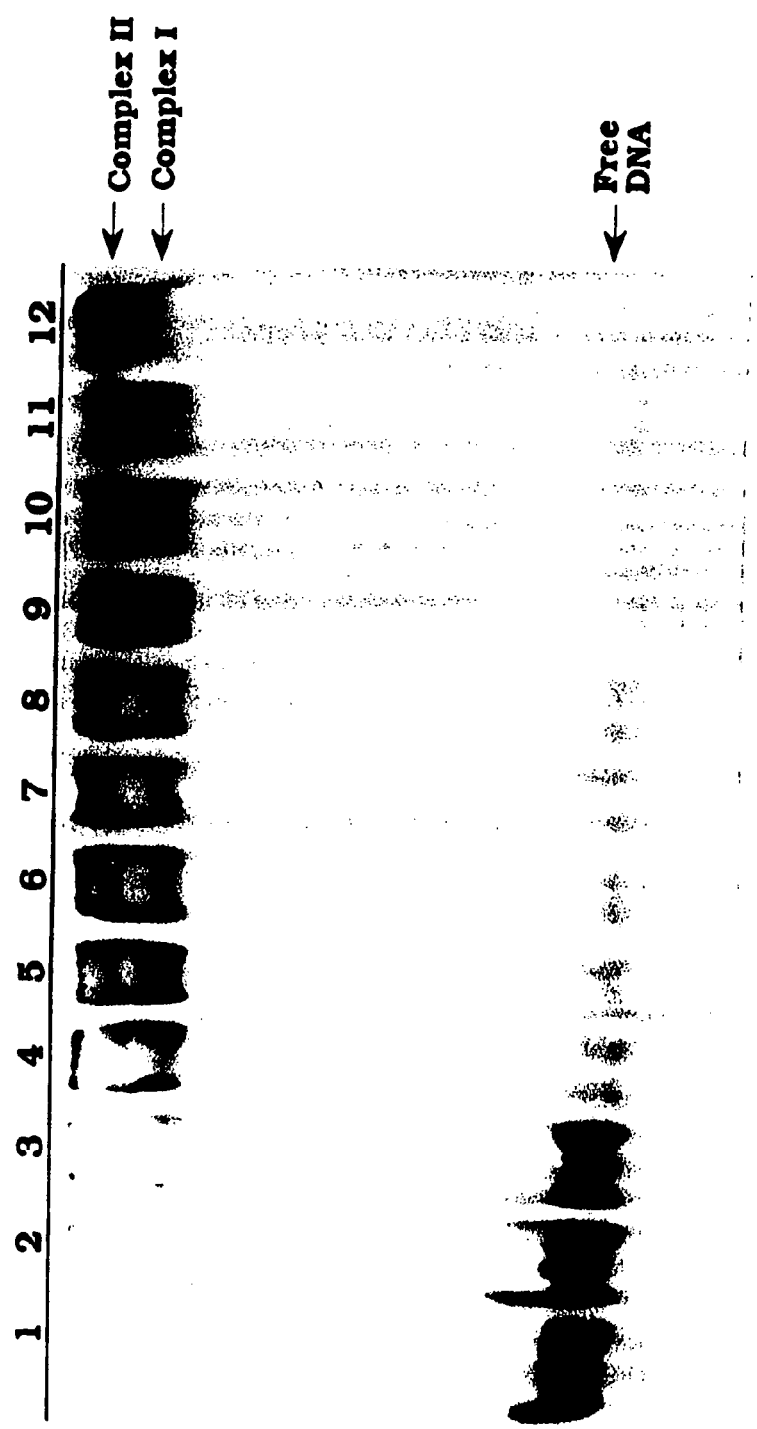
FIG. 2 is an autoradiogram showing the results of gel mobility shift analysis varying DCMTase with constant GC-box a/b. Lane 1: 0 nM DCMTase; Lane 2: 5.0 nM DCMTase; Lane 3: 10 nM DCMTase; Lane 4: 20 nM DCMTase; Lane 5: 30 nM DCMTase; Lane 6: 35 nM DCMTase; Lane 7: 40 nM DCMTase; Lane 8: 45 nM DCMTase; Lane 9: 50 nM DCMTase; Lane 10: 65 nM DCMTase; Lane 11: 75 nM DCMTase; Lane 12: 95 nM DCMTase.

The invention provides a synthetic oligonucleotide comprising a C-5 methylcytosine and which recognizes and binds an allosteric site on DNA cytosine methyltransferase thereby modulating DCMTase activity associated with the allosteric site. In one embodiment, the modulating comprises inhibition. In another embodiment, the modulating comprises activation. The C-5 methylcytosine of the synthetic oligonucleotide can be present as a 5mCpG dinucleotide.

In one embodiment, the DCMTase is from a mammal, bird, fish, amphibian, reptile, insect, plant, bacterium, virus or fungus. The mammal can be selected from the group consisting of mouse and human.

In one embodiment, the synthetic oligonucleotide comprises a nucleotide sequence as shown in FIG. 1B and designated GC-box $b^{MET}$ (SEQ ID NO:10), GC-box $p^{MET}$ (SEQ ID NO:10), GC-box $c^{MET}$ (SEQ ID NO:13), GC-box $d^{MET}$ (SEQ ID NO:14), GC-box $e^{MET}$ (SEQ ID NO:15), or CRE $a^{MET}$ (SEQ ID NO:11). In one embodiment, the synthetic oligonucleotide has an inhibition constant of not greater than 1000 nM by steady-state kinetic assay. In another embodiment, he synthetic oligonucleotide has an inhibition constant of not greater than 200 nM by steady-state kinetic assay. In yet another embodiment, the synthetic oligonucleotide has an inhibition constant of not greater than 20 nM by steady-state kinetic assay.

In accordance with the practice of the invention, the oligonucleotide can be DNA, RNA, or a derivative or hybrid thereof. The invention further provides a composition comprising a synthetic oligonucleotide comprising a C-5 methylcytosine and which recognizes and binds an allosteric site on DNA methyltransferase. The composition is useful for inhibiting DNA methyltransferase activity, thereby inhibiting the methylation of DNA. In one embodiment, the composition is a pharmaceutical composition comprising a pharmaceutically effective amount of a synthetic oligonucleotide comprising a C-5 methylcytosine, or a pharmaceutically acceptable salt thereof, and which recognizes and binds an allosteric site on DNA methyltransferase. In one embodiment, the pharmaceutical compositon further comprises a pharmaceutically acceptable carrier. The pharmaceutical composition is useful for treating disorders associated with methylation defects, such as cancer and certain developmental disorders.

The invention further provides a method of inhibiting methylation of DNA. The method involves contacting a DNA methyltransferase with a synthetic oligonucleotide which recognizes and binds an allosteric site on DNA methyltransferase thereby resulting in an enzyme/synthetic oligonucleotide complex. The presence of the complex prevents binding of AdoMet to DNA methyltransferase in a catalytically competent manner thereby inhibiting DNA methyltransferase activity and inhibiting methylation of DNA. In one embodiment, the enzyme/synthetic olignucleotide complex forms a further complex with DNA. In one embodiment, the synthetic oligonucleotide comprises a C-5 methylcytosine. In one embodiment, the C-5 methylcytosine is present as a 5mCpG dinucleotide.

The invention further provides a method of treating a disorder of cell proliferation or development. The method involves administering to a subject a synthetic inhibitor molecule which recognizes and binds an allosteric site on DNA methyltransferase. The binding of the synthetic inhibitor molecule prevents binding of AdoMet to DNA methyltransferase in a catalytically competent manner thereby inhibiting DNA methyltransferase. The inhibition of DNA methyltransferase prevents the methylation of DNA thereby treating the disorder of cell proliferation or development. In one embodiment, the synthetic oligonucleotide comprises a C-5 methylcytosine which recognizes and binds an allosteric site on DCMTase thereby inhibiting DNA methyltransferase activity. In one embodiment, the disorder of cell proliferation is cancer, such as lung cancer or colon cancer. In one embodiment, the disorder of development is one linked to a genetic locus regulated by methylation. Examples of such disorders include, but are not limited to, Huntington's disease, Down's syndrome, and disorders associated with a Hox gene.

The invention provides a method of inhibiting proliferation of cancer cells comprising administering to a subject a synthetic inhibitor molecule which recognizes and binds an allosteric site on DCMTase thereby resulting in an enzyme/synthetic inhibitor molecule complex, inhibiting DCMTase-mediated methylation of DNA, and thereby inhibiting proliferation of the cancer cells. In one embodiment, the cancer cell is from lung or colon. In one embodiment, the synthetic inhibitor molecule is an oligonucleotide comprising a C-5 methylcytosine which recognizes and binds an allosteric site on DCMTase thereby inhibiting DNA methyltransferase activity. In one embodiment, the C-5 methylcytosine is present as a 5mCpG dinucleotide. In one embodiment, the synthetic oligonucleotide comprises a nucleotide sequence as shown in FIG. 1B and designated GC-box $b^{MET}$ (SEQ ID NO:10), GC-box $P^{MET}$ (SEQ ID NO:10), GC-box $c^{MET}$ (SEQ ID NO:13), GC-box $d^{MET}$ (SEQ ID NO:14), GC-box $e^{MET}$ (SEQ ID NO:15), or CRE $a^{MET}$ (SEQ ID NO:11). In one embodiment, the subject is a human. In another embodiment, the subject is an animal. In one embodiment, the animal is selected from a group consisting of porcine, piscine, avian, feline, equine, bovine, ovine, caprine and canine.

Definitions

All scientific and technical terms used in this application have meanings commonly used in the art unless otherwise specified. As used in this application, the following words or phrases have the meanings specified.

As used herein "synthetic oligonucleotide comprising a C-5 methylcytosine" means any non-naturally occurring oligonucleotide comprising a C-5 methylcytosine. The oligonucleotide can be a RNA, DNA or a derivative or hybrid thereof. The C-5 methylcytosine can be in the form of a 5mCpG dinucleotide. In one embodiment, the C-5 methylcytosine is centrally located within the oligonucleotide. In one embodiment, the synthetic oligonucleotide of the invention can be approximately 5 to approximately 70 bases in length. In another embodiment, the synthetic oligonucleotide can be approximately 15 to approximately 50 bases in length. In another embodiment, the synthetic oligonucleotide can be approximately 20 to approximately 30 bases in length. In another embodiment, the synthetic oligonucleotide is approximately 30 bases in length. Examples of synthetic oligonucleotides of the invention include, but are not limited to, the oligonucleotides GC-box $b^{MET}$ (SEQ ID NO:10), GC-box $p^{MET}$ (SEQ ID NO:10), GC-box $c^{MET}$ (SEQ ID NO:13), GC-box $d^{MET}$ (SEQ ID NO:14), GC-box $e^{MET}$ (SEQ ID NO:15), and CRE $a^{MET}$ (SEQ ID NO:11) shown in FIG. 1B.

As used herein, "synthetic inhibitor molecule" includes synthetic molecules known in the art to facilitate entry of nucleic acids into cells and to minimize intracellular and intercellular breakdown of the nucleic acids. Examples of such antisense molecules include, but are not limited to, peptide nucleic acid (PNA) and phosphorothioate-based molecules such as deoxyribonucleic guanidine (DNG) or ribonucleic guanidine (RNG). Also included are normucleic acid polymers derived from a library screen which bind the same site as the synthetic oligonucleotide of the invention.

As used herein, "an allosteric site" means a site other than an active site that can influence the catalytic progress of the enzyme. The influence can either inhibit or activate catalysis. For example, an active site on DCMTase includes the site to which AdoMet binds, the binding of AdoMet to the active site on DCMTase leading to the methylation of DNA. An active site is defined as the local protein environment in close proximity to the reactive substituents in the methylation reaction.

As used herein, "DNA methyltransferase activity" means enzymatic activity that promotes transfer of a methyl group to DNA, thereby methylating DNA. An example of a source of a methyl group for transfer to DNA is AdoMet.

As used herein, "pharmaceutically acceptable salt" refers to a salt that retains the desired biological activity of the parent compound and does not impart any undesired toxicological effects. Examples of such salts include, but are not limited to, (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, furmaric acid, gluconic acid, citric acid, malic acid, ascorbic acid, benzoic acid, tannic acid, pamoic acid, alginic acid, polyglutamic acid, naphthalenesulfonic acids, naphthalenedisulfonic acids, polygalacturonic acid; (b) salts with polyvalent metal cations such as zinc, calcium, bismuth, barium, magnesium, aluminum, copper, cobalt, nickel, cadmium, and the like; or (c) salts formed with an organic cation formed from N,N'-dibenzylethylenediamine or ethylenediamine; or (d) combinations of (a) and (b) or (c), e.g., a zinc tannate salt; and the like. The preferred acid addition salts are the trifluoroacetate salt and the acetate salt.

As used herein, "pharmaceutically acceptable carrier" includes any material which, when combined with a compound of the invention, allows the compound to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline. Compositions comprising such carriers are formulated by well known conventional methods (see, for example, Remington's Pharmaceutical Sciences, Chapter 43, 14th Ed., Mack Publishing Co., Easton Pa. 18042, USA).

Compounds of the Invention

The invention provides a synthetic oligonucleotide comprising a C-5 methylcytosine and which recognizes and binds an allosteric site on DNA methyltransferase thereby inhibiting DNA methyltransferase activity. In one embodiment, the synthetic oligonucleotide has an inhibition constant of not greater than 1000 nM by steady-state kinetic assay. In another embodiment, the synthetic oligonucleotide has an inhibition constant of not greater than 200 nM by steady-state kinetic assay. In yet another embodiment, the synthetic oligonucleotide has an inhibition constant of not greater than 20 nM by steady-state kinetic assay. In one embodiment, the C-5 methylcytosine is centrally located within the oligonucleotide. In one embodiment, the synthetic oligonucleotide of the invention can be approximately 5 to approximately 70 bases in length. In another embodiment, the synthetic oligonucleotide can be approximately 15 to approximately 50 bases in length. In another embodiment, the synthetic oligonucleotide can be approximately 20 to approximately 30 bases in length. In a further-embodiment, the synthetic oligonucleotide is approximately 30 bases in length. Examples of synthetic oligonucleotides of the invention include, but are not limited to, the oligonucleotides shown in FIG. 1B and designated GC-box $b^{MET}$ (SEQ ID NO:10), GC-box $p^{MET}$ (SEQ ID NO:10), GC-box $c^{MET}$ (SEQ ID NO:13), GC-box $d^{MET}$ (SEQ ID NO:14), GC-box $e^{MET}$ (SEQ ID NO:15), or CRE $a^{MET}$ (SEQ ID NO:11).

Compositions Of The Invention

The invention further provides a composition comprising a synthetic oligonucleotide comprising a C-5 methylcytosine and which recognizes and binds an allosteric site on DNA methyltransferase. The composition is useful for inhibiting DNA methyltransferase activity, thereby inhibiting the methylation of DNA. In one embodiment, the composition is a pharmaceutical composition comprising a pharmaceutically effective amount of a synthetic oligonucleotide comprising a C-5 methylcytosine, or a pharmaceutically acceptable salt thereof, and which recognizes and binds an allosteric site on DNA methyltransferase. In one embodiment, the pharmaceutical compositon further comprises a pharmaceutically acceptable carrier. The pharmaceutical composition is useful for treating disorders associated with methylation defects, such as cancer and certain developmental disorders.

Administration of the Compositions

In accordance with the methods of the invention, the synthetic oligonucleotide can be administered in a pharmaceutical composition in unit dosage form. The most effective mode of administration and dosage regimen for the molecules of the present invention depend upon the location of the tissue or disease being treated, the severity and course of the medical disorder, the subject's health and response to treatment and the judgment of the treating physician. Accordingly, the dosages of the molecules should be titrated to the individual subject.

By way of example, the interrelationship of dosages for animals of various sizes and species and for humans based on mg/m$^2$ of surface area is described by Freireich, E. J., et al. Cancer Chemother., Rep. 50 (4): 219–244 (1966). It would be clear that the dose of the composition of the invention required to achieve an appropriate clinical outcome may be further reduced with schedule optimization.

Methods of the Invention

The invention further provides a method of inhibiting methylation of DNA. The method involves contacting a DCMTase with a synthetic inhibitor molecule in the presence of the DNA. The synthetic inhibitor molecule comprises a C-5 methylcytosine which recognizes and binds an allosteric site on DNA cytosine methyltransferase (DCMTase) thereby resulting in an enzyme/synthetic inhibitor molecule complex. The presence of the complex prevents DCMTase-mediated catalysis thereby inhibiting DCMTase activity and inhibiting methylation of DNA. In one embodiment, the synthetic oligonucleotide comprises a C-5 methylcytosine. In a further embodiment, the C-5 methylcytosine is present as a 5mCpG dinucleotide. Examples of synthetic inhibitor molecules include, but are not limited to, the oligonucleotides shown in FIG. 1B and designated GC-box $b^{MET}$ (SEQ ID NO:10), GC-box $p^{MET}$ (SEQ ID NO:10), GC-box $c^{MET}$ (SEQ ID NO:13), GC-box $d^{MET}$ (SEQ ID NO:14), GC-box $e^{MET}$ (SEQ ID NO:15), or CRE $a^{MET}$ (SEQ ID NO:11).

The invention further provides a method of treating a disorder of cell proliferation or development. The method involves administering to a subject a synthetic oligonucleotide which recognizes and binds an allosteric site on DCMTase. The binding of the synthetic oligonucleotide prevents DCMTase-mediated catalysis thereby inhibiting DCMTase activity. The inhibition of DCMTase prevents the methylation of DNA thereby treating the disorder of cell proliferation or development. In one embodiment, the synthetic oligonucleotide comprises a C-5 methylcytosine. In one embodiment, the disorder of cell proliferation is cancer, such as lung cancer or colon cancer. In another embodiment, the disorder of development is one linked to a genetic locus regulated by methylation. Examples of such disorders include, but are not limited to, Huntington's disease, Down's syndrome, and disorders associated with a Hox gene.

The invention provides a method of inhibiting proliferation of cancer cells comprising administering to a subject a synthetic inhibitor molecule which recognizes and binds an allosteric site on DCMTase thereby resulting in an enzyme/synthetic inhibitor molecule complex. The presence of the complex prevents DCMTase catalysis thereby inhibiting DCMTase-mediated methylation of DNA, thereby inhibiting proliferation of the cancer cells. In one embodiment, the synthetic inhibitor molecule is an oligonucleotide comprising a C-5 methylcytosine which recognizes and binds an allosteric site on DCMTase thereby inhibiting DNA methyltransferase activity. In one embodiment, the cancer is lung cancer or colon cancer. In one embodiment, the method of inhibiting proliferation of cancer cells comprises administering to a subject the synthetic oligonucleotide of the invention in a sufficient amount so that the oligonucleotide recognizes and binds an allosteric site on DCMTase so as to form an enzyme/synthetic oligonucleotide complex.

The invention provides a method of inhibiting hypermethylation of DNA comprising contacting a DNA cytosine methyltransferase (DCMTase) with a synthetic inhibitor molecule comprising a C-5 methylcytosine which recognizes and binds an allosteric site on DCMTase thereby resulting in an enzyme/synthetic inhibitor molecule complex, in the presence of the DNA. The presence of the complex prevents DCMTase catalysis thereby inhibiting DCMTase activity and inhibiting hypermethylation of the DNA. In one embodiment, the synthetic oligonucleotide comprises a C-5 methylcytosine. In a further embodiment, the C-5 methylcytosine is present as a 5mCpG dinucleotide. The inhibition of hypermethylation of DNA is useful for preventing the development of resistance to drugs such as anti-cancer drugs.

The invention provides a method of inhibiting drug resistance in a subject comprising administering to a subject the synthetic oligonucleotide of the invention in a sufficient amount so that the oligonucleotide recognizes and binds an allosteric site on DCMTase so as to form an enzyme/synthetic oligonucleotide complex. The presence of the complex prevents DCMTase catalysis so as to inhibit DCMTase-mediated hypermethylation of DNA thereby inhibiting drug resistance. The synthetic inhibitor molecule can be administered to a subject prior to, concurrent with or after administration of an anti-cancer therapeutic agent to prevent overmethylation of DNA induced in the subject's cells in response to the anti-cancer therapeutic agent.

The invention additionally provides a method for screening molecules, such as those obtained from a combinatorial library, to identify modulators of DCMTase which recognize and bind an allosteric site on DCMTase. In one embodiment, the modulator is an inhibitor of DCMTase. In another embodiment, the modulator is an activator of DCMTase. The method comprises contacting a molecule with DCMTase in the presence of AdoMet and DNA, and measuring DCMTase activity. An increase in DCMTase activity is indicative of an activator of DCMTase and a decrease in DCMTase activity is indicative of an inhibitor of DCMTase. DCMTase activity can be measured by methods known in the art, including the assays disclosed in the Examples provided herein. Those of ordinary skill in the art can identify a modulation of DCMTase activity that is indicative of binding an allosteric site on the enzyme. In a preferred embodiment, DCMTase activity is measured by a steady-state assay. One can plot enzyme activity as a function of varied concentrations of the molecule being tested, and also as a function of varied concentrations of DNA and AdoMet. Preferably, a mathematical fit is performed on the plotted results. Competitive inhibition by DNA and uncompetitive inhibition by AdoMet, or competitive inhibition by AdoMet and uncompetitive inhibition by DNA, for example, would be indicative of an inhibitor molecule which recognizes and binds an allosteric site on DCMTase. Also included within the invention are modulators of DCMTase which recognize and bind an allosteric site on DCMTase, and which are identified by the above method.

Advantages of the Invention

The invention disclosed herein provides a potent and reversible inhibitor of DNA methyltransferase that does not require incorporation into DNA. This inhibitor can be used to inhibit methylation of DNA and to treat disorders associated with DNA methylation defects, such as cancer and developmental disorders.

In addition to identifying particular synthetic oligonucleotides which inhibit DNA methyltransferase, the invention provides information about the mechanism responsible for this inhibition. By identifying an allosteric site on DCMTase as the site of action of the inhibitors, the invention provides a basis for developing and identifying variants of the particular synthetic oligonucleotides disclosed herein that will also be useful for inhibiting DNA methyltransferase. Additionally, the disclosure herein teaches that a C-5 methylcytosine is responsible for the potency of the inhibition effected by the synthetic oligonucleotides of the invention.

EXAMPLES

The following examples are presented to illustrate the present invention and to assist one of ordinary skill in making and using the same. The examples are not intended in any way to otherwise limit the scope of the invention.

Example 1

DNA Binding Discrimination of the Murine DNA Cytosine-$C^5$ Methyltransferase

In this example gel mobility shift analyses (GMSA) using defined sequences to estimate $K_D^{DNA}$ and in vitro screening method of a large, divergent pool of DNA, are used to determine discrimination of DCMTase. The results presented herein demonstrate that the DCMTase:DNA complex is concluded to be thermodynamically stabilized by guanosine/cytosine-rich sequences flanking a central CpG cognate site.

Materials

DCMTase was purified from mouse erythroleukemia cells as previously described (Xu, G., et al. (1995) Biochemi. Biophysi. Res. Communi. 207:544–551). S-adenosyl-L-[methyl-$^3$H]methionine (75 Ci/mmol, 1 mCi/ml, 1 Ci=37 GBq) was from Amersham Life Sciences (Arlington Heights, Ill.), Unlabeled AdoMet, purchased from Sigma Chemical Company (St. Louis, Mo.), was further purified as described (Reich, N. O. & Mashhoon, N. (1990) Inhibition of EcoRI DNA methylase with cofactor analogs. J. Biol. Chem. 265:8966–8970). Routinely, a 125 mM AdoMet stock concentration was prepared at a specific activity of 5.8×10$^3$ cpm/pmol. DE81 filters were purchased from Whatman Inc. (Lexington, Mass.). All other chemicals and reagents were purchased from Sigma Chemical Company (St. Louis, Mo.) or Fisher Scientific (Hampton, N. H.).

DNA Substrate Preparation

The preparation, purification, and analysis of six oligonucleotides that mimic the GC-box and the cyclic AMP responsive elements (CRE) were previously described (Flynn, J., et al., 1996, Murine DNA cytosine-C5 methyltransferase: Pre-steady and steady-state kinetic analyses with regulatory DNA sequences, Biochemistry 35:7308–7315) (FIG. 1). The percentage of double-stranded DNA in annealed DNA samples was confirmed to be greater than 99% by $^{32}$P-radiolabeling, polyacrylamide gel separation, subsequent autoradiography and densitometry using a CCD camera and the SW5000 analysis package from Ultra Violet Products (UVP, San Gabriel, Calif.).

Gel Mobility Shift Assays

Gel mobility shift assays (GMSA) were performed with minor revisions to the original procedures (Fried, M., & Crothers, D. M., 1981, Equilibria and kinetics of the lac repressor-operator interactions by polyacrylamide gel electrophoresis, Nucleic Acids Res. 9:6505–6525; Garner, M. M. & Revzin, A., 1981, A gel electrophoresis method for quantifying the binding proteins to specific DNA regions: applications to components of the *Escherichia coli* lactose operon regulatory system, Nucleic Acids Res. 13:3047–3060). All reactions were done in 100 mM Hepes pH 7.4, 10 mM EDTA, 10 mM DTT, 200 mg/ml BSA, 5% glycerol using the indicated P-labeled DNA and DCMTase concentrations, incubated on ice for 5 minutes and loaded on a 1xTBE (89 mM Tris-HCl pH 8.3, 89 mM boric acid, 2 mM EDTA), 6% polyacrylamide gel. Electrophoresis was done at 250 V, 9 mA for 2 hours at 4° C. and the dried gel was exposed to film overnight. The reaction conditions for buffer, temperature, incubation time, cofactor addition and gel composition have all been optimized. Only slightly better complex resolution was obtained under the listed conditions compared to a 10 minute incubation at 37° C. prior to gel loading at room temperature and containing either cofactor S-adenosyl-L-methionine, product S-adenosyl-L-homocysteine, or the AdoMet analog sinefungin. Hepes reaction buffer at pH 7.4 produced sharper banding than Tris-HCl at pH 8.0. Initial binding assays, with a limiting, and constant DNA concentration, resulted in the formation of multiple bands. Subsequent assays used a limiting and constant enzyme concentration with varying DNA concentrations.

Binding Isotherm Determinations of $K_D^{DNA}$

Autoradiogram-derived band intensities corresponding to the mobility shifted DCMTase:DNA complexes were acquired using the UVP system described above. Background subtractions were from equivalent areas about one centimeter below each mobility shifted complex. The corrected intensities were then fit to a nonlinear binding isotherm and graphed using KaleidaGraph 2.1.2 software (Synergy Software, Reading, Pa.) The intensity of the labeled DNA in the protein:DNA complex at saturation was directly compared to uncomplexed DNA areas in control lanes containing 50%, 100% and 150% molar DNA equivalents of the DCMTase concentration.

Screening for DNA Binding Preferences

An in vitro selection approach was used to determine the DNA binding discrimination of DCMTase. A population of DNA molecules, each 66 base pairs long, were synthesized with a central CpG dinucleotide flanked on each side by 12 positions randomized with either adenosine, thymidine or cytidine; total complexity equal to $2.8 \times 10^{11}$ discrete sequences (FIG. 6). Guanosine was not added to the randomization to avoid multiple CpG dinucleotides on a double-stranded DNA. The randomized regions are flanked by PCR primer regions that contain the restriction sites used for cloning. The first generation pool of DNA was made double-stranded by Klenow polymerase extension of primer D.

The screening procedure was reiterated five times under the conditions listed in Table 2 (see Results, infra). DNA substrates from each pooled generation that induced higher thermodynamic stabilities of the DCMTase:DNA complex were separated from lower affinity DNA by PAGE as described above. The region of the gel containing shifted DNA complexes was excised and five exchanges of 5 mL water over 72 hours shaking on ice was sufficient to elute greater than 95% of all cpm present in the excised gel slice as determined by Cerenkov counting. The eluted DNA was lyophilized, resuspended in TE (10 mM Tris-HCl at pH 8.0; 1 mM EDTA) and cleaned by one phenol:chloroform and two chloroform extractions followed by ethanol precipitation and resuspension in TE. The selected DNA pools were amplified using 20 rounds of PCR using Deep Vent polymerase (New England Biolabs) and the DNA primers shown in FIG. 6. The 66 base pair DNA was separated from the PCR primers on agarose gels and purified using minor changes to the original procedure (Wieslander, L., 1979, A simple method to recover intact high molecular weight RNA and DNA after electrophoretic separation in low gelling temperature agarose gels, Anal. Biochem. 98:305–3).

Identification of Preferred DNA Substrates

Individual members from the selected DNA pools were identified by cleaving the DNA ends with BamHI and EcoRI endonuclease and cloning into pGEM11zf-(Promega, Madison, Wis.) using standard protocols. The plasmid DNA from single isolates was prepared and the selected CpG flanking sequences were determined using the CircumVent sequencing kit (New England Biolabs, Beverly, Mass.). The selected inserts were sequenced from both strands using the T7 and SP6 sequencing primers (Promega, Madison, Wis.). Statistical analyses were performed using several programs in the Wisconsin Sequence Analysis Package (Genetics Computer Group, Madison, Wis.) and Kaliedagraph (Synergy Software, Reading, Pa.). Statistical signficance was determined by the Student's t-Test using Microsoft Excel, Microsoft, Redmond, Wash.

The selected generations were analyzed for initial velocity. The 50 mL reactions contained 50 nM DCMTase, 7 mM AdoMet and DNA at 4.7, 23, 47 and 230 nM in 100 mM Tris pH 8.0, 10 mM EDTA, 10 mM DTT, 200 mg/mL BSA. AdoMet (S-adenosyl-L-[methyl-$^3$H]methionine ([methyl-3H]AdoMet) (75 Ci/mmol, 1mCi/ml, 1 Ci=37 Gbq) was purchased from Amersham (Arlington Heights, Ill.). The incubations were for 1 hour at 37° C.

DNA with tritiated C-5 cytosines, deposited by the DCMTase, were separated from the tritiated AdoMet by spotting the reaction on DE 81 filters (Whatman, Lexington, Mass.) followed by a series of 200 mL washes; three in 50 mM HK$_2$PO$_4$ and one each in 80% ethanol, 95% ethanol and ethyl ether. Dried filters were placed in 3 mL of LiquiScint (National Diagnostics, Atlanta, Ga.) and counted in a scintillation counter. Counts per minute were transformed to femtomoles of methyl groups deposited on DNA over the course of the reaction.

Results

Gel Mobility Shift Analyses of GC— Box and CRE cis-Elements

The preliminary experiments used a standard gel mobility shift assay in which a constant, low DNA concentration was titrated with higher protein concentrations. As shown in FIG. 2, essentially all of the GC-box alb (100 pM) binding occurred between 5 nM and 95 nM DCMTase. An initial complex was formed at the lower DCMTase concentrations and an abrupt shift of most of the free DNA is coincident with the formation of a second complex at about 20 nM DCMTase. Further addition of DCMTase resulted in the loss of the more mobile complex I in favor of a less mobile complex II. Similar results were observed for GC-box a/b$^{MET}$, CRE a/b, and CRE a$^{MET}$/b. The complexes shown in FIG. 2 contained the DCMTase, as addition of an antibody to DCMTase resulted in an increased shift of each complex. Coincubation of DCMTase and GC-box a/b with a 40-fold excess of unlabeled polydA:polydT, calculated on adinucleotide basis, did not disrupt the specific DCMTase:DNA complex.

The multiple banding of DCMTase:DNA complexes observed in FIG. 2 are similar to results obtained with two cytosine DNA methyltransferases, M.MspI (Dubey, A. K. & Roberts, R. J., 1992, Sequence-specific DNA binding by the MspI DNA methyltransferase, Nucleic Acids. Res. 20:3167–3173) and M.HhaI (Mi, S. & Roberts, R. J., 1993, The DNA binding affinity of HhaI methylase is increased by a single amino acid substitution in the catalytic center, Nucleic Acids Res. 21:2459–2464; Reale et al., 1995, DNA binding and methyl transfer catalyzed by mouse DNA methyltransferase, Biochem. J. 312:855–861) obtained similar gel shift results with a mammalian DCMTase and assumed that the slower migrating band contained two DCMTase molecules bound to a single DNA.

Figure 3:
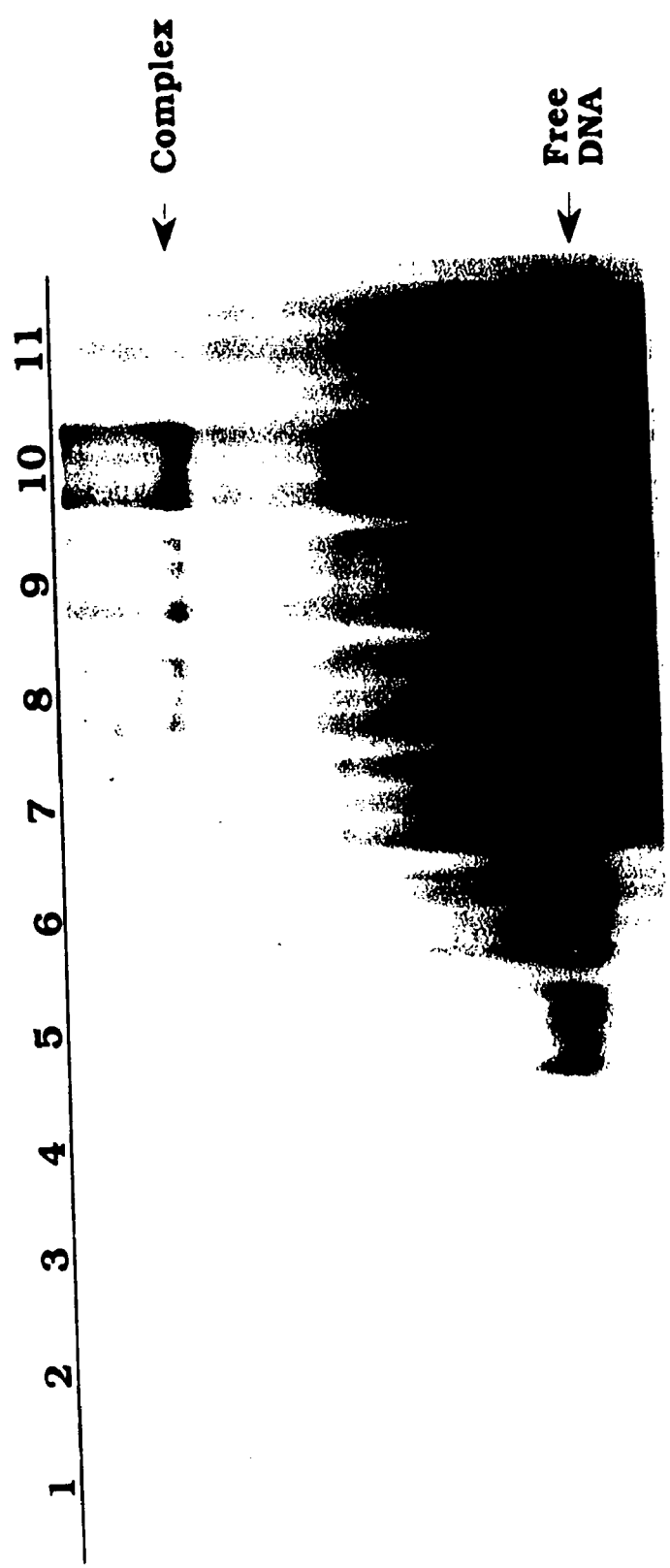
FIG. 3 is an autoradiogram showing the results of a gel mobility shift analysis varying GC-box a/b$^{MET}$ with constant DCMTase. Lane 1: 0.050 µM Free DNA; Lane 2: 0.10 µM Free DNA; Lane 3: 0.15 µM Free DNA; Lane 4: 0.10 µM DNA; Lane 5: 0.28 µM DNA; Lane 6: 0.45 µM DNA; Lane 7: 0.63 µM DNA; Lane 8: 0.80 µM DNA; Lane 9: 1.0 µM DNA; Lane 10: 2.0 µM DNA; Lane 11: 2.0 µM Free DNA. Lanes 1, 2, 3, and 11 are control experiments without added DCMTase.
Figure 4:
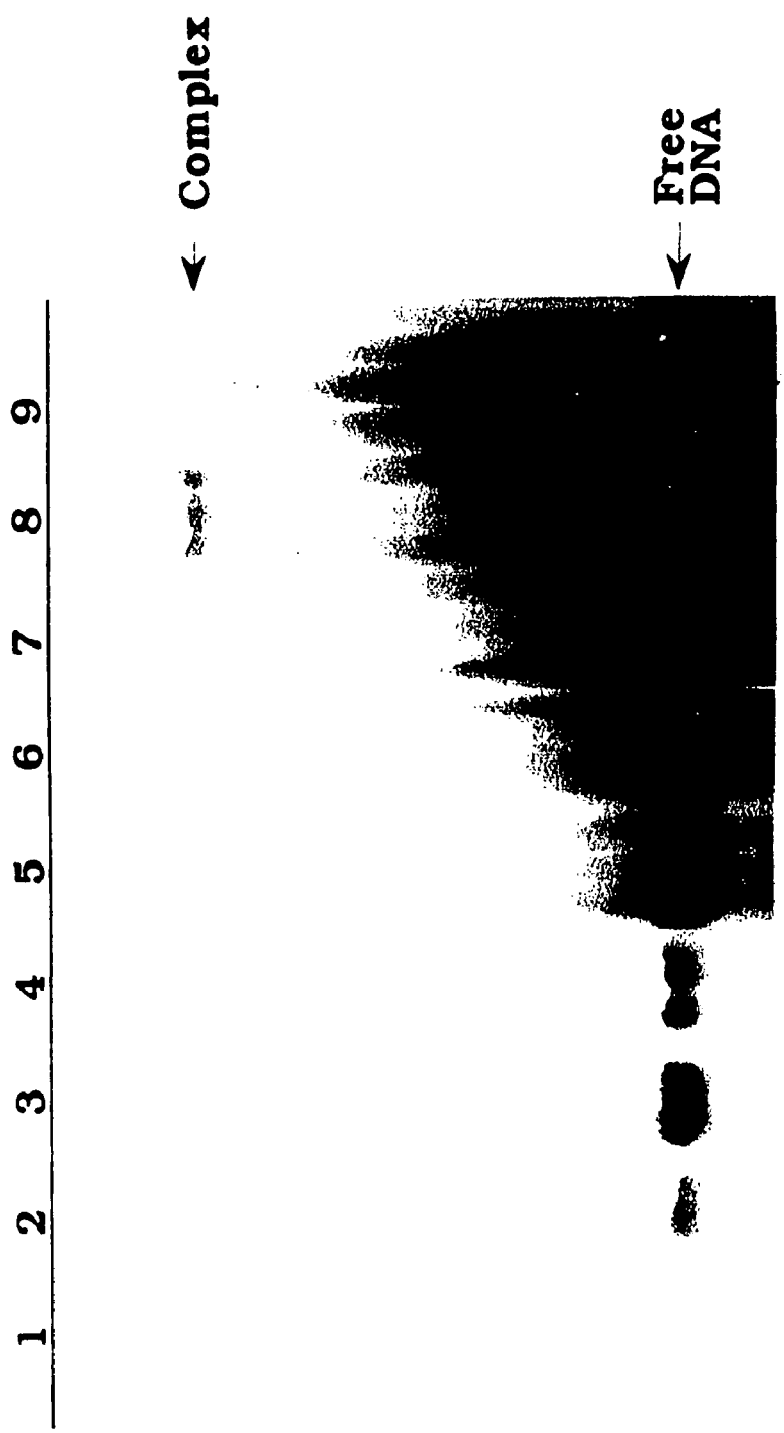
FIG. 4 is an autoradiogram showing the results of a gel mobility shift analysis varying GC-box a/b with constant DCMTase. Lane 1: 0.050 µM Free DNA; Lane 2: 0.10 µM Free DNA; Lane 3: 0.15 µM Free DNA; Lane 4: 0.10 µM DNA; Lane 5: 0.50 µM DNA; Lane 6: 1.0 µM DNA; Lane 7:4.0 µM DNA; Lane 8: 6.0 µM DNA; Lane 9: 6.0 µM Free DNA. Lanes 1, 2, 3, and 9 are control experiments without added DCMTase.
Figure 5:
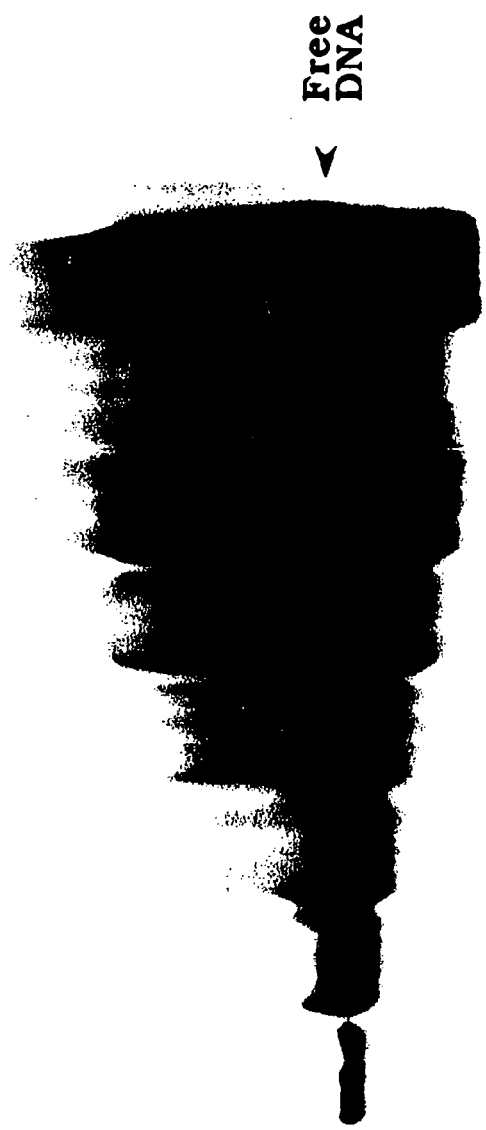
FIG. 5 is an autoradiogram showing the results of a gel mobility shift analysis varying GC-box b$^{MET}$ with constant DCMTase. Lane 1: 0.10 µM Free DNA; Lane 2: 0.20 µM DNA; Lane 3: 0.40 µM DNA; Lane 4: 0.80 µM DNA; Lane 5: 1.6 µM DNA; Lane 6: 3.2 µM DNA; Lane 7: 6.4 µM DNA; Lane 8: 3.2 µM DNA; Lane 9: 6.0 µM CRE a$^{MET}$/b. Lanes 1 and 8 are control experiments without added DCMTase.

Steady-state kinetic analyses of the DCMTase with the same 30 base-pair DNA substrates used in these studies indicate that K$_m^{DNA}$ is 1000- to 50,000-fold higher (Flynn, J., et al., 1996, Murine DNA cytosine-C5 methyltransferase: Pre-steady- and steady-state kinetic analyses with regulatory DNA sequences, Biochemistry 35:7308–7315) than the DNA concentrations used to generate FIG. 2 and used by Reale et al, 1995, supra. The complexes formed in FIG. 2 under limiting DNA and excess protein do not promote a detectable catalytic activity. Therefore, the stability of protein:DNA was determined by keeping the enzyme at a constant concentration (100 nM) and varying the amount of added DNA (Dubey & Roberts, 1992, supra). FIGS. 3 through 5 show the results with this approach for GC-box a/b$^{MET}$, GC-box a/b and GC-box b$^{MET}$. In all cases a single shifted band is resolved, the binding isotherm data are fit well by a simple hyperbola, and each complex is saturable. The apparent K$_D^{DNA}$ estimations for the different forms of GC-box and CRE are summarized in Table 1. The formation of equimolar protein:DNA complexes is supported by comparisons of the band intensity for complexed DNA at saturation with the band intensities of control reactions containing 50, 100 and 150 nM DNA and no enzyme (FIGS. 3 and 4, lanes 1, 2 and 3).

TABLE 1

Determinations of K$_D^{DNA}$ for DCMTase by Gel Mobility Shift Assay.[a]

| DNA Substrate | K$_D^{DNA}$ (mM) |
|---|---|
| GC-box a | 1.2 +/− 0.2 |
| GC-box b | 1.3 +/− 0.4 |
| GC-box b$^{MET}$ | 0.88 +/− 0.13 |
| GC-box a/b | 0.42 +/− 0.15 |
| GC-box a/b$^{MET}$ | 0.36 +/− 0.11 |
| CRE a | >50 |
| CRE b | >50 |
| CRE a/b | 1.5 +/− 0.4 |
| CRE a$^{MET}$/b | 1.0 +/− 0.3 |

[a]The values presented were obtained from the relative intensities of bands corresponding to DCMTase:DNA complexes fit by non-linear regression as described in Experimental Procedures.

DCMTase:DNA complexes formed by high substrate concentrations travel with the same relative mobility as complex I in FIG. 2. For DNA concentrations higher than about 10 times the apparent K$_D^{DNA}$, the complexes become less mobile. The complex formed between DCMTase and single-stranded GC-box b$^{MET}$ (FIG. 5, lane 7) is shown to migrate to approximately the same distance as the complex formed between DCMTase and hemi-methylated CRE a$^{MET}$/b DNA (lane 9).

The estimates of apparent K$_D^{DNA}$ are consistent with our previous K$_m^{DNA}$ estimates (Table 1 and Flynn, J., et al., 1996, Murine DNA cytosine-C5 methyltransferase: Pre-steady- and steady-state kinetic analyses with regulatory DNA sequences, Biochemistry 35:7308–7315). The hemi-methylated double-stranded form of DNA was bound with a slightly higher affinity than the unmethylated double-stranded form for both the GC-box and CRE DNA. In support of CpG flanking sequence discrimination by DCMTase, the GC-box substrates of each duplex form had an approximate three-fold lower K$_D^{DNA}$ than the corresponding CRE DNA form. Single-stranded substrates bound with less stability than double-stranded DNA. The binding of CRE single-strands was exceptionally poor and at the limits of resolution by this technique. GMSA was capable of resolving a binding discrimination in favor of guanosine/cytosine-rich sequences flanking a central CpG dideoxynucleotide.

Screening for DCMTase Binding Discrimination with a Randomized DNA Pool

The sampling of several discrete sequences for binding specificity is laborious and prone to investigative prejudice. In order to understand the thermodynamic stability of DCMTase:DNA interactions in a diverse population of CpG sequence contexts, as might be expected in vivo, we devised an in vitro screening protocol that exploits the gel mobility shift assay. The reaction conditions used for each iterative generation of the screening are summarized in Table 2. The first round of screening contained ten times more DNA molecules than the maximal population complexity of 2.8× 10$^{11}$ discrete sequences. An increasing fraction of the added randomized pool was shifted through the first three generations, during which the enzyme concentration was kept constant and the DNA concentration was decreased. The initial conditions were sufficient to stabilize binding of the DNA pool, so the selective pressure to discriminate between sequences was increased in generation-4 and 5 by decreasing both enzyme and DNA concentrations. The maximal population complexity in each generation decreases because only a fraction of the added DNA was shifted. The complexity of the starting population is divided by the percentage of DNA shifted in each generation and ultimately results in no more than $1.2 \times 10^4$ discrete sequences in the generation-5 pool (Table 2).

TABLE 2

Binding conditions and gel shift results of in vitro screening[a]

| Iterative Generation | DCMTase Concentration | DNA Concentration | Percentage *DNA Shifted | Maximal Population Complexity |
|---|---|---|---|---|
| 0 | — | — | — | $2.8 \times 10^{11}$ |
| 1 | 68 nM | 50 nM | 1.5% | $4.2 \times 10^9$ |
| 2 | 68 nM | 25 nM | 12% | $5.0 \times 10^9$ |
| 3 | 68 nM | 12.5 nM | 25% | $1.2 \times 10^8$ |
| 4 | 5.0 nM | 0.125 nM | <1% | $1.2 \times 10^6$ |
| 5 | 0.50 nM | 0.030 nM | <1% | $1.2 \times 10^4$ |

[a]Listed are the enzyme and DNA substrate concentrations used in each round of selection. The Cerenkov cpm within the excised gel slice, containing the shifted complex, is shown as a percentage of the total Cerenkov counts loaded onto the gel. This percentage limits the complexity of the DNA pool, therefore it is used to calculate the maximal population complexity in each successive generation.

Individual members from the starting pool and generations-1, 3 and 5 were cloned and sequenced from both strands. Only the guanine containing strands are shown for simplicity in FIG. 7, however, these studies were done using unmethylated double-stranded substrates. Synthesis of the starting population is shown to be randomized at each position with the expected frequency approximating 1/3 each in guanine, adenine and thymine.

The selected pools successively became more guanosine-rich with each generation. A total of 49 isolates were cloned and sequenced from the generation-5 pool and none were identical. Nucleotide, dinucleotide and trinucleotide frequencies were analyzed using the COMPOSITION (Wisconsin Sequence Analysis, Madison, Wis.). The selected nucleotides flanking the central CpG dinucleotide were 64.7% in guanine, 13.8% in adenine and 21.6% in thymine. The mean frequency of guanine bases per generation-5 isolate was 14.5 out of the 24 selectable positions and more guanines were observed on the 5'-flank compared to the 3'-flank (p=0.04). The far flanking regions are a full helical turn distal to the invariant CpG and are highly enriched in guanine as compared to regions proximal to the CpG. In addition to the abundance of guanosyl—guanosyl (GpG) dinucleotides, guanosyl-thymidyl (GpT) and thymidyl-guanosyl (TpG) dinucleotides appear often and occur more frequently on the 3'-flank (p=0.01). Trinucleotide analyses reinforce the observations at the nucleotide and dinucleotide levels. The highest frequency of GpGpG was at the far 5'-flank, while GpTpG and TpGpT trinucleotides were far more abundant in the 3' flank (p=0.01). The discrimination exhibited by DCMTase for generation-5 sequences may reflect an important structural characteristic that contributes to stabilization of the initial DCMTase:DNA complex. These analyses suggest that an ideal substrate has sequence assymmetry around the CpG and that there is a particular binding orientation of DCMTase on DNA.

The guanine-richness at each randomized position for the generation-5 isolates is best shown in FIG. 8. The murine DCMTase is a large 183,000 Da protein that selected for sequences extending over the entire 12 base-pairs provided for selection on each side of the central CpG. The Wisconsin Sequence Analysis program CONSENSUS was used to construct a common generation-5 sequence with a certainty level of 60%. The sequence GGGGGGGGRRKKG CGKGGKGKKGKKGG (SEQ ID NO:1), where R is guanine or adenine and K is guanine or thymine, was obtained and is shown to highlight the guanine richness and the preference for GpT and TpG on the 3'-side of the CpG. At a certainty level of 80% the plasticity of sequence preferences can be seen close to the invariant CpG; KGGRKKRD-DDKRCGKRRDKKKKKKKG (SEQ ID NO:2) (D is guanine, thymine or adenine). We have not tested whether the DCMTase can select for sequences out further than 12 base-pairs or if multiple CpG dinucleotides are preferred over the 26 base-pair expanse.

Similar Sequences Occur Frequently in the Genome

We subjected the 49 generation-5 sequences to FASTA searches of the GenBank library to see if similar sequences exist in the genomes of higher eukaryotes. The search was limited in three ways. First, only the mouse and human sequences were searched, even though DCMTase activities have been identified in many metazoan organisms. Second, to be considered further, a "hit" had to be identical at 22 of the 26 base positions, including the central CpG. No hits were retrieved that had a higher identity. Third, no gaps in alignment were allowed.

Remarkably, 20 "hits" were recovered from GenBank that met these severely restricted criteria. FIG. 9 shows the alignments of the five hits from mouse and lists the 15 hits from human. A simplified, random genome would be expected have a complexity of $4^{22}$, or $1.8 \times 10^{13}$ base-pairs, in order to contain any of these sequences just once. Of course, this is an oversimplification. But, the results appear to be striking when considering the mammalian genome is approximately $3 \times 10^9$ base-pairs, only about 40% in guanine plus cytosine, and about 10-fold deficient in CpG dinucleotides. The majority of hits are in what may be presumed to be regulatory regions of the genome; 5' or 3' untranslated regions (UTR) or in CpG islands. Many of the associated genes are also of developmental interest. For example, homeo box Hox2.6 and HoxA7 function in early body segmentation. These findings may reflect an intrinsic function of DCMTase in developmental programming.

Control Experiments Eliminate a Non-Specific Selection

A control series of amplifications in the absence of DCMTase were done to show that our iterative PCR conditions were not responsible for the guanine selection observed with the generation-5 DNA. Endonuclease challenge was done with Taq I (5'-TCGA-3' restriction) and Aci I (5'-GCGG-3' restriction) to assess the randomness of mock selected and DCMTase selected pools. Although this is a limited sampling, the DNA specificity of these enzymes can discern the relative abundance of nucleotides immediately flanking the CpG. The guanine-richness is probed by Aci I and the adenine/thymine-richness is probed by Taq I. After endonuclease challenge of $^{32}$p labeled DNA, the products were resolved on a 12% polyacrylamide gel. Using densitometry, the intensities of the restricted bands were compared to unrestricted control bands. The mock generation-5 sequences immediately flanking the CpG remained random, approximately 6% of the DNA was restricted by each endonuclease, demonstrating that a non-specific selection did not occur under these experimental conditions. Results with the DCMTase selected generations were consistent with the guanine/cytosine selection determined from sequencing individual clones. Also, consistent with a lack of selection from the protocols alone, the entire mock selected pool was sequenced and compared to the DCMTase selected generation-5 pool, similar to that done by Blackwell et al., 1991. An equal abundance of the randomized nucleotides was resolved for the mock selected pool and a guanine-rich population was resolved for the DCMTase selection.

Figure 10:
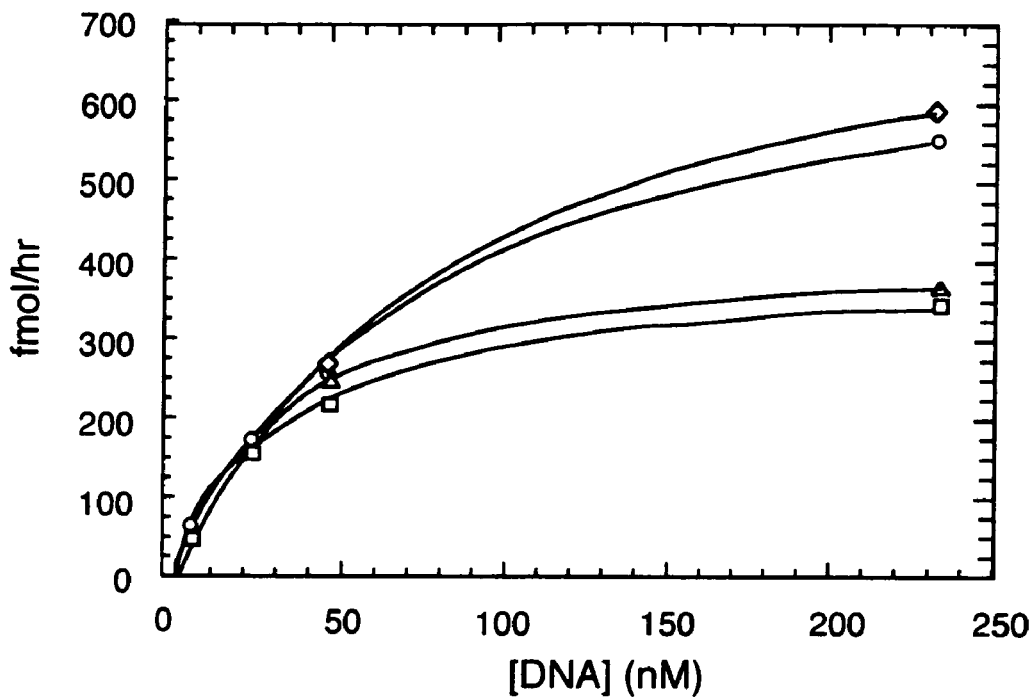
FIG. 10 shows initial velocity curves of the selected generations. Squares, generation-1 pool; triangles, generation-2 pool; circles, generation-4 pool; diamonds, generation-5 pool.

The DCMTase-selected DNA from the iterative generations were compared to each other in binding and catalytic assays. The DCMTase binds the pooled generation-5 sequences only two-fold more tightly than the starting pool. The inherent complexity of each pool makes it difficult to assess the true preference for each generation as a whole. The question of sequence specificity was more accurately addressed by GMSA of the discrete sequences, CRE a/b and GC-box a/b. There we found that the guanine/cytosine-rich GC-box was preferred approximately 3-fold compared to the more adenine/thymine-rich CRE sequence. FIG. 10 shows the initial velocity plots for the starting population and generations-2, 4 and 5. The catalytic specificity for the selected generations increases at each cycle, with little change in $K_m^{DNA}$ and a two-fold increase in $k_{cat}$.

Discussion

Because it is the catalytic agent for cytosine methylation, DCMTase clearly has a central role in both maintaining DNA methylation patterns and in establishing new "epigenotypes". The fundamental issues of binding and catalytic discrimination of the mammalian enzyme for different DNA sequences have been actively debated. Many reports have suggested that the ability of the enzyme to methylate the cognate CpG dinucleotide depends to some degree on flanking sequences (Bolden, A. H., et al., 1986, Primary DNA sequence determines sites of maintenance and de novo methylation by mammalian DNA methyltransferases, Mol. Cell. Bio. 6:1135–1140; Bestor, T. H., et al., 1992, CpG islands in mammalian gene promoters are inherently resistant to de novo methylation, GATA 9:48–53; Hepburn, P. A., et al., 1991, Enzymatic methylation of cytosine in DNA is prevented by adjacent $O^6$-methylguanine residues, J. Biol. Chem. 266:7985–7987; Pfeifer, G. P., et al., 1985, Mouse DNA-cytosine-5-methyltransferase: sequence specificity of the methylation reaction and electron microscopy of enzyme-DNA complexes, EMBO J. 4:2879–2884; Ward, C., et al., 1987, In vitro methylation of the 5'-flanking regions of the mouse b-globin gene, J. Biol. Chem. 262:11057–1106; Carotti, D., et al., 1986, Substrate preferences of the human placental DNA methyltransferase investigated with synthetic polydeoxynucleotides, Biochim. et Biophys. Acta 866:135–143; Smith, S. S., et al., 1992, Mechanism of human methyl-directed DNA methyltransferase and the fidelity of cytosine methylation, Proc. Natl. Acad. Sci. USA 89:4744–4748), while others describe the lack of any flanking sequence effects (Bestor, T. H. and Tycko, B., 1996, Creation of methylation patterns, Nature Genetics 12:363–367; Carlson, L., et al., 1992, Properties and localization of DNA methyltransferase in preimplantation embryos: implications for genomic imprinting, Genes and Development 6:2536–2541). These studies used partially purified or proteolyzed enzyme, substrates containing multiple CpG sites, and compared relative velocities obtained at a single substrate DNA concentration, thereby precluding an accurate estimation of specificity (otherwise known as discrimination).

Similarly, reports regarding the preference of DCMTase for single- and double-stranded substrates are also in direct conflict with one another (Adams, R. L. P., et al., 1986, Mouse ascites DNA methyltransferase: characteristic of size, proteolytic breakdown and nucleotide recognition, Biochim. Et Biophys. Acta 868:9–16; Smith et al., 1992, supra; Carotti et al., 1986, supra; Wang, R. Y. H., et al., 1984, Human placental DNA methyltransferase: DNA substrate and DNA binding specificity, Nucl. Acids Res. 12:3473–3490; Pfeifer et al., 1985, supra; Gruenbaum, Y., et al., 1982, Substrate and sequence specificity of a eukaryotic DNA methylase, Nature 295:620–622; Christman, J. K., et al., 1995, 5-Methyl-2'-deoxycytidine in single-stranded DNA can act in cis to signal de novo DNA methylation. Proc. Natl. Acad. Sci. USA 92:7347–7351).

A recent steady-state kinetic analysis with unmethylated GC-box and CRE DNA sequences showed compensatory 3- to 4-fold changes in $K_m^{DNA}$ and $k_{cat}$ that resulted in a small discrimination at the level of $k_{cat}/K_m^{DNA}$ (Flynn, J., et al., 1996, Murine DNA cytosine-C5 methyltransferase: Pre-steady- and steady-state kinetic analyses with regulatory DNA sequences, Biochemistry 35:7308–7315). In this Example, the sequence-dependent discrimination of DCMTase is quantitatively addressed at the level of $K_D^{DNA}$. The thermodynamic binding constant, $K_D^{DNA}$, is a characteristic of the initial enzyme:DNA complex and $K_m^{DNA}$ has an additional term accounting for the forward reaction rate. DCMTase:DNA interactions were investigated with discrete DNA sequences of biological importance, and with a large divergent pool of DNA sequences. The discrimination between unmethylated single- and double-stranded DNA, and unmethylated and hemi-methylated double-stranded DNA was also quantified.

DCMTase Binding to DNA is Stabilized by Guanine/Cytosine-Rich Sequences

Gel mobility shift assays were used to determine the apparent dissociation constants, $K_D^{DNA}$, of the enzyme for different forms of the GC-box and CRE cis-regulatory elements. Complex, higher-order interactions were observed under the more standard conditions of limiting DNA and varying protein concentrations. While the multiple protein:DNA complexes and unusual DNA concentration dependence are shown to involve the DCMTase, accurate quantitative analysis is precluded due to the uncertainty of binding stoichiometry and the relative affinities of each binding event (Senear, D. F., & Brenowitz, M., 1991, Determination of binding constants for cooperative site-specific protein-DNA interactions using the gel mobility shift assay, J. Biol. Chem. 266:13661–13671; Sackett, D. L. & Saroff, H. A., 1996, The multiple origins of cooperativity in binding to multi-site lattices, FEBS 397:1–6). Whereas many DNA-binding proteins, including DNA adenine-$N^6$ methyltransferases (Reich, N. O. & Mashhoon, N., 1990, Inhibition of EcoRI DNA methylase with cofactor analogs, J. Biol. Chem. 265:8966–8970), form a single protein:DNA complex under similar conditions, bacterial and mammalian DNA cytosine $C^5$ methyltransferases are known to produce multiple complexes at low DNA concentrations (Dubey, A. K. & Roberts, R. J., 1992, Sequence-specific DNA binding by the MspI DNA methyltransferase, Nucleic Acids Res. 20:3167–3173; Mi, S. & Roberts, R. J., 1993, The DNA binding affinity of HhaI methylase is increased by a single amino acid substitution in the catalytic center, Nucleic Acids Res. 21:2459–2464; Reale, A., et al., 1995, DNA binding and methyl transfer catalyzed by mouse DNA methyltransferase, J. Biochem. 312:855–861). The multiple complexes formed with excess enzyme and DNA concentrations far below $K_m^{DNA}$ may be common to cytosine DNA methyltransferases. These complexes are known to be catalytically incompetent in the case of the murine enzyme (Flynn, J., et al., 1996, Murine DNA cytosine-C5 methyltransferase: Pre-steady- and steady-state kinetic analyses with regulatory DNA sequences, Biochemistry 35:7308–7315).

Gel mobility shift assays performed with micromolar DNA concentrations and limiting DCMTase result in a single, shifted DNA band. These observations are again similar to those described for the bacterial cytosine DNA methyltransferases, M.MspI (Dubey & Roberts, 1992, supra) and M.HhaI (Mi & Roberts, 1993, supra); the determination of equilibrium constants under these conditions is valid and not. In fact, our enzyme preparation obeyed classical Michaelis-Menton kinetics with the same substrates when assayed in the same DNA concentration range (Flynn et al., 1996, supra). Also, the estimated $K_D^{DNA}$ values reported in Table 1 are similar to those previously reported at the level of $K_m^{DNA}$ with the same DNA (Flynn et al., 1996, supra). The $K_D^{DNA}$ values are about one-half of those determined at the level of $K_m^{DNA}$ for the same double-stranded substrates. The lack of large differences between these constants suggests that steps following the initial formation of a specific protein:DNA complex do not contribute largely to $K_m^{DNA}$.

DCMTase bound DNA in a 1:1 stoichiometry and had a strong preference for binding double-stranded DNA over single-stranded DNA. Hemi-methylated DNA was bound by the enzyme with slightly higher affinity than unmethylated double-stranded DNA. The $K_D^{DNA}$ data further supports the interpretation that the preference for hemi-methylated DNA versus unmethylated double-stranded DNA derives almost entirely from changes in the methylation rate constant, $k_{methylation}$ (Flynn, J., et al., 1996, Murine DNA cytosine-C5 methyltransferase: Pre-steady- and steady-state kinetic analyses with regulatory DNA sequences, Biochemistry 35:7308–7315). A recent study of M.HhaI:hemi-methylated DNA and M.HhaI:DNA cocrystal structures attempted to rationalize the two to three-fold discrimination manifested by this enzyme at the level of binding (O'Gara M., et al., 1996, A structural basis for the preferential binding of hemimethylated DNA by HhaI-DNA methyltransferase, J. Mol. Bio. 263:597–606). These authors proposed that the binding discrimination derives mostly from a single van der Waals' contact between the Glu$^{239}$ carboxylate and the methyl group of the 5-methyl-2'deoxycytidine. While the DCMTase also has a glutamate at this position (Glu$^{1388}$), we suggest that other differences in the assembly of the active site contribute to the quantitatively larger preference for hemi-methylated DNA shown by the murine enzyme.

The two base-pair, CpG, cognate sequence of the mammalian DCMTase is small compared to the cognate sites of most bacterial DNA methyltransferases. DNA footprint analyses of M.SssI, M.HhaI and M.MspI are consistent with protein:DNA interactions extending over 16 base-pairs (Renbaum, P. & Razin, A., 1995, Footprint analysis of M.SssI and M.HhaI methyltransferases reveals extensive interactions with the substrate DNA backbone J. Mol. Biol. 248:19–26; Dubey, A. K. & Roberts, R. J., 1992, Sequence-specific DNA binding by the MspI DNA methyltransferase, Nucleic Acids Res. 20:3167–3173). Thus, the large mammalian DCMTase protein (Glickman, J. F. & Reich, N. O., 1997, Peptide mapping of the murine DNA methyltransferase reveals a major phosphorylation site and the start of translation, J. Biol. Chem. In press) most likely involves DNA contacts outside of this minimal sequence. Support for this is provided by the observation that the guanine/cytosine-rich GC-box element (GGGGCGGGGC (SEQ ID NO:3)) is bound approximately 3-fold more tightly than the adenine/thymine-rich CRE element (TGACGTCA). An in vitro selection method was designed to define both the span of the protein:DNA interface, and the sequence preference of the enzyme for nucleotides flanking the consensus CpG. Previous applications of this strategy were useful in defining a consensus sequence for DNA binding proteins involving large differences in binding energetics between random and target sequences (Kinzler, K. W. & Vogelstein, B., 1989, Whole genome PCR: application to the identification of sequences bound by regulatory proteins, Nucl. Acids Res. 17:3645–3653; Thiesen, H. & Bach, C., 1990, Target detection assay (TDA): A versatile procedure to determine DNA binding sites as demonstrated on SP1 protein, Nucl. Acids Res. 18:3203–3209; Blackwell, T. K., et al., 1990, Sequence-specific binding by the c-Myc protein, Mol. Cell. Bio. 13:5216–5224; He, Y., Stockley, P. G. & Gold, L., 1996, In vitro evolution of the DNA binding sites of *Escherichia coli* methionine repressor, MetJ. J. Mol. Biol. 255:55:66). These selection strategies were extended to identify flanking sequence preferences, where binding discrimination is expected to be much less than when searching for a six to ten base-pair cognate site. One potential outcome would be the lack of any preference, as described for the UBF protein using this method (Copenhaver, G. P., et al., 1994, The RNA polymerase I transcription factor UBF is a sequence-tolerant HMG-box protein that can recognize structured nucleic acids, Nucleic Acids Research 22:2651–2657). A consensus sequence larger than the minimal CpG was not likely to result from this selection process, because genomic sequencing of 5-$^m$C reveals that the enzyme methylates many CpG contexts in vivo.

The screening method employed herein efficiently identified a DCMTase-induced population drift from 33.3% guanosine in the starting randomization to 50.0% in generation-1, 55.3% in generation-3 and finally 64.7% in generation-5. Randomized position 12 (see FIG. 8) was enriched to 88% guanine in generation-5, suggesting that the total sequence space represented by the starting randomization was severely confined. Ultimately, the selection process did not disclose an obvious preferred sequence, but clearly a selection was evident. This is consistent with the observation that roughly $3 \times 10^7$ CpG flanking sequence contexts in the murine genome undergo methylation in vivo.

Sequence analysis of the 49 generation-5 members provided evidence that the DCMTase may bind these substrates in a preferred orientation. A greater guanosine selectivity was associated with the far 5'-side of the CpG and a more divergent region was exposed from the -2 to the -5 positions. The 3'-side of the invariant CpG exhibits a different DCMTase preference; GpT and TpG dinucleotides occur more frequently and are often tandomly arranged. Empirically, the data do not allow for prediction of which strand may be poised to be methylated. The results with the mammalian DCMTase, which suggest sequence-dependent binding affects for a 26 base-pair expanse (or more), are quite reasonable given the DNA footprinting results for the bacterial enzymes mentioned. The binding asymmetry suggested by the results herein was likely induced by the design of the starting population, because one strand was guanine-rich while the other was cytosine-rich. This design was chosen in order to avoid introducing multiple CpG dinucleotides that could complicate the assessment of flanking sequence contributions around a single CpG.

DCMTase Interactions with DNA are Influenced by Helical Geometries

Dinucleotide analysis has been useful for understanding sequence-dependent conformational parameters of DNA (El Hassan, M. A. and Calladine, C. R., 1996, Propeller-twisting of base-pairs and the conformational mobility of dinucleotide steps in DNA, J. Mol. Biol. 259:95–103; Hunter, C. A., 1993, Sequence-dependent DNA structure. The role of base stacking interactions, J. Mol. Biol. 230:1025–1054; Yanagi, K., et al., 1991, Analysis of local helix geometry in three B-DNA decamers and eight dodecamers, J. Mol. Bio. 217: 201–214). The crystallography-derived parameters are generally similar for the protein bound and free states (Calladine, C. R. and Drew, H. R., 1996, A useful role for "static" models in elucidating the behaviour of DNA in solution, J. Mol. Biol. 257:479–485). Dinucleotide conformational parameters have a limited range which are dependent on the two nucleotides immediately flanking the dinucleotide step in question. Because there are 136 four-base steps, the understanding of the sequence-dependent helix geometry at this level is still incomplete (El Hassan & Calladine, 1996, supra; Yanagi et al., 1991, supra). More distant nucleotides also have significant effects on CpG helical parameters (Lefebvre, A., et al., 1996, Solution structure of the CpG containing d(CTTCGAAG)$_2$ oligonucleotide: NMR data and energy calculations are compatible with a BI/BII equilibrium at CpG. Biochemistry 35:12560–12569).

These analyses provide the basis for a qualitative interpretation of DNA conformational features important for the stabilization of the initial DCMTase:DNA complex. Guanosine-rich stretches, best represented in this Example by the GC-box and the selected 5'-regions, often assume an A-DNA conformation. Guanosine-rich helices are underwound because neighboring guanine bases tend to overlap and lead to low dinucleotide twist angles (McCall, M., et al., 1985, The crystal structure of d(G-G-G-G-C-C-C-C). A model for poly(dG):poly(dC). J. Mol. Biol. 183:385–396; Yanagi et al., 1991, supra; El Hassan & Calladine, 1996, supra). Also, base-pair slide is allowed more freely in GpG than other steps, due mainly to a low propeller-twist parameter. A-DNA thus differs from B-DNA in that the minor groove is wide and shallow while the major groove is narrower and deeper. While little is known about the DCMTase:DNA interface, the enzyme contains the peptide motif $^{716}$SPKK$^{719}$, which is found in proteins known to interact with the minor groove of DNA (Churchill, M. & Suzuki, M, 1989, "SPKK" motifs prefer to bind to DNA at A/T-rich sites, EMBO J. 8:4189–4195). The preference for sequences which have A-DNA like features may be due to DCMTase:DNA interactions mediated by this motif at some distance from the protein elements involved in CpG recognition. The GpT and TpG dinucleotide repeats, observed more frequently in the DCMTase selected 3'-flank, have unique sets of conformational parameters that can increase helical flexibility (Nagaich, A. K., et al., 1994, CA/TG sequence at the 5' end of oligo(A)-tracts strongly modulates DNA curvature, J. Biol. Chem. 269:7824–7833; Beutel, B. A. & Gold, L., 1992, In vitro evolution of intrinsically bent DNA, J. Mol. Biol. 228:803–812; Lyubchenko, Y. L., et al., 1993, CA runs increase DNA flexibility in the complex of I Cro Protein with the OR$^3$ site, Biochemistry 32:4121–4127; Haniford, D. B & Pulleybank, D. E., 1983, Facile transition of poly[d(TG):d(CA)] into a left-handed helix in physiological conditions, Nature 302:632–634).

Like the TpG step, CpG is considered "malleable" because the local conformations are dependent on flanking base-pairs (Lefebvre, A., et al., 1996, Biochemistry 35:12560–12569; Lefebvre, A. Mauffet, O., Hartmann, B., Lescot, E. & Fermandjian, S., 1995, Biochemistry 34:12019–12028; Hunter, C. A., 1993, J. Mol. Biol. 230: 1025–1054; Prive, G. G., et al., 1991, J. Mol. Biol. 217: 177–199; Grzeskowiak, K., et al., 1991, J. Biol. Chem. 266:8861–8883). Severe effects on the geometrical parameters associated with a centrally located CpG have been measured for at least 15 different sequences. The structures of two oligonucleotides containing the consensus CRE element, TGACGTCA, have been determined (Mauffet, O., et al., 1992, J. Mol. Biol. 227:852–875; Konig, P. & Richmond, T. J., 1993, J. Mol. Biol. 233:139–154). Several sequences closely related to the GC-box consensus, GGGGCGGGGC (SEQ ID NO:3), have also been crystallized.

A small twist angle is characteristic of CpG embedded in guanine/cytosine-rich sequences and likely adds to the overall A-DNA character (Haran, T. E., et al., 1987, The crystal structure of d(CCCCGGGG): A new A-form variant with an extended backbone conformation, J. Biomol. Struct. Dynam. 5:199–217; Heinemann, U., et al., 1987, Crystal structure analysis of an A-DNA fragment at 1.8 A resolution: d(GC-CCGGGC), Nucl. Acids Res. 15:9531–9549; Rabinovich, D., et al., 1988, Structures of the mismatched duplex d(G-G-G-T-G-C-C-C) and one of its Watson-Crick analogues d(G-G-G-C-G-C-C-C), J. Mol. Biol. 200:151–161; Verdaguer, N., et al., 1991, Molecular structure of a complete turn of A-DNA, J. Mol. Biol. 221:623–635; Frederick, C. A, et al., 1989, Molecular structure of an A-DNA decamer d(ACCGGCCGGT), Eur. J. Biochem. 181:295–307; Conner, B. N., et al., 1984, *Helix* geometry and hydration in an A-DNA tetramer: CCGG. J. Mol. Biol. 174:663–695; McCall et al., 1985, The crystal structure of d(G-G-G-G-C-C-C-C). A model for poly(dG):poly(dC), J. Mol. Biol. 183:385–396). Conversely, adenine/thymine-rich flanking sequences can lead to negative roll and high twist values at the CpG, so that the helix conforms more to B-DNA (Lefebvre, A., et al., 1996, Solution structure of the CpG containing d(CTTCGAAG)$_2$ oligonucleotide: NMR data and energy calculations are compatible with a BI/BII equilibrium at CpG, Biochemistry 35:12560–12569; Mauffet, O., et al., 1992, The fine structure of two dodecamers containing the cAMP responsive element sequence and its inverse, J. Mol. Biol. 227:852–875; Grzeskowiak, K., et al., 1991, The structure of B-helical CGATCGATCG (SEQ ID NO:6) and comparison with CCAACGTTGG (SEQ ID NO:4), J. Biol. Chem. 266:8861–8883; Prive, G. G., et al., 1991, Structure of the B-DNA decamer C-C-A-A-C-G-T-T-G-G (SEQ ID NO:7) and comparison with isomorphous decamers C-C-A-A-G-A-T-T-G-G (SEQ ID NO:5) and C—C-A-G-G-C-T-G-G, J. Mol. Biol. 217:177–199; Bingman, C. A., et al., 1992, Crystal and molecular structure of the A-DNA dodecamer d(CCGTACGTACGG (SEQ ID NO:8)), J. Mol. Biol. 227:738–756). The backbone torsion angles that connect the cytidine and guanosine residues in these structures are particularly interesting. The large slide associated with extensive inter-strand guanine stacking tends to stretch and contort the a and g torsion angles into the $B_{II}$ conformation (Haran, T. E., et al., 1987, The crystal structure of d(CCCCGGGG): A new A-form variant with an extended backbone conformation, J. Biomol. Struct. Dynam. 5:199–217; Rabinovich et al., 1988, supra; Lefebrve et al., 1996, supra; El Antri, S., et al., 1993, Structural deviations at CpG provide a plausible explanation for the high frequency of mutation at this site, J. Mol. Biol. 230:373–378). $B_{II}$ has an unusual trans, trans arrangement of a and g torsion angles that is most often associated with A-DNA. $B_{II}$ may be more readily attained by a CpG with guanine/cytosine-rich flanking sequences than with adenine/thymine-rich ones. Mechanically speaking, the $B_{II}$ conformation allows for a crankshaft motion to modulate a destacking of bases (Haran et al., 1987, supra). This is likely an early event in the base flipping process mediated by DNA methyltransferases (Allan, B. A. & Reich, N. O., 1996, Targeted base stacking disruption by the EcoRI DNA methyltransferase, Biochemistry 35:14757–62).

The functional importance of the CpG phosphate orientation and flexibility, and DCMTase:phosphate interactions in general, have been studied using the M.HhaI:DNA cocrystal structure (Klimasauskas, S., et al., 1994, HhaI methyltransferase flips its target base out of the DNA helix, Cell 76:357–369; Cheng X; Blumenthal R M., 1996, Finding a basis for flipping bases, Structure 4:639–645). This structure has the target cytosine positioned outside of the helical cylinder covalently trapped by the enzyme. Surprisingly few contacts are made directly with the bases and extensive interactions with the backbone are asymmetrically located around the extrahelical cytosine. Interactions with the two phosphates on the 5'-side of this cytosine appear to be particularly important (5'-$^2$pG$^3$pC$^4$pG$^5$ pC$^6$p-3') and only phosphates 2 through 5 show several angstrom displacement when compared to the uncomplexed DNA. The peptide regions which contact the phosphates are conserved among numerous bacterial cytosine DNA methyltransferases (Cheng & Blumenthal, 1996, supra). For M.HhaI, phosphate $^3$p is contacted by Arg$^{165}$ and Ser$^{85}$, and sequence alignment suggests that Arg$^{1315}$ and Ser$^{1233}$ may play analogous roles in the mammalian DCMTase. Also, Arg$^{98}$ which contacts $^5$p and Lys$^{90}$ which contacts 6p in M.HhaI have homologous residues in the DCMTase, namely Lys$^{1245}$ and Arg$^{1237}$.

The murine DCMTase has a DNA binding specificity that is similar to the catalytic specificity. The preference of the enzyme for guanine/cytosine-rich sequences may reflect a preferred positioning of backbone phosphates within the DCMTase:DNA complex. DCMTase may use the specificity advantage in localizing to certain genomic regions or to preferentially methylate guanine/cytosine-rich DNA in vivo. The function of methylation in bacteria as a primitive immune system, may be a major function for the eukaryotic methyltransferases. Many human viruses are very guanine/cytosine-rich and the discrimination we identified may aid in the specific deactivation of infected viral DNA.

Example 2

Kinetic Mechanism and Identification of a Potent Inhibitor of Murine DNA Cytosine-C$^5$ Methyltransferase This example provides four types of steady-state kinetic analyses to identify the order of substrate addition to the enzyme and the order of product release. In addition, this example identifies a potent single-stranded DNA inhibitor of DCMTase.

Materials

S-adenosyl-L-[methyl-$^3$H]methionine (75 Ci/mmol, 1 mCi/ml, 1 Ci=37 GBq) was from Amersham Corporation. Unlabeled AdoMet (Sigma Chemical Company, St. Louis, Mo.) was further purified as described (Flynn, J., et al., 1996, Biochemistry 35:7308–7315). Routinely, 125 mM AdoMet stocks were prepared at a specific activity of 5.8×10$^3$ cpm/pmol. Two lots of poly(dI•dC:dI•dC) were purchased from Pharmacia Biotech, Inc. (Piscataway, N.J.) with an average length of 6250 and 5000 base pairs. DE81 filters were purchased from Whatman, Inc. Other standard chemicals and reagents were purchased from Sigma Chemical Company or Fisher Scientific (Hampton, N.H.).

DNA cytosine C-5 methyltransferase was purified from mouse erythroleukemia cells as described (Xu, G., et al., 1995, Purification and Stabilization of mouse DNA methyltransferase, Biochemi. Biophysi. Res. Communi 207:544–551). Two separate preparations, with concentrations of 380 nM and 260 nM, were confirmed to have equivalent activities with the substrates studied.

DNA Substrate Preparation

The following three oligonucleotides mimic the GC-box transcriptional cis-regulatory element, in bold type, and were prepared as described (Flynn et al., 1996, supra). The central CpG is underlined.

GC-box a: 5'-GGGAATTCAAGGGG CGGGGCAAGGATCCAG-3' (SEQ ID NO:9)

GC-box b: 5'-CTGGATCCTTGCCC CGCCCCTTGAATTCCC-3' (SEQ ID NO:10)

GC-box b$^{MET}$: 5'-CTGGATCCTTGCCC$^m$ CGCCCCTTGAATTCCC-3'

Steady-State Kinetic Assays

Duplicate 25 µL reaction volumes contained 3.0 nM DCMTase and 10 µM AdoMet in MR buffer (100 mM Tris-HCl, pH 8.0, 10 mM EDTA, 200 µg/ml BSA, 10 mM DTT). After preincubation at room temperature for up to 10 minutes, reactions were initiated by the addition of poly (dI•dC:dI•dC) and, if indicated, inhibitor DNA or reaction products. In several experiments it was found that initiating a reaction containing DNA with AdoMet yielded similar results to those routinely used. Single-stranded DNA was heated to 90° C. and quick cooled on ice, prior to initiation of the reaction. Freeze-thawed DNA produced equivalent results. Incubations were at 37° C. for 60 minutes. The poly(dI•dC:dI•dC) concentrations were 2.0, 4.0, 8.0, 16, 35, 80, 160, 250, 400, 700 and 1000 pM. In some experiments, GC-box a/b was the substrate, using 100 nM DCMTase and DNA concentrations of 0.20, 0.40, 1.0, 2.0, 4.0, 8.0, 15, 23 and 35 µM. The reaction was stopped after 60 minutes by transferring 20 µL of the reaction onto a DE 81 filter paper that was processed as described (Flynn et al., 1996). The radioactivity above the background, determined from assays without added poly(dI•dC:dI•dC), was converted to initial velocities and expressed as picomoles of methyl groups transferred to poly(dI•dC:dI•dC) per hour and plotted in double reciprocal form. The substrates poly(dI•dC:dI•dC) and AdoMet, competitor DNA and reaction product concentrations were varied as indicated in the Figures.

Figure 12A:
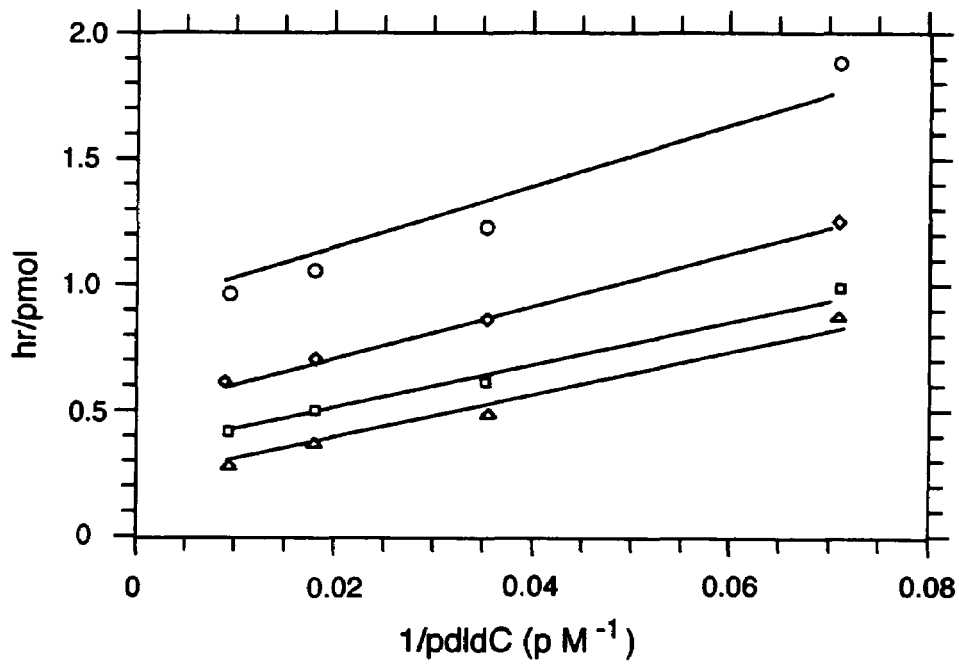
FIG. 12A shows double reciprocal plots of velocity versus substrate concentration. Poly(dI•dC:dI•dC) was varied and lines represent a constant AdoMet concentration: triangles, 4 µM; squares, 2 µM; diamonds, 1 µM; circles, 0.5 µM. Experimental data are shown scattered around lines derived from the fit of equation 2 for a sequential mechanism.
Figure 12B:
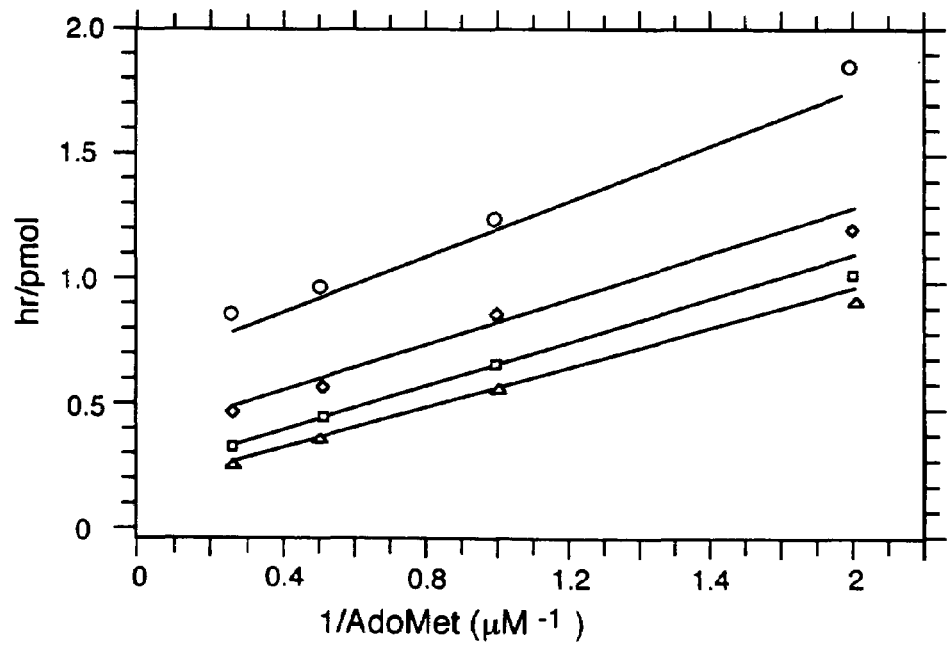
FIG. 12B shows double reciprocal plots of velocity versus substrate concentration. AdoMet was varied and lines represent a constant poly(dI•dC:dI•dC) concentration: triangles, 112 pM; squares, 56 pM; diamonds, 28 pM; circles, 14 pM. Experimental data are shown scattered around lines derived from the fit of equation 2 for a sequential mechanism.

For double reciprocal plots of velocity versus substrate concentration (FIGS. 12A & 12B), reactions contained 20 nM DCMTase in 100 mM Tris pH 8.0, 10 mM EDTA, 10 mM DTT, 200 µg/mL BSA. Incubations were at 37° C. for 60 minutes. For FIG. 12A, poly(dI•dC:dI•dC) was varied at: triangles, 4 µM; squares, 2 µM; diamonds, 1 µM; circles, 0.5 µM, while AdoMet was constant. For FIG. 12B, AdoMet was varied at: triangles, 112 pM; squares, 56 pM; diamonds, 28 pM; circles, 14 pM, while poly(dI•dC:dI•dC) concentration remained constant.

For the double reciprocal plot of velocity versus poly (dI•dC:dI•dC) with varying GC-box b concentrations (FIG. 13), reactions contained 3.0 nM DCMTase and 10 µM AdoMet in 100 mM Tris pH 8.0, 10 mM EDTA, 10 mM DTT, 200 µg/mL BSA. The poly(dI•dC:dI•dC) concentrations were 10, 13, 20, 40 and 100 pM. The GC-box b concentrations were: diamonds, 0; circles, 0.75 µM; triangles, 1.5 µM; squares, 5.0 µM. Incubations were at 37° C. for 60 minutes.

For the double reciprocal plot of velocity vs. poly(dI•dC: dI•dC) with varying GC-box b$^{MET}$ concentrations (FIG. 14), reactions contained 2.0 nM DCMTase and 10 µM AdoMet in 100 mM Tris pH 8.0, 10 mM EDTA, 10 mM DTT, 200 µg/mL BSA. The poly(dI•dC:dI•dC) concentrations were 1.5, 3.0, 7.5, 15 and 20 pM. The GC-box b$^{MET}$ concentrations were: squares, 0; circles, 10 nM; diamonds, 20 nM; triangles, 40 nM. Incubations were at 37° C. for 60 minutes.

Figure 15:
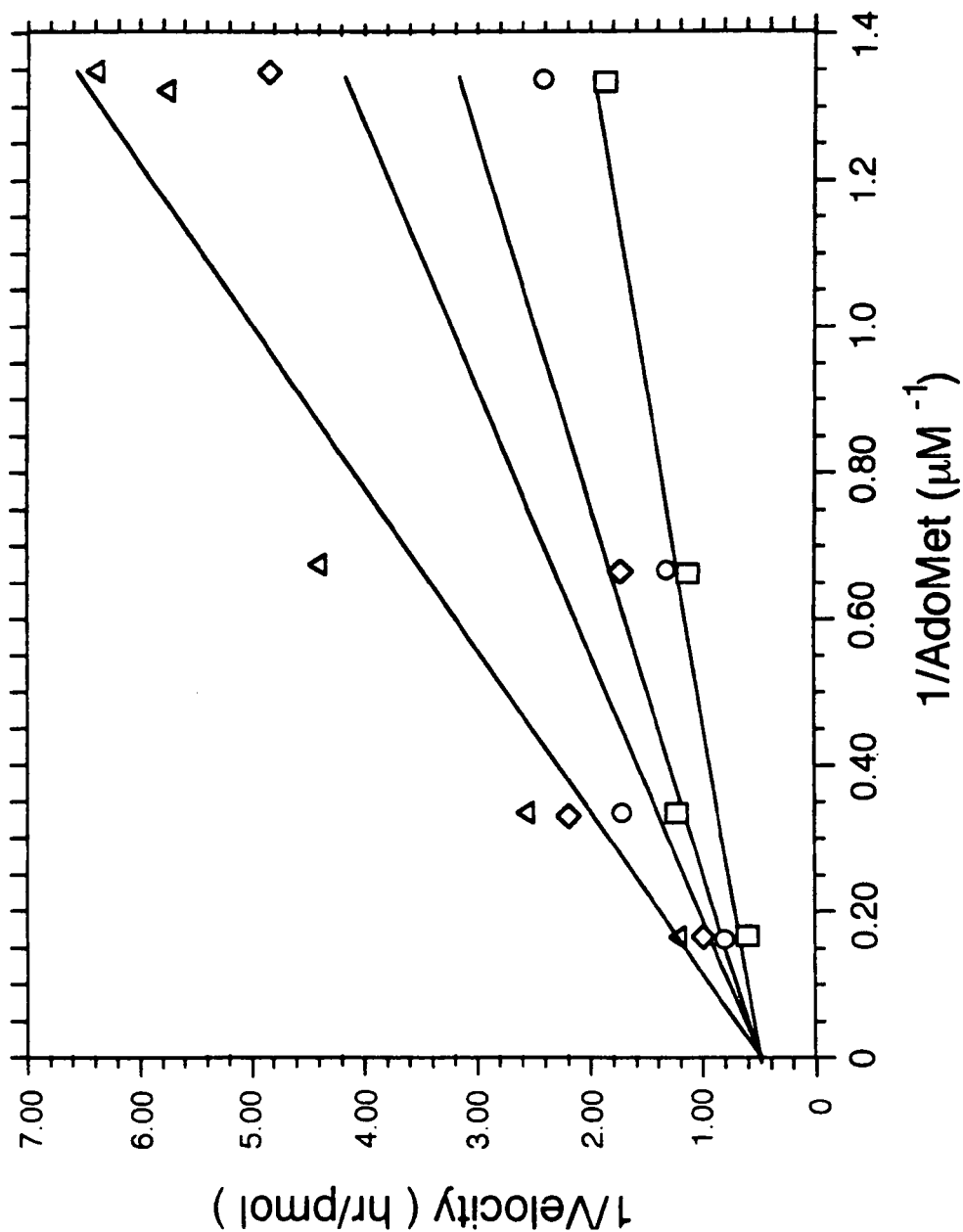
FIG. 15 shows a double reciprocal plot of velocity versus AdoMet with varying GC-box $b^{MET}$ concentrations. The GC-box $b^{MET}$ concentrations were: squares, 0; circles, 20 nM; diamonds, 40 nM; triangles, 80 nM. Experimental data are shown scattered around lines derived from a fit to equation 4 for competitive inhibition.

For the double reciprocal plot of velocity versus AdoMet with varying GC-box $b^{MET}$ concentrations, (FIG. 15), reactions contained 4.0 nM DCMTase and 50 pM poly(dI•dC: dI•dC) in 100 mM Tris pH 8.0, 10 mM EDTA, 10 mM DTT, 200 μg/mL BSA. The AdoMet concentrations were 0.75, 1.5, 3.0 and 6.0 μM. The GC-box $b^{MET}$ concentrations were: squares, 0; circles, 20 μM; diamonds, 40 nM; triangles, 80 nM. Incubations were at 37° C. for 60 minutes.

For the double reciprocal plot of AdoHcy product inhibition with varying AdoMet concentrations (FIG. 16), reactions contained 20 nM DCMTase and 40 pM poly(dI•dC: dI•dC) in 100 mM Tris pH 8.0, 10 mM EDTA, 10 mM DTT, 200 μg/mL BSA. The AdoMet concentrations were 0.50, 1.0, 2.0, 4.0 and 8.0 μM. The AdoHcy concentrations were: squares, 0; diamonds, 0.75 μM; circles, 1.5 μM; triangles, 3.0 μM; notched squares, 6.0 μM. Incubations were at 37° C. for 60 minutes.

Figure 17A:
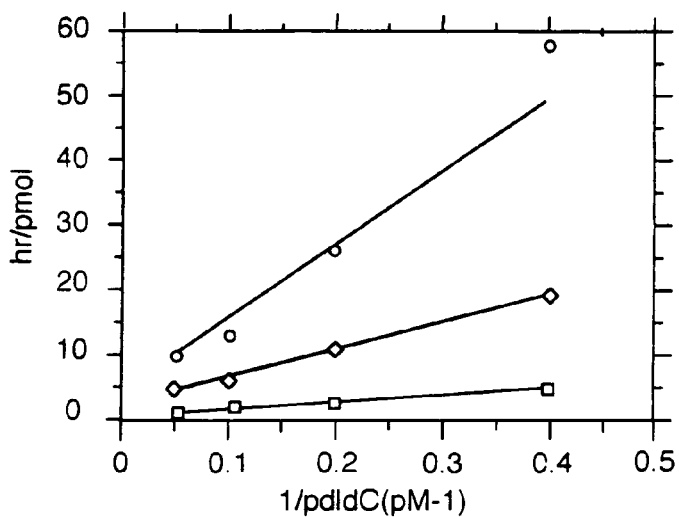
FIG. 17A shows a double reciprocal plot of AdoHcy product inhibition with varying poly(dI•dC:dI•dC) concentrations, in which AdoMet was held constant at 1.2 µM. The AdoHcy concentrations were: squares, 0; diamonds, 15 µM; circles, 30 µM.
Figure 17B:
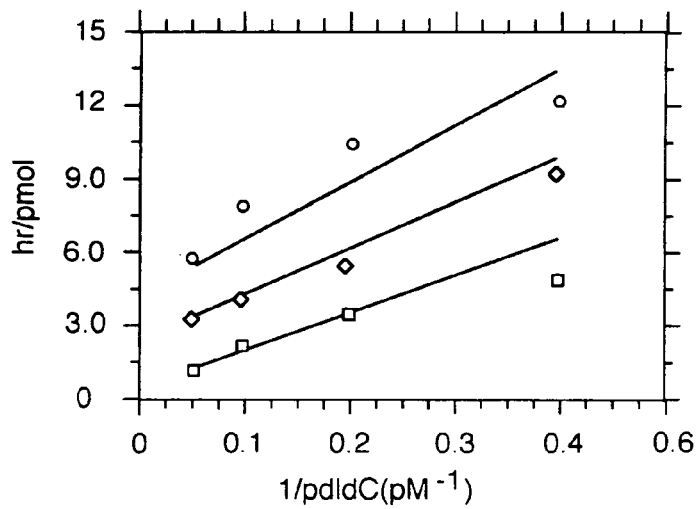
FIG. 17B shows a double reciprocal plot of AdoHcy product inhibition with varying poly(dI•dC:dI•dC) concentrations, in which AdoMet was held constant at 8 µM. The AdoHcy concentrations were: squares, 0; diamonds, 15 µM; circles, 30 µM.
Figure 17C:
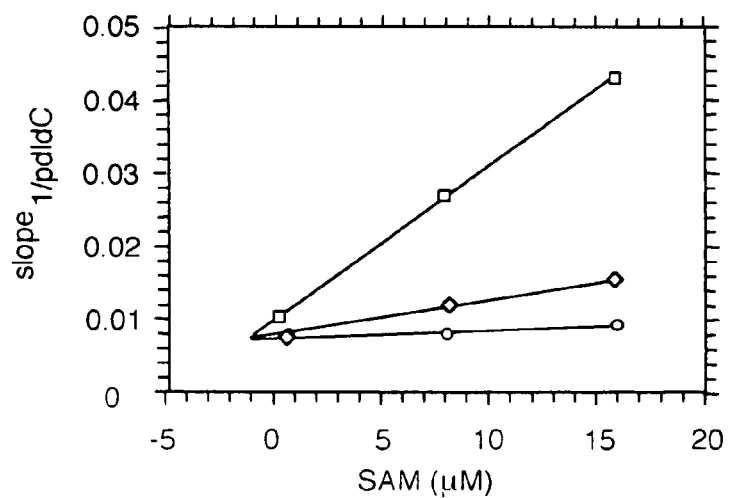
FIG. 17C shows a double reciprocal plot of AdoHcy product inhibition with varying poly(dI•dC:dI•dC) concentrations. The AdoHcy concentrations were: squares, 0; diamonds, 15 µM; circles, 30 µM. These are secondary slope replots from a series of experiments in which the AdoMet concentrations were: circles, 6.3 µM; diamonds, 2.5 µM; squares 1 µM.

For the double reciprocal plot of AdoHcy product inhibition with varying poly(dI•dC:dI•dC) concentrations (FIGS. 17A–C), reactions contained 20 nM DCMTase in 100 mM Tris pH 8.0, 10 mM EDTA, 10 mM DTT, 200 μg/mL BSA. Incubations were at 37° C. for 60 minutes. The poly(dI•dC:dI•dC) concentrations were 2.5, 5.0, 10, and 20 pM. The AdoHcy concentrations were: squares, 0; diamonds, 15 μM; circles, 30 μM. For FIG. 17A, AdoMet was held constant at 1.2 μM. For FIG. 17B, AdoMet was held constant at 8 μM. FIG. 17C shows secondary slope replots from another series of experiments in which the AdoMet concentrations were: circles, 6.3 μM; diamonds, 2.5 μM; squares 1 μM.

Figure 18:
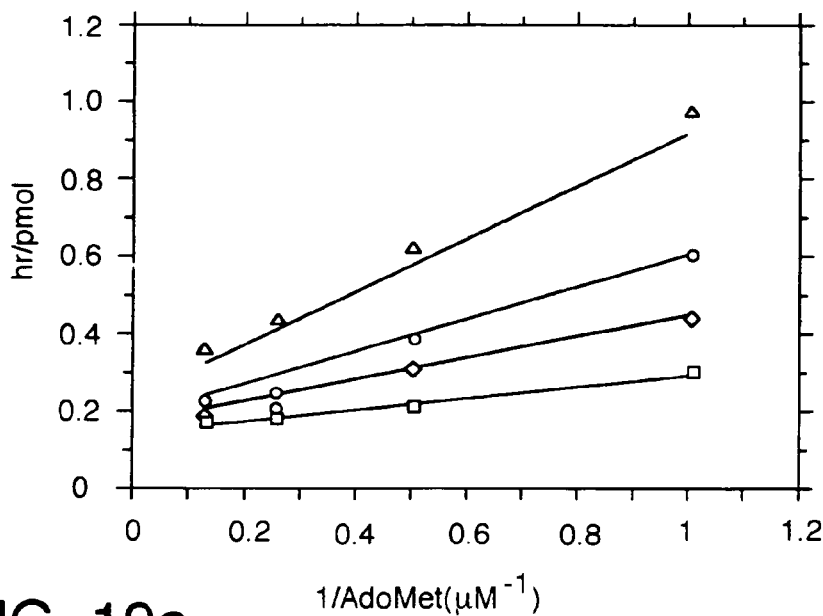
FIG. 18 shows a double reciprocal plot of poly(dId$^m$C:dId$^m$C) product inhibition with varying AdoMet concentrations. The poly(dId$^m$C:dId$^m$C) concentrations were: squares, 0; diamonds, 5.0 pM; circles, 10 pM; triangles, 20 pM. Experimental data are shown scattered around lines derived from a fit to equation 5 for noncompetitive inhibition.

For the double reciprocal plot of poly(dId$^m$C:dId$^m$C) product inhibition with varying AdoMet concentrations (FIG. 18), reactions contained 20 nM DCMTase and 60 pM poly(dI•dC:dI•dC) in 100 mM Tris pH 8.0, 10 mM EDTA, 10 mM DTT, 200 μg/mL BSA. The AdoMet concentrations were 1.0, 2.0, 4.0 and 8.0 μM. The poly(dId$^m$C:dId$^m$C) concentrations were: squares, 0; diamonds, 5.0 pM; circles, 10 pM; triangles, 20 pM. Incubations were at 37° C. for 60 minutes. Experimental data are shown scattered around lines derived from a fit to equation 5 for noncompetitive inhibition.

Figure 19A:
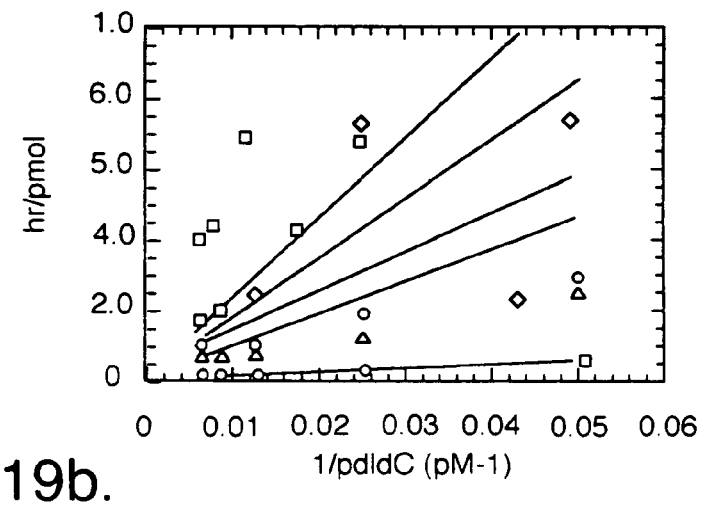
FIG. 19A shows a double reciprocal plot of poly(dId$^m$C:dId$^m$C) product inhibition with varying poly(dI•dC:dI•dC) concentrations. The poly(dId$^m$C:dId$^m$C) concentrations were: squares, 0; triangles, 34 pM; circles, 45 pM; diamonds, 68, notched squares, 90 pM. Experimental data are shown scattered around lines derived from a fit to equation 4 for competitive inhibition. The fitting is not acceptable.
Figure 19B:
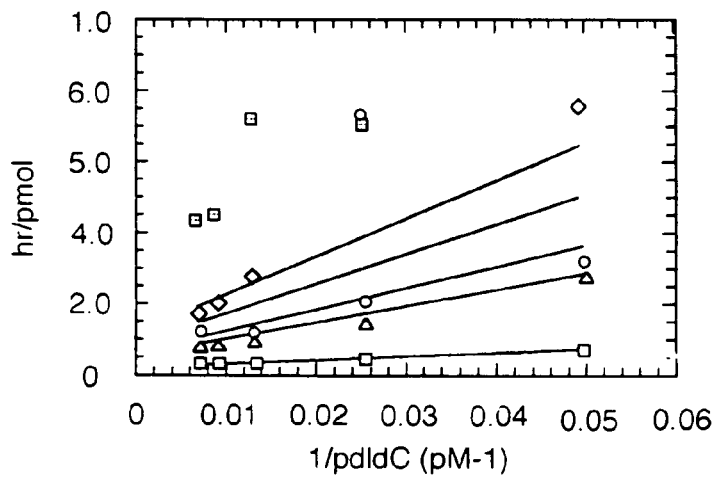
FIG. 19B shows a double reciprocal plot of poly(dId$^m$C:dId$^m$C) product inhibition with varying poly(dI•dC:dI•dC) concentrations. The poly(dId$^m$C:dId$^m$C) concentrations were: squares, 0; triangles, 34 pM; circles, 45 pM; diamonds, 68, notched squares, 90 pM. Experimental data are shown scattered around lines derived from a fit to equation 5 for noncompetitive inhibition. The fitting is not acceptable.

For the double reciprocal plot of poly(dId$^m$C:dId$^m$C) product inhibition with varying poly(dI•dC:dI•dC) concentrations (FIGS. 19A–B), reactions contained 20 μM DCMTase and 1.5 μM AdoMet in 100 mM Tris pH 8.0, 10 mM EDTA, 10 mM DTT, 200 μg/mL BSA. Incubations were at 37-° C. for 60 minutes. The poly(dI•dC:dI•dC) concentrations were 20, 40, 80, 120 and 160 pM. The poly(dId$^m$C:dId$^m$C) concentrations were: squares, 0; triangles, 34 pM; circles, 45 pM; diamonds, 68, notched squares, 90 pM. Experimental data are shown scattered around lines. In FIG. 19A, lines are derived from a fit to equation 4 for competitive inhibition. In FIG. 19B, lines are derived from a fit to equation 5 for noncompetitive inhibition. Both fittings are not acceptable.

Figure 20:
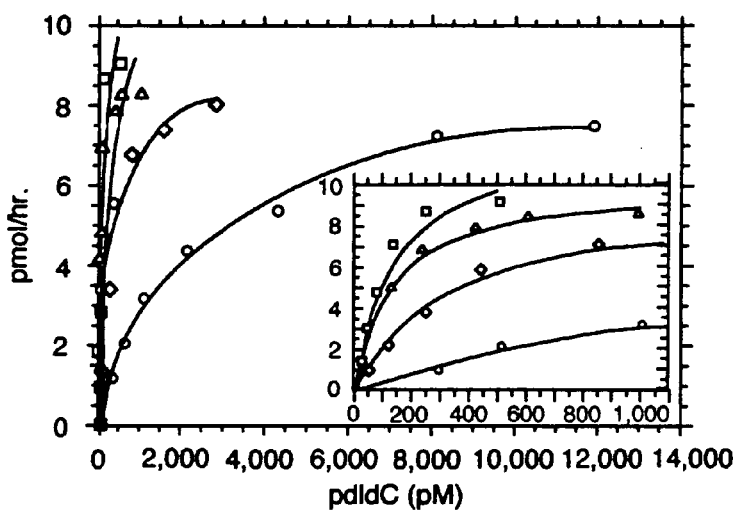
FIG. 20 shows initial velocity plots of different poly(dI•dC:dI•dC) lengths. The poly(dI•dC:dI•dC) sizes were: circles, 100 base-pairs; diamonds, 500 base-pairs; triangles, 2000 base-pairs; squares, 5000 base-pairs. The inset provides a zoom in along the x-axis toward the origin to show the quality of the data.

For initial velocity plots of different poly(dI•dC:dI•dC) lengths (FIG. 20), reactions contained 20 nM DCMTase and 10 μM AdoMet in 100 mM Tris pH 8.0, 10 mM EDTA, 10 mM DTT, 200 μg/mL BSA. Incubations were at 37° C. for 60 minutes. The poly(dI•dC:dI•dC) sizes were: circles, 100 base-pairs; diamonds, 500 base-pairs; triangles, 2000 base-pairs; squares, 5000 base-pairs. The inset provides a zoom in along the x-axis toward the origin to show the quality of the data.

Fragmentation of Poly(dI•dC:dI•dC)

Sonication was used to break a 5000 base-pair average length poly(dI•dC:dI•dC) to lengths of approximately 2000, 1400, 600, 500 and 100 base-pairs using a Branson Sonifier 450 with a microbore tip. Lengths were estimated by agarose gel electrophoresis using DNA size standards.

Preparation of Poly(dI•d$^m$C:dI•d$^m$C)

Poly(dI•dC:dI•dC) was methylated to completion with M.SssI (New England Biolabs). The methylation reaction was optimized and the apparent $K_m^{DNA}$ was determined to be 0.40 nM for M.SssI using 6250 base-pair poly(dI•dC: dI•dC). For reaction efficiency and sufficient yields, a 500 μL reaction contained 1.0 nM poly(dI•dC:dI•dC). AdoMet was added to 100 μM to provide an excess level of methyl-groups to complete the reaction. Three 20 unit aliquots of M.SssI were added every 10 hours in MR buffer. After cleaning the DNA by standard organic extraction methods, it was resuspended to 10 nM in TE (10 mM Tris pH 8.0, 1 mM EDTA) and subjected to the methylation reaction using M.SssI and radiolabeled AdoMet. Background, 230 cpm, was detected with this preparation at 0.80 nM and a similar control experiment with 0.80 nM unmethylated poly(dI•dC: dI•dC) generated 37,000 cpm. The methylated DNA, poly (dI•d$^m$C:dI•d$^m$C), was resistant to digestion by HhaI endonuclease and the control DNA was digested to small fragments, as determined by agarose gel electrophoresis.

Isotope Partitioning Analysis

A pre-steady-state approach was used to determine the catalytic competency of the DCMTase:AdoMet complex. The complex was formed at 37° C. using 20 nM DCMTase and tritiated AdoMet at a concentration of 10 μM. The reaction was initiated by adding a mixture of 400 pM poly(dI•dC:dI•dC) and 100 mM unlabeled AdoMet. After a one hour incubation at 37° C., the reactions were treated as stated above.

Molecular Partitioning Analysis

A pre-steady-state approach was used to determine the catalytic competency of the DCMTase:DNA complex. Two different sizes of substrate DNA, 1400 and 600 base-pair poly(dI•dC:dI•dC), were used to distinguish if the initial complex proceeded in the forward direction or dissociated before DCMTase performed chemistry. The complex was formed at 37° C. for 1.5 minutes with 5 nM DCMTase and the 1400 base-pair poly(dI•dC:dI•dC) at 0.20 nM, then a mixture containing 2.0 μM tritiated AdoMet (neat stock concentration, 13 μM) plus an excess of the molecular competitor, 600 base-pair poly(dI•dC:dI•dC) at 5.0 nM was added to initiate catalysis. Aliquots were removed at 1.5, 3 and 9 minutes followed by centrifugation through a P-6 spin column (Bio-Rad) to trap unincorporated label. DNA were separated on an 6% polyacrylamide, 8M urea gel run at 400 V for 4.5 hours. Standard methods of fluorography were used with LiquiScint (National Diagnostics) as the fluor. The dried gel was exposed to Fuji XAR film for three months at −70 C.

Data Analysis

The Michaelis-Menton equation was used for studies into DNA length contributions to catalysis using KaliedaGraph 2.1.2 (Synergy Software). For mechanistic determinations, the nomenclature used is that of Cleland, W. W., 1963a. Biochimi. Biophysi. Acta 67:104–137. All steady-state data were analyzed using regression analyses of the appropriate initial velocity equation, listed below, using the Cleland programs (Cleland, W. W., 1979, Statistical analysis of enzyme kinetic data, Methods in Enzymol. 63:103–138).

$$\text{Substrate Inhibition } v = \frac{VA}{K_a + A + A^2/K_i} \quad (1)$$

$$\text{Sequential Mechanism } v = \frac{VAB}{K_{ia}K_b + K_aB + K_bA + AB} \quad (2)$$

$$\text{Ping Pong Mechanism } v = \frac{VAB}{K_aB + K_bA + AB} \quad (3)$$

$$\text{Competitive Inhibition } v = \frac{VA}{K_a(1 + K_{is}) + A} \quad (4)$$

$$\text{Noncompetitive Inhibition } v = \frac{VA}{K_a(1 + K_{is}) + A(1 + K_{ii})} \quad (5)$$

$$\text{Uncompetitive Inhibition } v = \frac{VA}{K_a + A(1 + K_{ii})} \quad (6)$$

The algorithms perform a non-linear least squares fit to the entire data set. Mechanistic determinations were made by comparison of the sigma values associated with the fit to each equation. The standard errors associated with fitted parameters and graphical analysis of the experimental data scattered around the calculated best fit lines were also considered in making an assignment.

Preparation of Poly(dI•d$^m$C:dI•d$^m$C)

Poly(dI•dC:dI•dC). was methylated to completion with M.SssI (New England Biolabs, Beverly, Mass.). Optimization of the methylation reaction was investigated and the apparent $K_m^{IC}$ was determined to be 0.4 nM for M.SssI. For reaction efficiency and sufficient yields, a 500 mL reaction contained 1 nM poly(dI•dC:dI•dC). AdoMet was added to 100 µM to provide an excess level of methyl-groups to complete the reaction. Three 20 unit additions of M.SssI were done every 10 hours in our methylation buffer. Complete methylation of poly(dI•dC:dI•dC) was tested. After cleaning the DNA by standard methods, it was resuspended to 10 nM in TE and subjected to the methylation reaction using M.SssI and radiolabeled AdoMet. Background, 230 cpm, was detected with this preparation at 0.8 nM and a control experiment generated 37,000 cpm. The methylated DNA, poly(dI•d$^m$C:dI•d$^m$C), was resistant to digestion by HhaI endonuclease and the control DNA was digested to small fragments, determined by agarose gel electrophoresis.

Fragmentation of Poly(dIdC:dIdC)

Sonication was used to break a 5000 base-pair average length poly(dI•dC:dI•dC) to sizes of approximately 2000, 500 and 100 base-pairs. The sizes were determined by agarose gel electrophoresis and comparison to DNA size standards.

Results

The DNA substrate used in the steady-state studies was poly(dI•dC:dI•dC). This substrate contains tandem methylation sites in which guanosine has been replaced by inosine. Methylation is catalyzed at a higher rate with this substrate than with other DNA (Flynn, J., et al. (1996) Biochemistry 35:7308–7315; Pedrali-Noy, G., & Weissbach, A., (1986) J. Biol. Chem. 261:1, 7600–77602). Poly(dI•dC:dI•dC) provides a uniform sequence and limits the potential complexities found with large cloned sequences that contain many randomly situated CpG dinucleotides, each having different flanking sequence contributions to binding and catalysis (Flynn et al, 1996 supra).

Substrate Inhibition

Figure 11:
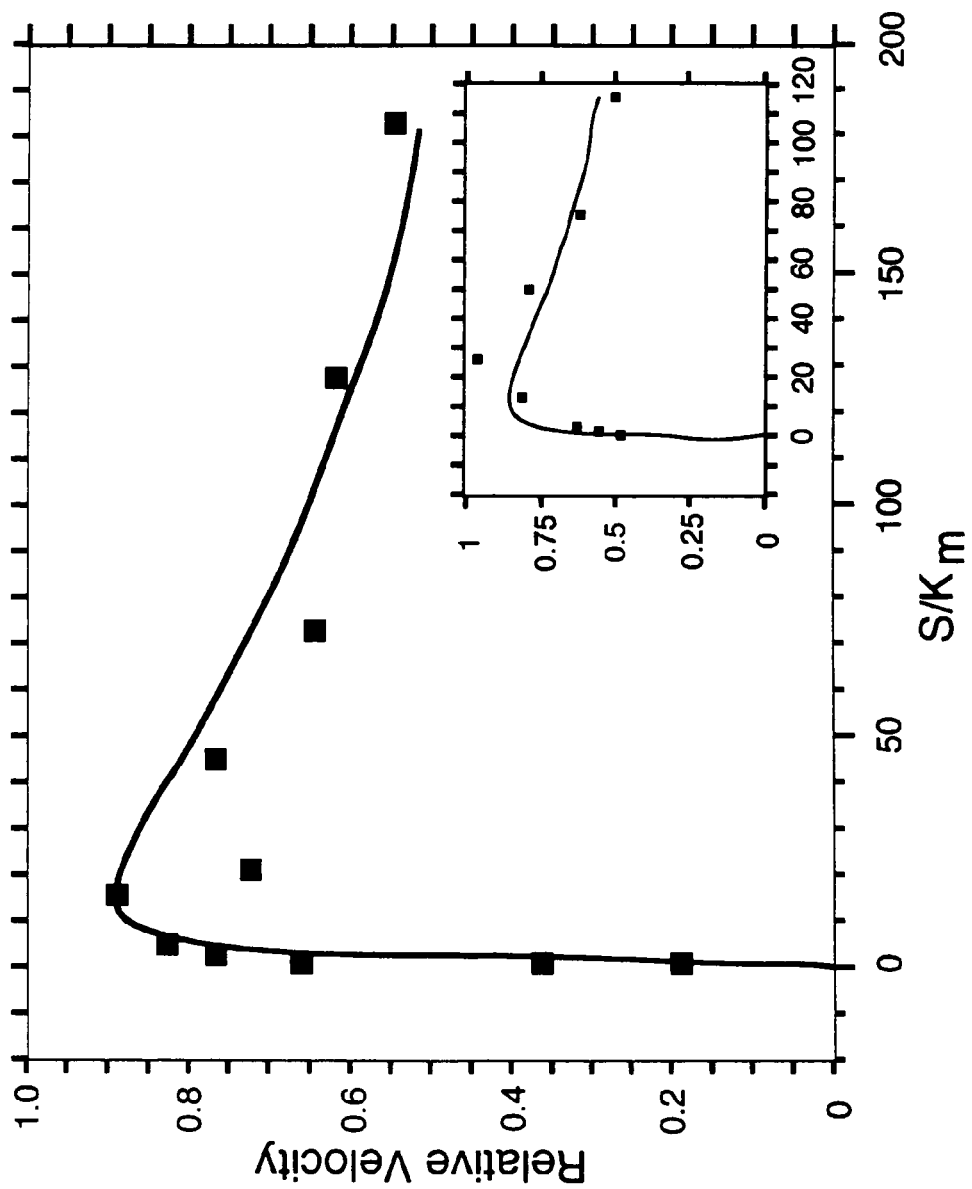
FIG. 11 shows substrate inhibition plots. Reactions contained 3.0 nM DCMTase and 10 µM AdoMet in MR buffer. The inset shows data in which GC-box a/b was the substrate, using 100 nM DCMTase. Experimental data are shown scattered around a line fit to equation 1 for substrate inhibition. For a direct comparison of the DNA substrates, data are expressed as a $V_{max}$ normalized, $S/K_m^{DNA}$ ratio.

Linn and coworkers reported that high concentrations of large DNA resulted in DCMTase inhibition, and proposed that multimeric forms of the enzyme are required for activity (Hitt, M. M., et al., 1988, J. Biol. Chem. 263:4392–4399). To distinguish between this and alternative explanations, a short 30 base-pair DNA substrate was tested for inhibition at high concentrations. FIG. 11 shows the initial velocity results for poly(dI•dC:dI•dC), 6250 base-pairs, and GC-box a/b in terms of reduced concentrations (S/$K_m^{DNA}$). Initial velocity data for both substrates were fit to equation 1, which is a standard equation for analyzing substrate inhibition. $K_m^{DNA}$ was determined to be 5.5+/−0.9 pM and 0.31+/−0.13 µM, and $K_m^{DNA}$ was 1010-+/−170 pM and 43+/−22 µM for poly(dI•dC:dI•dC) and GC-box a/b, respectively (Table 3). In both cases, DNA concentrations greater than 20 times $K_m^{DNA}$ caused substrate inhibition. AdoMet utilization was calculated to be less than 0.5%. Product inhibition by S-adenosyl homocysteine formation is therefore unlikely. AdoMet substrate inhibition was not observed at concentrations up to 30 times $K_m^{AdoMet}$. The substrate inhibition observed implicates a second DNA molecule-binding to the enzyme and inhibiting catalysis.

TABLE 3

| Substrate Inhibition Constants[a] | |
|---|---|
| GC-box a/b | 43000 +/− 22000 nM |
| Poly(dIdC:dIdC) | 1.0 +/− 0.2 nM |

[a]The constants reported, $K_i$ in equation 1, were derived from non-linear regression to the appropriate rate equations as described above. The nomenclature is that of Cleland (1963b).

Initial Velocity Studies with Poly(dI•dC:dI•dC) and AdoMet

Double reciprocal plots of initial velocity versus the substrate concentrations are shown in FIG. 12. DNA concentrations near $K_m$ were used to avoid non-Michaelis behavior (see substrate inhibition studies above). The transformed data were best fit by lines intersecting left of the taxis using a non-linear regression of equation 2, a standard equation for analyzing the steady-state mechanism. The true Michaelis constants derived were $K_m^{pdIdC}$=36+/−5 pM and $K_m^{AdoMet}$=1.4+/−0.2 µM. The intersecting patterns rule out a nonsequential mechanism and implicate a sequential order of substrate addition in which both DNA and AdoMet add to the enzyme surface before products are released. However, a prudent assignment of a kinetic mechanism requires additional kinetic arguments.

Dead-End Inhibition with Single-Stranded DNA

A previous kinetic study showed no detectable enzyme activity with single-stranded GC-box a and GC-box b (Flynn, J., et al., 1996, Murine DNA cytosine-C5 methyltransferase: Pre-steady- and steady-state kinetic analyses with regulatory DNA sequences, Biochemistry 35:7308–7315). In contrast, the DCMTase binds these same oligonucleotide substrates with affinities comparable to those of other DNA (see Example 1). For these reasons it was presumed that single-stranded GC-box substrates could act as dead-end inhibitors of the reaction with poly(dI•dC: dI•dC). Dead-end inhibitors can provide a strong methodology for assessing whether a kinetic mechanism is random or ordered. Inhibition of poly(dI•dC:dI•dC) methylation by single-stranded GC-box b was studied at 15 µM AdoMet. The data were best fit by equation 5, a standard equation for noncompetitive inhibition, and generated the intersecting double reciprocal pattern shown in FIG. 13. The inhibition constants were determined to be $K_{is}$=3.6+/−1.5 µM and $K_{ii}$=6.8+/−1.2 µM (Table 4). $K_{ii}$ is the inhibition constant associated with an intercept effect and $K_{is}$ is the inhibition constant associated with a slope effect from families of double reciprocal plots. An alpha factor, $K_{ii}/K_{is}$, of 1.9 was determined and suggests that the partitioning of this inhibitor slightly favors addition to the free enzyme over the DCMTase:poly(dI•dC:dI•dC) intermediate.

TABLE 4

Dead-End Inhibition Constants and Mode of Inhibition[a]

| DNA | Inhibition Constant (nM) | Mode of Inhibition |
|---|---|---|
| GC-box b | 3600 +/− 1500[b] | Noncompetitive with poly (dIdC:dIdC) |
| GC-box b | 6800 +/− 1200[c] | Noncompetitive with poly (dIdC:dIdC) |
| GC-box b[MET] | 20 +/− 3[d] | Uncompetitive with poly (dIdC:dIdC) |
| GC-box b[MET] | 25 +/− 10[e] | Competitive with Adomet |

[a]The constants reported were derived from non-linear regression to the appropriate rate equations as described above. The nomenclature is that of Cleland (1963b).
[b]The inhibition constant refers to the slope derived $K_{ii}$ in equation 5.
[c]The inhibition constant refers to the intercept derived $K_{ii}$ in equation 5.
[d]The inhibition constant refers to the intercept derived $K_{ii}$ in equation 6.
[e]The inhibition constant refers to the slope derived $K_{ii}$ in equation 4.

Figure 14:
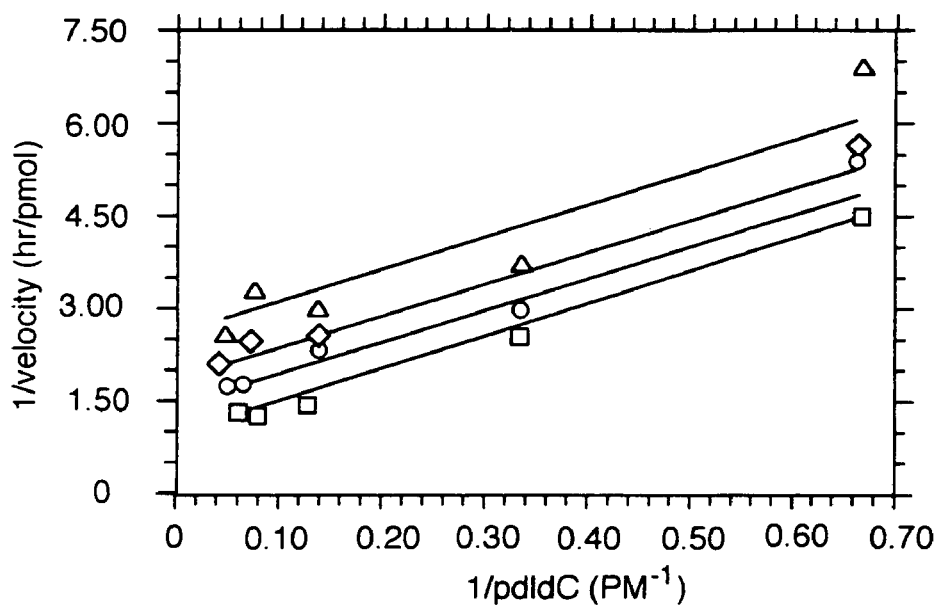
FIG. 14 is a double reciprocal plot of velocity vs. poly(dI•dC:dI•dC) with varying GC-box $b^{MET}$ concentrations. The GC-box $b^{MET}$ concentrations were: squares, 0; circles, 10 nM; diamonds, 20 nM; triangles, 40 nM. Experimental data are shown scattered-around lines derived from a fit to the log form of equation 6 for uncompetitive inhibition.

The CpG methylated homolog of GC-box b, GC-box b[MET], was studied for inhibition under similar conditions. The data were best fit by the log form of equation 6, a standard equation for uncompetitive inhibition. The inhibition constant, $K_{ii}$, was estimated to be 20+/−3 nM. The double reciprocal transformation is shown in FIG. 14. Remarkably, a single 5-[m]C substitution appears responsible for a 200-fold lower inhibition constant and a change in the mode of inhibition. The uncompetitive nature of inhibition suggests that GC-box b[MET] and poly(dI•dC:dI•dC) bind to distinct sites on the DCMTase surface and that poly(dI•dC: dI•dC) binds prior to GC-box b[MET].

Another characterization of the potent inhibition observed with GC-box b[MET] was obtained by varying AdoMet and GC-box b[MET] concentrations using a constant 50 pM poly (dI•dC:dI•dC). The data from initial velocities were best fit to equation 4, which is a standard equation for competitive inhibition. The estimated inhibition constant was $K_{is}$=25+/− 10 µM. The intersection of the fit lines on the 1/velocity axis in FIG. 15 suggests that GC-box b[MET] and AdoMet bind competitively to the same poly(dI•dC:dI•dC)-bound form of the enzyme.

The two inhibition constants determined for GC-box b[MET] are in good agreement at about 20 nM. The patterns observed provide strong evidence for an ordered Bi—Bi kinetic mechanism with substrate DNA binding to the enzyme first and AdoMet binding second, followed by the release of products (Spector & Cleland, 1981, Meanings of Ki for conventional and alternative-substrate inhibitors, Bio. Pharm. 30:1–7). In the absence of poly(dI•dC:dI•dC), GC-box b[MET] bound free enzyme with a 120-fold lower affinity (see Example 1).

Product Inhibition Studies

Product inhibition studies were pursued to further identify the steady-state kinetic mechanism (Table 5). The DCMTase reaction product AdoHcy was a competitive inhibitor of AdoMet. The competitive nature of AdoHcy with respect to AdoMet binding, $K_{is}$=1.4+/−0.2 µM, suggests that AdoMet and AdoHcy bind to the same form of the enzyme (FIG. 16) or that the kinetic mechanism is Theorell-Chance. The Theorell-Chance kinetic mechanism is a simplification of the Ordered B-Bi scheme.

TABLE 5

Product Inhibition of Murine DNA Cytosine-C[5] Methyltransferase.[a]

| Product | Varied Substrate | Fixed Substrate | Type of Inhibition | Inhibition Constant[b] |
|---|---|---|---|---|
| I[m]C | IC | AdoMet | NC | nd[c] |
| I[m]C | AdoMet | IC | NC | Kis 5.3 +/− 2.1 pM |
| | | | | Kii 30 +/− 12 pM |
| AdoHcy | IC | AdoMet | NC/UC | Nd[d] |
| AdoHcy | AdoMet | IC | C | Kis 1.4 +/− 0.2 µM |

[a]I[m]C, fully methylated poly(dIdC:dIdC); IC, poly)dIdC:dIdC); AdoHcy, S-adenosyl homocysteine; AdoMet, S-adenosyl methionine; C, competitive; NC, noncompetitive; UC, uncompetitive inhibition.
[b]Kis refers to the inhibition constant derived from a slope affect. Kii refers to the inhibition constant derived from an intercept affect.
[c]nd, not determined. The determination of an inhibition constant may be complicated by binding to a second nucleic acid binding site on the DCMTase.
[d]nd, not determined. The inhibition constants are dependent on the fixed AdoMet concentration and inhibition is not overcome by saturating AdoMet concentrations. Instead, the inhibition profiles are noncompetitive-like at low AdoMet and uncompetitive-like at high AdoMet concentrations.

A distinctive inhibition profile is revealed with varying AdoHcy and poly(dI•dC:dI•dC). Two families of plots were obtained with AdoMet at different constant levels, 1.2 µM and 8 µM (FIGS. 17A and 17B, respectively). Increasing the AdoMet concentration had the gradual effect of changing the plots from a noncompetitive-like pattern at concentrations near $K_m^{AdoMet}$ to an uncompetitive pattern at higher AdoMet concentrations. There is a decrease in scale of the y-axis in FIG. 17B compared to 17A and a lack of a significant change of the data collected at high poly(dI•dC:dI•dC) concentrations, the points closest to the y-axis. The data at low AdoMet concentrations fitted slightly less well to an uncompetitive model, $K_{ii}$=2.0+/−0.6 µM, than to a noncompetitive model that produced the constants $K_{is}$=63+/−71 µM and $K_{ii}$=2.5+/−1.0 µM. The $K_i^{AdoHcy}$ was independently determined in FIG. 15 to be 1.4 µM. The slope and y-intercept replots from each AdoHcy versus poly(dI•dC:dI•dC) series were all linear. Another study confirmed these results and showed a gradual effect of going from a noncompetitive to an uncompetitive model using three AdoMet concentrations; 1, 2.5, and 6.3 µM. This analysis demonstrates that the slope contribution to AdoHcy inhibition is minimal at low AdoMet concentrations, inhibition cannot be overcome by high AdoMet concentrations, and AdoHcy binds to a different enzyme form than poly(dI•dC:dI•dC). This is strong evidence for an Ordered Bi Bi mechanism in which initial DNA binding is followed by AdoMet binding and that the following reaction step is irreversible.

DCMTase:poly(dI•dC:dI•dC)+AdoMet=DCMTase:
poly(dI•dC:dI•dC):AdoMet

Also, the last product to leave the enzyme cannot be AdoHcy if poly(dI•dC:dI•dC) is the first substrate to bind DCMTase. Uncompetitive inhibition with AdoHcy and DNA was also observed with M.HhaI, it provided evidence that a M.HhaI:DNA:AdoHcy complex can form and ruled out a catalytically significant M.HhaI:AdoHcy complex (Wu & Santi, 1987).

Product Inhibition with Poly(dId$^m$C:dId$^m$C)

Fully methylated poly(dId$^m$C:dId$^m$C) was prepared and used as a product inhibitor of the DCMTase reaction. Poly(dId$^m$C:dId$^m$C) was linear noncompetitive with AdoMet when poly(dI•dC:dI•dC) was held constant (FIG. 18; Table 3). The estimated inhibition constants were $K_{is}$=5.3+/−2.1 pM and $K_{ii}$=30+/−12 pM. The noncompetitive pattern with AdoMet supports many different mechanisms including one in which DNA binding occurs prior to AdoMet binding.

Figure 23A:
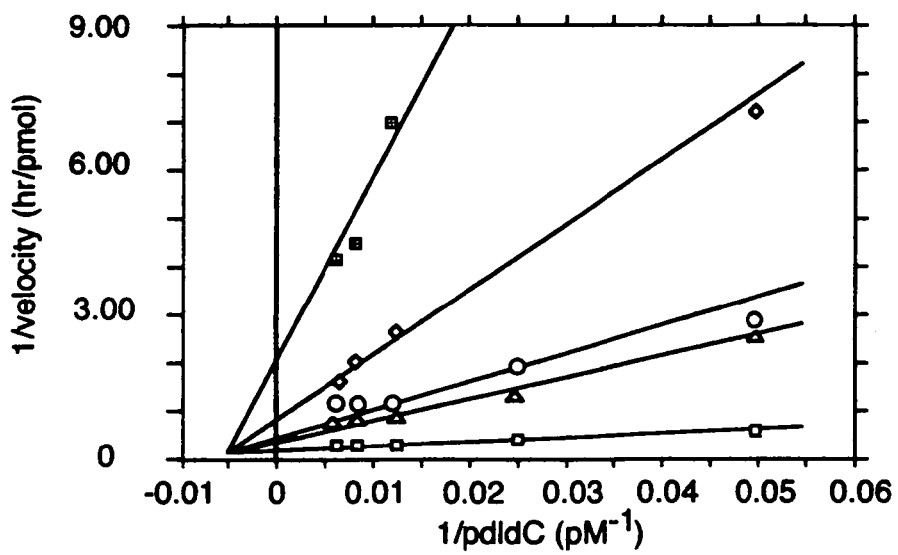
FIG. 23A is a double-reciprocal plot of poly(dId$^m$C:dId$^m$C) product inhibition with varying poly(dI•dC:dI•dC) concentrations. Reactions contained 20 nM DCMTase and 1.5 µM AdoMet in 100 mM Tris pH 8.0, 10 mM EDTA, 10 mM DTT, 200 µg/mL BSA. Incubations were at 37° C. for 60 minutes. The poly(dI•dC:dI•dC) concentrations were 20, 40, 80, 120 and 160 pM. The poly(dId$^m$C:dId$^m$C) concentrations were: squares, 0; triangles, 34 pM; circles, 45 pM; diamonds, 68, notched squares, 90 pM. Shown are the intersecting noncompetitive lines.
Figure 23B:
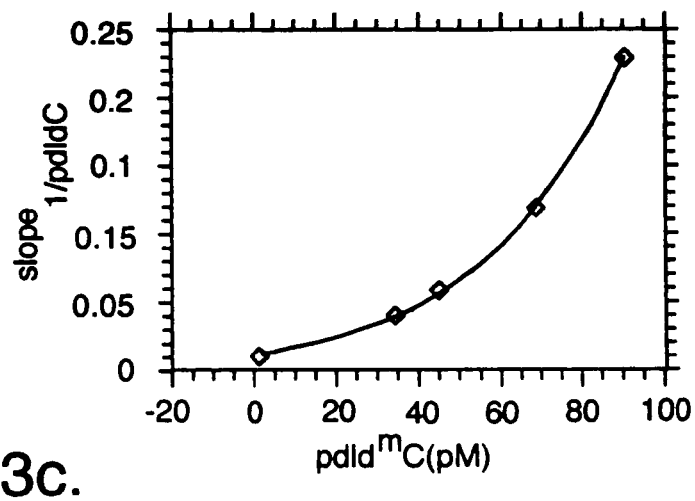
FIG. 23B is the slope replot of the plot shown in FIG. 23A.
Figure 23C:
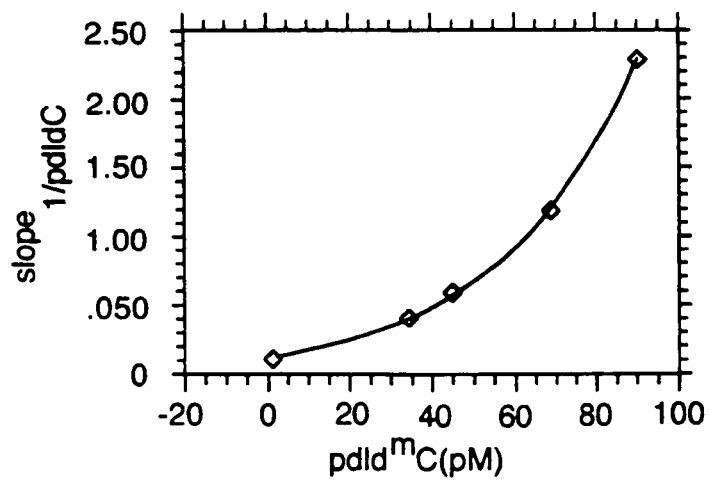
FIG. 23C is the y-intercept replot obtained from the lines in FIG. 23A.

The double reciprocal pattern for methylated DNA product versus DNA substrate would be expected to be competitive in a standard ordered Bi—Bi kinetic mechanism where DNA adds first and methylated DNA leaves last from the catalytically competent enzyme surface. The double reciprocal data obtained on five experiments appeared to be noncompetitive. However, when subjecting the data to fitting by the competitive and the noncompetitive models, graphical analysis showed that fitting in both cases was not acceptable (FIG. 19). This was true for plots obtained with AdoMet concentrations held constant from 1.25 to 12.5 µM. The sensitivity of inhibition was notably abrupt, as poly(dId$^m$C:dId$^m$C) had little effect at 10 pM and completely inhibited the reaction at 100 pM. The results from one experiment are shown in FIGS. 23A–C with idealized lines intersecting left of the y-axis. Secondary slope and y-intercept replots (FIGS. 23B and 23C) were obtained and both were parabolic concave upward. This explains the difficulty in fitting the simple model and is indicative of poly(dI•d$^m$C:dI•d$^m$C) binding at two points in the catalytic cycle. Furthermore, it is evidence that a DCMTase:DNA:DNA complex can be formed. Additional steady-state kinetic experiments also support the existence of an inhibitory DCMTase:DNA:DNA complex.

Isotope Partitioning Analysis with AdoMet

Isotope partitioning analysis is a powerful strategy used to identify catalytically competent enzyme:substrate complexes (Rose, 1980; Reich & Mashhoon, 1991). The DCMTase:AdoMet complex formed with 10 µM radiolabeled AdoMet was not competent for catalysis, because a chase including 400 pM poly(dI•dC:dI•dC) and 100 µM unlabeled AdoMet produced no detectable activity. Substrate inhibition was not observed at high AdoMet concentrations. This is typical for an Ordered Bi Bi mechanism when studying the second substrate by isotope partitioning, because the DCMTase:AdoMet complex must dissociate before DCMTase can bind poly(dI•dC:dI•dC). Under these conditions, the DCMTase:poly(dI•dC:dI•dC) complex would then bind a diluted specific activity AdoMet and catalysis would not be detectable.

Molecular Partitioning Analysis

A novel assay was developed to test the competency of the initial DCMTase:poly(dI•dC:dI•dC) complex. This complex was formed with one DNA length, 1400 base-pairs, and then challenged with an excess of smaller, 600 base-pair DNA combined with AdoMet. The initial DCMTase:poly(dI•dC:dI•dC) complex was observed to be competent for catalysis, because tritium was incorporated into the larger DNA. A control experiment allowed both DNA lengths to compete for DCMTase binding before AdoMet was added, because the smaller DNA was at a sufficiently higher concentration all of the detectable label was incorporated into it. This demonstrates that DNA, under the conditions employed, can bind first in the steady-state mechanism, and limits the assumptions made in other experiments to the Ordered Bi Bi mechanism.

DNA Length Contributions to Catalytic Efficiency

Figure 21:
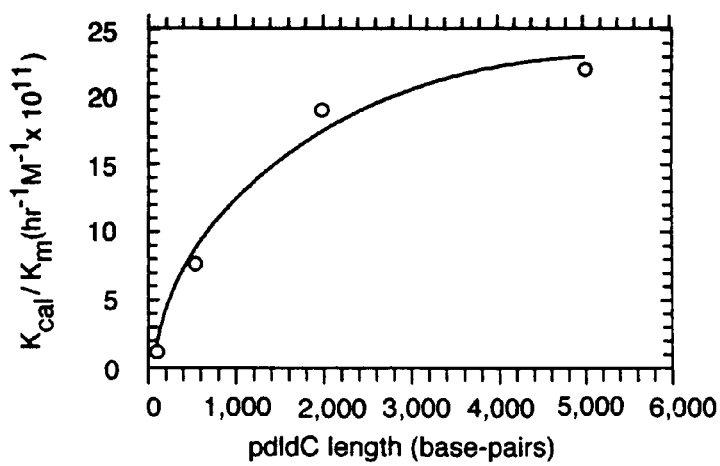
FIG. 21 shows a plot of DCMTase specificity as a function of poly(dI•dC:dI•dC) length. The apparent constants were derived from FIG. 20 and are shown in Table 6. The data was fit well by an isotherm that yielded a half-maximal length of 1200 base-pairs and a maximal specificity value of $29 \times 10^{11}$ hr$^{-1}$pM$^{-1}$ with poly(dIdC:dIdC) as the substrate.

Sonication was used to break a 5000 base-pair average length poly(dIdC:dIdC) to sizes of approximately 2000, 500 and 100 base-pairs. Initial velocity profiles were obtained for each size (FIG. 20), and the kinetic terms are compared in Table 6. A 14-fold increase in $K_m^{DNA}$ was observed as the length decreased 5000 to 100 base-pairs, but $k_{cat}$ only dropped by one-third. The hyperbolic trend in specificity constants, $k_{cat}/K_m^{DNA}$ (FIG. 21), suggests a half maximal length of 1200 base-pairs and that lengths greater than 2000 base-pairs provide little advantage to catalytic specificity. On the contrary, DNA lengths of 500 base-pairs and smaller show a very sharp decrease in specificity. DNA length is thereby critical to maximal performance of DCMTase.

TABLE 6

Poly (dIdC:dIdC) length and Catalytic Efficiency[a]

| Length | Vmax (fmol hr$^{-1}$) | kcat (hr$^{-1}$) | Km (pM) | Kcat/Km (hr$^{-1}$ M$^{-1}$ × 10$^{10}$) |
|---|---|---|---|---|
| 5000 | 12500 +/− 1100 | 31.2 | 140 +/− 30 | 22.2 |
| 2000 | 9950 +/− 390 | 24.9 | 125 +/− 117 | 19.9 |
| 500 | 9120 +/− 290 | 22.8 | 300 +/− 30 | 7.65 |
| 100 | 8600 +/− 210 | 21.5 | 1890 +/− 150 | 1.13 |

[a]Constants were determined from initial velocity analysis using the Michaelis-Mention equation.

Reciprocal plots of both substrates, AdoMet and 100 base-pair poly(dI•dC:dI•dC), were generated. The patterns observed were much like that shown in FIG. 12 with 6250 base-pair poly(dI•dC:dI•dC). Although large effects in the kinetic terms were observed with decreasing poly(dI•dC:dI•dC) length, the mechanism of catalysis does not appear to be affected.

Discussion

The data presented herein clarify some of the basic aspects of how cytosine C-5 methylation is catalyzed and perhaps controlled in eukaryotes. The order of substrate binding appears to be DNA followed by AdoMet and the order of product release appears to be AdoHcy followed by methylated DNA. Three kinetic methodologies support our assignments: initial velocity studies varying both substrates, dead-end inhibition, and product inhibition. DNA substrate inhibition was common to both small, single CpG containing DNA and large, multi-site DNA. A second nucleic acid binding region on the DCMTase, distinct from the active site, is implicated from both the substrate inhibition and the dead-end inhibition studies.

DCMTase Multimerization and Substrate Inhibition

Several of the results bear directly on the previously proposed formation of reversible, multimeric complexes (Reale, A., et al., 1995, DNA binding and methyl transfer catalysed by mouse DNA methyltransferase, Biochem. J. 312:855–861) and the inhibition of DCMTase activity at high DNA concentrations (Hitt, M. M., et al., 1988, De novo and maintenance DNA methylation by a mouse plastytoma cell DNA methyltransferase, J. Biol. Chem. 263:4392–4399). An understanding of the functional form(s) of the DCMTase is essential for future structure-function analysis, and the mechanism of DNA-mediated inhibition may be important for in vivo regulation of the enzyme. The DCMTase in the absence of either DNA or AdoMet exists as a monomer, as determined by size exclusion chromatography (Xu, G., et al., 1995, Purification and stabilization of mouse DNA methyltransferase, Biochemi. Biophysi. Res. Communi. 207:544–551). Active site titration suggests that the enzyme is a functional monomer (Flynn, J., et al., 1996, Murine DNA cytosine-C5 methyltransferase: Pre-steady- and steady-state kinetic analyses with regulatory DNA sequences, Biochemistry 35:7308–7315). Further support for a 1:1 enzyme to DNA catalytic association was provided by gel mobility shift analyses (see Example 1).

Hitt et al, 1988, De novo and maintenance DNA methylation by a mouse plastytoma cell DNA methyltransferase, J. Biol. Chem. 263:4392–4399) proposed that the DCMTase is inhibited at high DNA concentrations by partitioning to a monomeric enzyme bound to DNA, and that protein multimerization results in enzyme activation. An alternative explanation could be that substrate inhibition occurs with the formation of a ternary complex (DCMTase:DNA:DNA). These models were tested with a short DNA substrate that is less likely to support protein multimerization than a long, multi-site substrate. Both substrates clearly showed inhibition at high DNA concentrations, and the normalized inhibition profiles appear very similar (FIG. 11). The corresponding substrate inhibition constants, $K_i$, are 150 to 180 times greater than $K_m^{DNA}$ for these very different DNA molecules (Table 3).

The similar $K_m/K_i$ ratios suggest that the substrate inhibition is insensitive to the number of CpG or CpI— dinucleotides within the DNA. Moreover, the concentration dependencies, particularly with the small DNA, show that the inhibition occurs via an intermolecular process. The results also suggest that the DCMTase has a second DNA-binding site with lower affinity for these substrates than the site involved in catalysis. The formation of an inhibitory, ternary complex that includes two DNA molecules is further supported by our inhibition studies with single-stranded DNA (see below) and the existence of DNA-binding peptide motifs residing in the non-catalytic amino-terminal domain of the enzyme (Bestor, T. H., 1992, Activation of the mammalian DNA methyltransferase by cleavage of a Zn binding regulatory domain, EMBO 11:2611–2617; Chuang, L. S., et al., 1996, Characterisation of independent DNA and multiple Zn-binding domains at the N terminus of human DNA-(cytosine-5_methyltransferase: modulating the property of a DNA-binding domain by contiguous Zn-binding motifs, Chia, J., and Li, B. F. L., J. Mol. Biol. 257:935–948). Example 1 shows that DNA concentrations ten times higher than $K_m$ produce a second less mobile band that is consistant with a second DNA binding event.

Kinetic Analysis of DNA and AdoMet Binding

Knowledge of the order of substrate binding and product dissociation is of critical importance to understanding an enzyme mechanism and the mechanisms of particular inhibitors. A first step in the kinetic characterization for DCMTase is shown in FIG. 12. Several observations suggest that DNA binds first. The dead-end inhibition observed in FIGS. 14 and 15 with GC-box $b^{MET}$ implicates DNA (substrate) binding prior to the inhibitor (ssDNA). These inhibition patterns are inconsistent with both a random mechanism and an ordered addition in which AdoMet must bind prior to DNA (Cleland, W. W., 1963b, The kinetics of enzyme-catalyzed reactions with two or more substrates or products II. Inhibition: Nomenclature and theory, Biochimi. Biophysi. Acta 67:173–187). The gel shift experiments (Example 1) clearly show that DCMTase can bind DNA in the absence of AdoMet. Moreover, cofactor addition had no detectable effect on the binding affinity. While the catalytic competence of the initial binding event is uncertain, the stability of the complex is dependent on DNA sequence.

Figure 16:
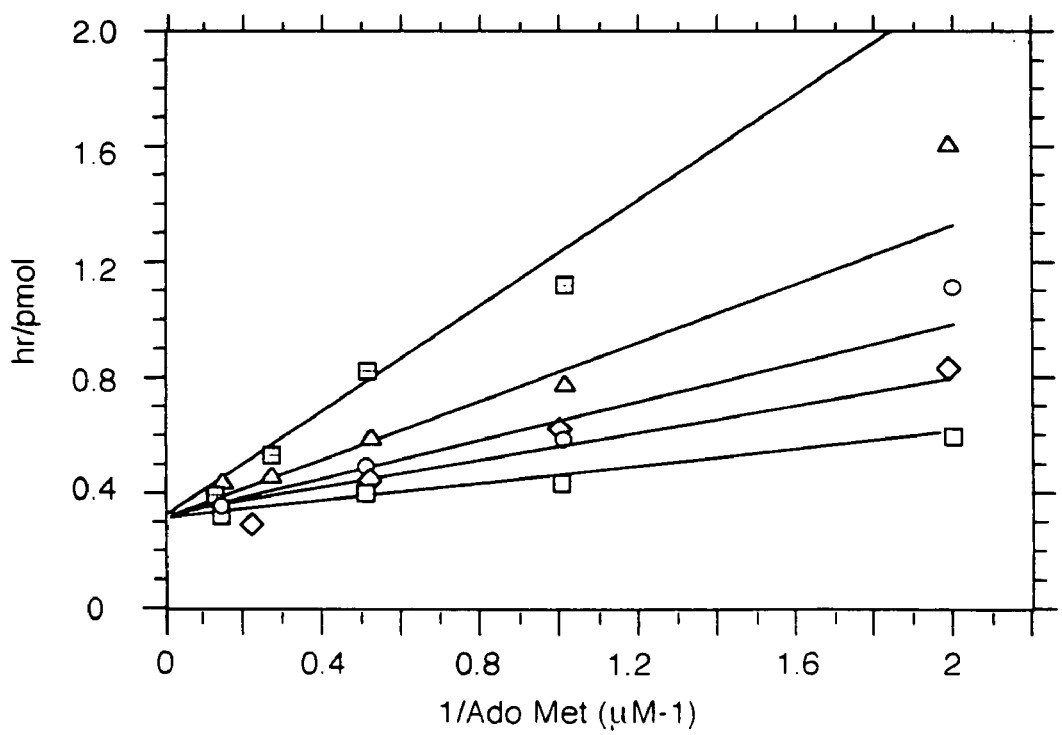
FIG. 16 shows a double reciprocal plot of AdoHcy product inhibition with varying AdoMet concentrations. The AdoHcy concentrations were: squares, 0; diamonds, 0.75 µM; circles, 1.5 µM; triangles, 3.0 µM; notched squares, 6.0 µM. Experimental data are shown scattered around lines derived from a fit to equation 4 for competitive inhibition.
Figure 22:
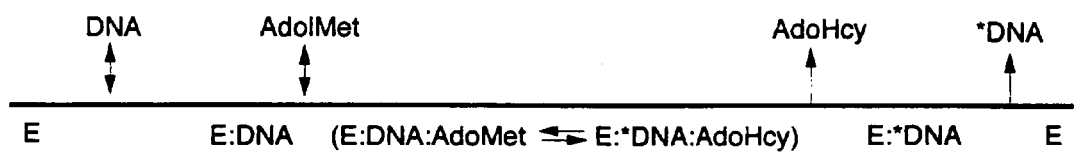
FIG. 22 shows a proposed kinetic mechanism. DCMTase appears to progress through the catalytic cycle by the Ordered Bi—Bi mechanism shown.

The product inhibition studies provided both arguments for and against the classic ordered Bi—Bi mechanism shown in FIG. 22. Two studies were inconsistent with the proposed kinetic order: poly($dId^mC:dId^mC$) inhibition with varied poly(dI•dC:dI•dC), constant AdoMet (FIG. 19) and AdoHcy inhibition with varied AdoMet, constant poly (dI•dC:dI•dC) (FIG. 16). In the first case, it is proposed that the complexities involved with a second DNA binding site have complicated the classic model in ways that are difficult to assess from just these studies. In the second case, AdoHcy exhibited competitive inhibition, but noncompetitive is expected. It may be that AdoHcy is so similar to AdoMet, in that they differ by a methyl group, that the product inhibition does not behave classically. The Theorell-Chance mechanism could also explain this result. Poly($dId^mC:dId^mC$) inhibition with varied AdoMet, constant poly(dI•dC:dI•dC) (FIG. 18) was consistent with the mechanism proposed. Also, it must be considered that the above three product inhibition studies are consistent with many different mechanisms (Segel, 1975, Enzyme kinetics behavior and analysis of rapid equilibrium and steady-state enzyme systems, John Wiley, New York, pg 653). The fourth product inhibition study, AdoHcy inhibition with varied poly(dIdC:dIdC) and constant AdoMet, appeared somewhat complicated (FIGS. 17A–C). Not only is the result consistent with the proposed mechanism, it is uniquely characteristic of it (Segel, 1975, supra).

An overwhelming amount of the data presented herein support a kinetic order as follows: DNA binds, then AdoMet binds and catalysis occurs, AdoHcy leaves followed by methylated DNA (FIG. 22). This proposed mechanism is similar to that described by Wu & Santi (1987, Kinetic and catalytic mechanism of HhaI mehtyltransferase, J. Biol. Chem. 262:4778–4786) for the bacterial DCMTase, M.HhaI. We suggest that the intersecting double reciprocal plots for a rapid equilibrium mechanism observed with M.HhaI and our observation of double reciprocal plots that intersect far from the y-axis with the murine DCMTase may be reconciled by differences in the lifetimes and partitioning of both the enzyme:DNA and enzyme:DNA:AdoMet intermediates.

DNA Length Contributes to Catalytic Efficiency

The investigations into poly(dI•dC:dI•dC) length produced some interesting findings. The apparent $K_m$ systematically increased 14-fold when decreasing the length from 5000 to 100 base-pairs. On the contrary, Table 6 shows that $k_{cat}$ only decreases by one-third. This suggests that assembly of the competent enzyme:DNA:AdoMet complex is difficult and longer DNA promotes catalysis better than small DNA. However, once the complex is formed catalysis can proceed about as well with 100 or 5000 base-pair poly(dI•dC:dI•dC).

Facilitated diffusion of DNA binding proteins and enzymes is a well characterized phenomenon (Surby & Reich, 1996a, Contribution of facilitated diffusion and processive catalysis to enzyme efficiency: implications for the EcoRI restriction-modification system, Biochemistry 35:2201–2208, Surby & Reich 1996b, Facilitated diffusion of the EcoRI DNA methyltransferase is described by a novel mechanism, Biochemistry 35:2209–2217). It appears from these studies that DCMTase also uses facilitated diffusion to seek and stabilize the catalytic complex. The specificity constant determined of $6.1 \times 10^7$ sec$^{-1}$ M$^{-1}$ is within an order of magnitude of the diffusion controlled limit and because this enzyme is unusually slow, $k_{cat}$ under 30 hr$^{-1}$, it is expected that facilitated diffusion contributes largely to catalysis. Processivity has not been addressed in our studies, however, the kinetic mechanism proposed is that expected for a processive enzyme.

Identification of a Potent, Reversible Inhibitor

Figure 13:
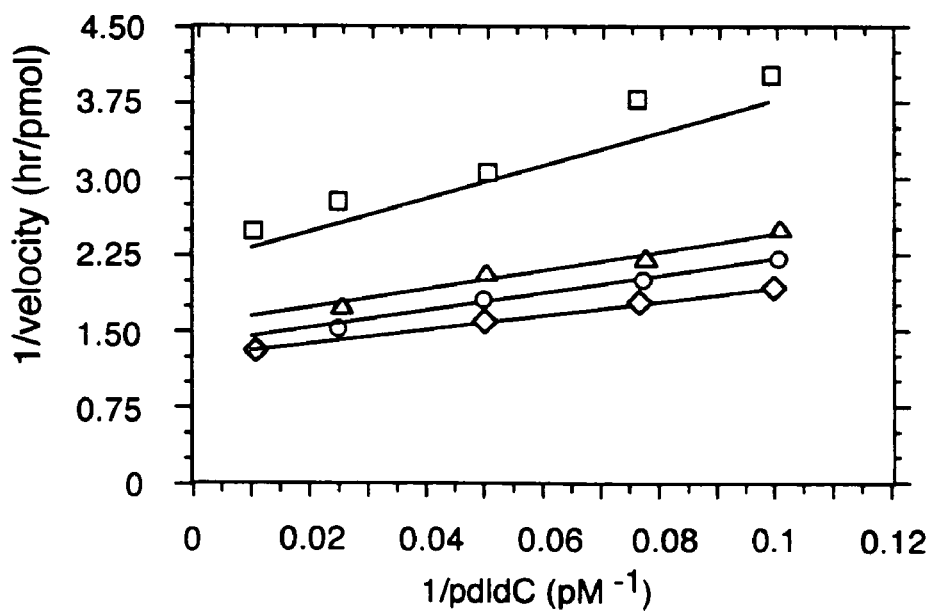
FIG. 13 shows a double reciprocal plot of velocity versus poly(dI•dC:dI•dC) with varying GC-box b concentrations. The GC-box b concentrations were: diamonds, 0; circles, 0.75 µM; triangles, 1.5 µM; squares, 5.0 µM. Experimental data are shown scattered around lines derived from the fit to equation 5 for noncompetitive inhibition.

The finding that single-stranded GC-box a and GC-box b bind with reasonable affinity (Example 1) was somewhat surprising given our inability to detect a significant methyl transfer activity with these sequences. The DCMTase is capable of modifying other ssDNA (Flynn, J., et al., 1996, Murine DNA cytosine-C5 methyltransferase: Pre-steady- and steady-state kinetic analyses with regulatory DNA sequences, Biochemistry 35:7308–7315). When using poly (dI•dC:dI•dC) as the substrate, GC-box b and GC-box b$^{MET}$ showed noncompetitive and uncompetitive inhibition patterns, respectively (FIGS. 13 and 14). Both patterns require that the inhibitors and poly(dI•dC:dI•dC) bind to distinct sites on the enzyme surface. An uncompetitive pattern for GC-box b$^{MET}$ suggests that potent inhibition is through an allosteric site and, in conjunction with the competitive inhibition with AdoMet, strongly implies inhibitor binding to the DCMTase:poly(dI•dC:dI•dC) complex in an ordered Bi—Bi mechanism (Spector & Cleland, 1981, Meanings of Ki for conventional and alternative-substrate inhibitors, Biochem. Pharm. 30:107). The noncompetitive inhibition pattern observed with GC-box b may result through weaker binding at the proposed allosteric site as well as binding at the active site. It is further speculated that the allosteric site is the same site where substrate inhibition originates. Because GC-box b and GC-box b$^{MET}$ differ only in the methylation state of the single CpG, the 200-fold increased inhibition by GC-box b$^{MET}$ is derived from the presence of the methyl group. Whether potent inhibition is caused by the methyl group itself or by greater DNA structural differences is not known.

Knowing that the DCMTase proceeds through the catalytic cycle in an ordered Bi—Bi mechanism allows for the determination of $K_I$, the dissociation constant for GC-box b$^{MET}$ from the DCMTase:poly(dI•dC:dI•dC) complex (Spector & Cleland, 1981, Meanings of Ki for conventional and alternative-substrate inhibitors, Biochem. Pharm. 30:1–7). $K_{ii}$ and $K_{is}$ are conditional and can vary, thus $K_I$ is the proper comparative. It is related to $K_{ii}$ by this relation: $K_{ii}=K_I(1+[AdoMet]/K_m^{AdoMet})$. Solving for $K_I$ using the experimental data from FIG. 14 it is found that $K_I$=2.5 nM, a value about 10-fold lower than catalytic inhibition constant $K_i$.

CONCLUSION

Regulation of DNA replication and transcriptional activation by single-stranded DNA is known to occur (Takai, T., et al., 1994, Molecular cloning of MSSP-2, a c-myc gene single-strand binding protein: characterization of binding specificity and DNA replication activity, Nucleic Acids Res. 22:55776–5581; Rajavashisth, T. B., et al., 1989, Identification of a zinc finger protein that binds to the sterol regulatory element, Science 245:640–643; Tomonaga, T., & Levens, D., 1996, Activating transcription from single stranded DNA, Proc. Natl. Acad. Sci. USA 93:5830–5835). Nucleic acid regulation of DCMTase activity has previously been demonstrated. However, the requirement for micromolar concentrations of the polynucleic acids studied by Bolden et al. (1984, DNA methylation. Inhibition of de novo and maintenance methylation in vitro by RNA and synthetic polynucleotides, J. Biol. Chem 259:12437–12443) to inhibit DCMTase implicates poor binding to the same site suggested in our studies with GC-box b$^{MET}$, or direct binding at the active site as competitive inhibitors. A stimulatory, cis-regulation by methylated CpG sites was reported to occur within single-stranded DNA using crude extracts (Christman, J. K., et al., 1995, 5-Methyl-2'-deoxycytidine in single-stranded DNA can act in cis to signal de novo DNA methylation, Proc. Natl. Acad. Sci. USA 92:7347–7351). While the mechanisms of regulation remain obscure in these cases, it is clear that they are distinct from the inhibition described herein. As previously stated, synthetic peptides mimicking portions of the DCMTase amino-terminus have been shown to gel mobility shift double-stranded DNA (Chuang, L. S., et al., 1996, Characterisation of independent DNA and multiple Zn-binding domains at the N terminus of human DNA-(cytosine-5) methyltransferase: modulating the property of a DNA-binding domain by contiguous Zn-binding motifs, Chia, J., and Li, B. F. L, J. Mol. Biol. 257:935–948). Although single-stranded DNA was apparently not studied, it would be interesting to systematically test these polypeptides for single-stranded DNA binding with and without methylated CpG dinucleotides.

The major finding of this Example concerns the identification of a second nucleic acid binding site that modulates the activity of DCMTase. Both the substrate inhibition studies and the dead-end inhibition studies with CD-box b$^{MET}$ provide strong evidence for the existence of an allosteric site on the DCMTase surface. The kinetic studies demarcate the "allosteric" site, which is necessarily different from the "active" site where catalysis occurs. The novelty of these findings are drawn from the mechanistic insights that define the workings of the enzyme and the modulator in ways that have not been accessible to previous investigators.

GC-box b$^{MET}$ is distinct in form and function from previously described DCMTase inhibitors. There is a need for DCMTase inhibitors that are not incorporated into DNA and that are mechanistically unlike 5-azadeoxycytidine (Belinsky, S. A., et al., 1996, Increased cytosine DNA-methyltransferase activity is target-cell-specific and an early event in lung cancer, Proc. Natl. Acad. Sci. USA 93:4045–4050; Szyf, M., 1996, The DNA methylation machinery as a target for anticancer therapy, Pharmacol. Ther. 70:1–37; Jones, P. A., 1996, DNA methylation errors and cancer, Cancer Res. 56:2463–2467). GC-box b$^{MET}$ clearly interacts with a region of the enzyme that is distinct from the active site and is highly sensitive to the presence of 5-methyl cytosine. The modulator described herein is a reversible antagonist of DCMTase function that provides a new class of therapeutics for treating developmental disorders such as cancer.

Example 3

Anti-proliferative Effects of DCMTase Inhibitors on Cells

It has been observed on several occasions that incubating mouse erythroleukemia (MEL) cells with GC-box $b^{MET}$, GC-box p and GC-box $p^{MET}$ slows down the growth rate. The effect was shown to be concentration dependent. Inhibitor induced anti-proliferation was greatest at a concentration of 10 micromolar, 1 micromolar produced a moderate effect and 0.1 micromolar concentrations produced only a small difference in growth rate in comparison to untreated cells. As observed under the light microscope, concentrations of GC-box $p^{MET}$ and GC-box p exceeding 2.5 micromolar induced MEL cells to produce small refractory particles of unknown content. GC-box $b^{MET}$ also was observed to produce these particles at similar concentrations. The decrease in growth rate became more apparent after six days and three passages of the cells to fresh media containing the same inhibitor concentrations. Also, larger cells began to populate the culture after three days in a similar concentration-dependent manner. These large cells contained multiple nuclei and increased in number as length of incubation increased. After five days of incubation with 10 micromolar GC-box $p^{MET}$, the large multi-nucleate cells were observed to occur at about one in fifty regularly sized cells. Large multi-nucleate cells were also induced using the DCMTase anti-sense phosphorothioate used by Ramachandani et al., 1997 at a concentration of 10 micromolar.

---

What is claimed is:

1. A synthetic oligonucleotide of at least 26 nucleotides in length and comprising a 5mCpG dinucleotide, wherein the 5mC is a C-5 methylcytosine, and which comprises the nucleotide sequence shown in SEQ ID NO:10, wherein the synthetic oligonucleotide comprises a phosphorothioate nucleotide.

2. The synthetic oligonucleotide of claim 1, wherein the oligonucleotide is up to 70 nucleotides in length.

3. The synthetic oligonucleotide of claim 1, wherein the oligonucleotide is up to 50 nucleotides in length.

4. The synthetic oligonucleotide of claim 1, wherein the oligonucleotide is 30 nucleotides in length.

5. A pharmaceutically acceptable salt of a synthetic oligonucleotide of at least 26 nucleotides in length and comprising a 5mCpG dinucleotide, wherein the 5mC is a C-5 methylcytosine, and wherein the synthetic oligonucleotide comprises a phosphorothioate nucleotide.

6. A pharmaceutically acceptable salt of the synthetic oligonucleotide of claim 1.

7. A pharmaceutically acceptable salt of the synthetic oligonucleotide of claim 4.

8. A pharmaceutical composition comprising a synthetic oligonucleotide of at least 26 nucleotides in length and comprising a 5mCpG dinucleotide, wherein the 5mC is a C-5 methylcytosine and wherein the synthetic oligonucleotide comprises a phosphorothioate nucleotide, and a pharmaceutically acceptable carrier.

9. A pharmaceutical composition comprising the synthetic oligonucleotide of claim 1 and a pharmaceutically acceptable carrier.

10. A pharmaceutical composition comprising the synthetic oligonucleotide of claim 4 and a pharmaceutically acceptable carrier.

* * * * *